US005353790A

United States Patent [19]
Jacques et al.

[11] Patent Number: 5,353,790
[45] Date of Patent: Oct. 11, 1994

[54] METHOD AND APPARATUS FOR OPTICAL MEASUREMENT OF BILIRUBIN IN TISSUE

[75] Inventors: Steven L. Jacques; David G. Oelberg; Iyad Saidi, all of Houston, Tex.

[73] Assignee: Board of Regents, The University of Texas System, Austin, Tex.

[21] Appl. No.: 822,461

[22] Filed: Jan. 17, 1992

[51] Int. Cl.$^5$ .............................................. A61B 6/00
[52] U.S. Cl. ................................. 128/633; 128/664; 128/665; 606/3; 250/574; 356/39; 356/51; 356/317
[58] Field of Search ............ 128/633, 664, 665, 653.1; 606/3; 356/39–41; 250/574, 226, 228

[56] References Cited

U.S. PATENT DOCUMENTS

| | | | |
|---|---|---|---|
| 3,569,721 | 3/1971 | Goldberg et al. | 356/39 |
| 3,874,794 | 4/1975 | Schmitt et al. | 356/39 |
| 4,029,085 | 6/1977 | DeWitt et al. | |
| 4,267,844 | 5/1981 | Yamanishi | |
| 4,423,736 | 1/1984 | DeWitt et al. | 128/633 |
| 4,852,025 | 7/1989 | Herpichböhm | 128/633 |
| 4,856,527 | 8/1989 | Karcher et al. | 128/665 |
| 4,997,769 | 5/1991 | Lundsgaard | 356/39 |
| 5,172,693 | 12/1992 | Doody | 128/633 |
| 5,259,382 | 11/1993 | Kronberg | 128/665 |

OTHER PUBLICATIONS

Electronics Engineers' Handbook, FIG. 11-5 "Spectrum of a typical clear mercury lamp", 1982.

Brochure, "Conference on Lasers and Electro-Optics 1990 Technical Digest Series vol. 7," distributed by Optical Society of America, May 21-25, 1990 (Anaheim, Calif.).

Brochure, "Conference on Lasers and Electro-Optics 1991 Technical Digest Series vol. 10," distributed by Optical Society of America, May 12-17, 1991 (Baltimore, Md.).

Alexander, et al., "Determining Skin Thickness with Pulsed Ultrasound," *The Journal of Investigative Dermatology*, 72(1):17-19, 1979.

Anderson, et al., "The Optics of Human Skin," *The Journal of Investigative Dermatology*, 77(1):13-19, 1981.

Andreozzi, G. M., "New Methods for the Diagnosis of Vasculopathies: Reflexion Light Rheography and Transcutaneous Oximetry," *Cardiologia*, 32(11):1431-1439, Nov. 1987.

Ballowitz, et al., "Spectral Reflectance of the Skin," *Biology of the Neonate*, 15:348-360, 1970.

Blois, M. S., "On the Spectroscopic Properties of Some Natural Melanins," *The Journal of Investigative Dermatology*, 47(2):162-166, 1966.

Bohren et al., "Ch. 1, Introduction," Ch. 9, Classical Theories of Optical Constants, Ch. 10, Measured Optical Properties, *Absorption and Scattering of Light by Small Particles*, 1983.

Boulnois, J. L., "Photophysical Processes in Recent Medical Laser Developments: a Review," *Lasers in Medical Science* 1(1)47-66, 1986.

Burgeson, R. E., "The Collagens of the Skin," *Curr. Probl. Derm.*, 17:61-75, (Karger, Basel 1987).

Carr, K., "Integrating Sphere Flux Calculations," *Technical Notes*, by Labsphere, No. 1, Sep. 1, 1988.

Cheong, et al., "A Review of the Optical Properties of Biological Tissues," *IEEE Journal of Quantum Electronics*, 26(12):2166-2185, Dec. 1990.

(List continued on next page.)

Primary Examiner—K. M. Pfaffle
Attorney, Agent, or Firm—Arnold, White & Durkee

[57] ABSTRACT

A method and apparatus for the determination of bilirubin concentration in tissue such as skin, particularly neonatal skin. Light reflected from the skin under test is analyzed to determine bilirubin concentration in the skin, corrected for maturity-dependent optical properties of the skin, the amount of melanin in the skin and the amount of blood in the skin. Reflected red to infrared light is used to determine maturity-dependent optical properties, reflected red light is used to determine melanin content, and reflected yellow-orange light is used to determine the amount of blood in the skin. Then, these quantities are used, in combination with reflected blue light, to calculate cutaneous bilirubin concentration.

13 Claims, 34 Drawing Sheets

OTHER PUBLICATIONS

Engel, et al., "Effect of race and other variables on transcutaneous bilirubinometry," *Pediatric Research,* 15:543, 1982.

Flock, et al., "Monte Carlo Modeling of Light Propagation in Highly Scattering Tissues– I: Model Predictions and Comparisons with Diffusion Theory," *IEEE Transactions on Biomedical Engineering,* 36(12):1162–1168, Dec. 1989.

Hannemann, et al., "Neonatal Serum Bilirubin from Skin Reflectance," *Pediatric Research,* 12(3):207–210, Mar. 1978.

Hannemann, R. E., "Evaluation of the Minolta Bilirubin Meter as a Screening Device in White and Black Infants," *Pediatrics,* 69(1):107–109, Jan. 1982.

Hegyi, et al., "Transcutaneous Bilirubinometry II, Dermal Bilirubin, Kinetics during Phototherapy," *Pediatric Research,* 17(11):888–891, 1983.

Hegyi, T., "Transcutaneous Bilirubinometry in the Newborn Infant: State of the Art, *Journal Clinical Monitoring,* 2(1):53–58, Jan. 1986.

Hegyi, et al., "Transcutaneous Bilirubinometry. I. Correlations in Term Infants," *The Journal of Pediatrics,* 98(3):454–457, 1983.

Henyey, et al., "Diffuse Radiation in the Galaxy," *The Astrophysical Journal,* 93:70–83, Jan.–May, 1941.

Jacques, et al., "Modeling Optical and Thermal Distributions in Tissue During Laser Irradiation," *Lasers in Surgery and Medicine,* 6:494–503, 1987.

Jacques, et al., "Angular Dependence of HeNe Laser Light Scattering by Human Dermis," *Lasers in the Life Sciences,* 1(4):309–333, 1987.

Jacques, S. L., "Simple Theory, Measurements, and Rules of Thumb for Dosimetry During Photodynamic Therapy," *SPIE,* vol. 1065 (*Photodynamic Therapy: Mechanisms*), 100–108, 1989.

Jacques, S. L., "Time–Resolved Reflectance Spectroscopy in Turbid Tissues," *IEEE Transactions on Biomedical Engineering,* 36(12):1155–1161, Dec. 1989.

Jacques, S. L., "The Role of Skin Optics in Diagnostic and Therapeutic Uses of Lasers," *Lasers in Dermatology,* Laser Biology Research Laboratory, University of Texas, 1–21, 1989.

Jacques, et al., "The Melanosome: Threshold Temperature for Explosive Vaporization and Internal Absorption Coefficient During Pulsed Laser Irradiation," *Photochemistry and Photobiology,* 53(6):769–775, 1991.

Johnson, et al., "Development of Human Embryonic and Fetal Dermal Vasculature," *Developing Human Dermal Vasculature,* 93(2):10S–17S, Aug. 1989.

Kapoor, et al., "Uptake and Release of Bilirubin by Skin," *Biochem. J.,* 136:35–43, 1973.

Kato, et al., "Early Detection of Lung Cancer by Means of Hematoporphyrin Derivative Fluorescence and Laser Photoradiation," *Clinics in Chest Medicine,* 6(2):237–253, Jun. 1985.

Katzir, A., "Optical Fibers in Medicine," *Scientific American,* 260(5):120–125, May 1989.

Keijzer, et al., "Light Distributions in Artery Tissue: Monte Carlo Simulations for Finite–Diameter Laser Beams," *Lasers in Surgery and Medicine,* 9(2):148–154, 1989.

Kenny, et al., "Transcutaneous Bilirubin Monitoring of Newborns," *Annals of the New York Academy of Sciences,* 428:251–262, 1984.

Knudsen, et al., "Skin Color and Bilirubin in Neonates," *Archives of Disease in Childhood,* 64:605–609, 1989.

Kollias, et al., "Spectroscopic Characteristics of Human Melanin in Vivo," *The Journal of Investigative Dermatology,* 85(1):38–42, 1985.

Kollias, et al., "Absorption Mechanisms of Human Melanin in the Visible, 400–720 nm," *J. Inves. Derm.,* 89(4):384–388, 1987.

Kopola, et al., "A Skin Erythema Meter," *SPIE, 1201 Optical Fibers in Medicine* (V1990), 345–352, 1990.

Kortum, G. F., *Reflectance Spectroscopy, Principals, Methods, Applications,* Springer-Verlag New York, Inc., 25–37, 1969.

Krauss, et al., "Skin Reflectance in the Newborn Infant," *Pediatric Research,* 10:776–778, 1976.

Maisels, M. J., "Neonatal Jaundice," *Seminars in Liver Disease,* 8(2):148–162, May 1988.

Marchesini, et al., "Extinction and Absorption Coefficients and Scattering Phase Functions of Human Tissue *in vitro,*" *Applied Optics,* 28(12):2318–2324, Jun. 1989.

Millington et al., "CH. 3, The Skin in Depth," Ch. 4, Mechanical Properties of Skin" and Ch. 5, Mechanical, Thermal and Electrical Properties," *Skin,* 48–142, 1983.

Montagna et al., "Ch. 2, The Epidermis," and Ch. 3, Other Cells in the Epidermis," *The Structure and Function of Skin,* Third Edition, 18–95, 1974.

Nahas, G., "Spectrophotometric Determination of Hemoglobin and Oxyhemoglobin in Whole Hemolyzed Blood," *Science,* 113:723–724, Jun. 22, 1951.

(List continued on next page.)

OTHER PUBLICATIONS

Patterson, et al., "Quantitative Reflectance Spectrophotometry for the Non-Invasive Measurement of Photosensitizer Concentration in Tissue During Photodynamic Therapy," *SPIE* (vol. 1065) *Photodynamic Therapy: Mechanisms*, 115:122, 1989.

Pettit, et al., "Excimer Laser Induced Autofluorescence from Arteriosclerotic Human Arteries," *Lasers in Life Sciences*, 3(4):205–215, 1990.

Prahl, et al., "A Monte Carlo Model of Light Propagation in Tissue," *Dosimetry of Laser Radiation in Medicine and Biology*, SPIE series, IS5:102–111, 1988.

Prahl, S. A., "Light Transport in Tissue," Dissertation (UMI Dissertation Services), Degree Date 1988, printed 1992.

Rosen, et al., "Immediate Pigment Darkening: Visual and Reflectance Spectrophotometric Analysis of Action Spectrum," *Photochemistry and Photobiology*, 51(5):583–588, 1990.

Rubaltelli, et al., "The Effect of Light on Cutaneous Bilirubin," *Biol. Neonate*, 18:457, 1971.

Saidi, et al., "Optical Fiber Probe Monitor for Neonatal Bilirubinemia," *Proceedings of 11th Annual International Conference IEEE Engineering in Medicine and Biology Society*, Nov. 9–12, 1989.

Saidi, et al., "Monitoring Neonatal Bilirubinemia Using an "Optical patch," *Proceedings of SPIE–The International Society for Optical Engineering, Catheter–Based Medical Diagnostics and Imaging*, Los Angeles, CA, Jan. 18, 1990.

Saidi, I. S., "Light Transport in Neonatal Skin," Dissertation (UMI Dissertation Services), Degree Date 1990, Printed 1992.

Schumacher, R. E., "Noninvasive Measurements of Bilirubin in the Newborn," *Clinics in Perinatology*, 17(2):417–435, Jun. 1990.

Smith, et al., "Development of Dermal Connective Tissue in Human Embryonic and Fetal Skin," *Scanning Electron Microscopy*, IV:1745–1751, 1982.

Smith, et al., "Collagen Types I, III and V in Human Embryonic and Fetal Skin," *The American Journal of Anatomy*, 175:507–521, 1986.

Turkel, S. B., "Autopsy Findings Associated with Neonatal Hyperbilirubinemia," *Clinics in Perinatology*, 17(2):381–96, Jun. 1990.

Van De Hulst, H. C., "Isotropic Scattering, Finite Slabs," *Multiple Light Scattering Tables, Formulas, and Applications*, vol. 1, Ch. 9, 1980.

Van De Hulst, H. C., "Ch. 11, Results for the Henyey–Greenstein Phase Function," Ch. 13, Henyey–Greenstein Functions, Ch. 14, Results for Other Phase Functions, Ch. 16, Rayleigh Scattering, Ch. 17, Photon Optical Paths and Absorption Lines, and Ch. 20, Miscellaneous Applications, *Multiple Light Scattering Tables, Formulas, and Applications*, vol. 2, 1980.

Van Gemert, et al., "Skin Optics," *IEEE Transactions on Biomedical Engineering*, 36(12):1146–1154, Dec. 1989.

Welch, et al., "Practical Models for Light Distribution in Laser–Irradiated Tissue," *Lasers in Surgery and Medicine*, 6:488–493, 1987.

Wilson, et al., "The Effect of Photosensitizer Concentration in Tissue on the Penetration Depth of Photoactivating Light," *Lasers in Medical Science*, 1:235–244, 1986.

Wilson, et al., "Optical Reflectance and Transmittance Of Tissues: Principals and Applications," *IEEE Journal of Quantum Electronics*, 26(12):2186–2199, Dec. 1990.

Winkelman, et al., "Cutaneous Vascular Patterns in Studies with Injection Preparation and Alkaline Phosphatase Reaction," *Advances in Biology of Skin, Blood Vessels and Circulation*, eds. Montagna W. and Ellis, R. A., Pergamon Press Oxford, vol. 2, pp. 1–19, 1961.

Wukitsch, et al., "Pulse Oximetry: Analysis of Theory, Technology, and Practice," *Journal of Clinical Monitoring*, 4(4):290–301, Oct. 1988.

Yamanuchi, et al., "Transcutaneous Bilirubinometry: Preliminary Studies of Noninvasive Transcutaneous Bilirubin Meter in the Okayama National Hospital," *Pediatrics*, 65(2):195–202, Feb. 1980.

Symbols: Experimental Results
Lines: Monte Carlo Predictions

|  | m (460) | | | | | |
|---|---|---|---|---|---|---|
| yint (460) | 1.4 | 1.44 | 1.48 | 1.52 | 1.56 | 1.6 |
| -10 | 0.13043 | 0.15217 | 0.15217 | 0.15217 | 0.13043 | 0.13043 |
| -11 | 0.15217 | 0.15217 | 0.15217 | 0.15217 | 0.15217 | 0.13043 |
| -12 | 0.10870 | 0.15217 | 0.15217 | 0.15217 | 0.15217 | 0.15217 |
| -13 | 0.10870 | 0.10870 | 0.15217 | 0.15217 | 0.15217 | 0.15217 |
| -14 | -0.10870 | 0.10870 | 0.10870 | 0.15217 | 0.15217 | 0.15217 |
| -15 | -0.10870 | 0.10870 | 0.10870 | 0.10870 | 0.15217 | 0.19565 |
| -16 | -0.15217 | -0.10870 | 0.10870 | 0.10870 | 0.10870 | 0.19565 |
| -17 | -0.15217 | -0.15217 | -0.10870 | 0.10870 | 0.10870 | 0.19565 |
| -18 | -0.08695 | -0.15217 | -0.19565 | -0.10870 | 0.10870 | 0.10870 |
| -19 | -0.08695 | -0.08695 | -0.19565 | -0.19565 | -0.15217 | 0.10870 |
| -20 | -0.04347 | -0.08695 | -0.10870 | -0.19565 | -0.19565 | -0.15217 |

CASE 1
$r' < (R_{out} - r)$

All the light emitted in this annulus is collected.

CASE 2
$(R_{out} - r) < r' < (R_{out} + r)$

A fraction of the light delivered at this radial distance is collected.

CASE 3
$r' > (R_{out} + r)$

None of the light delivered at this radial distance is collected.

+ 600 μm skin thickness
O 900 μm skin thickness
◇ 1200 μm skin thickness

METHOD AND APPARATUS FOR OPTICAL MEASUREMENT OF BILIRUBIN IN TISSUE

BACKGROUND AND SUMMARY OF THE INVENTION

1.1 Background

The invention relates to transcutaneous optical measurement of blood components and contaminants, particularly, transcutaneous measurement of hyperbilirubinemia in neonates.

1.1.1 Reflectance Spectroscopy

Throughout this disclosure, material appearing in brackets refers to the references listed in Appendix D.

There has been an increasing interest in the use of low level light as a diagnostic tool in medicine [Andreozi 1987, Kato 1985, Kopola 1990, Pettit 1990, Richards-Kortum 1990, Wukitsch 1988, Yamanuchi 1980]. This concept has become more appealing with the simultaneous development of appropriate and inexpensive light sources, detection devices, and optical fibers that allow for minimal invasiveness. Such application of light depends on the measurement of reflection or fluorescence and aims to qualitatively or quantitatively assess the presence of a substance in the tissue, or determine the pathological state of the tissue. Optical transducers of non-optical properties, such as pressure or pH, can be designed when the optical fibers ends are combined with flexible membranes or chemicals [Katzir 1988].

Light diffusely reflected from a tissue has traveled within the tissue, and non-invasively provides rapid quantitative measurements of pigments within the tissue. The reflection of light from a tissue is dependent on the ratio of the scattering coefficient to the absorption coefficient within the tissue. Therefore, the absorbance within a tissue can be delineated from a single reflection measurement if the scattering properties of the tissue are known. Empirically developed algorithms for the interpretation of reflected spectra are suitable when the concentration of only one pigment concentration is varied, and the scattering properties of the tissue are fixed. These algorithms are vulnerable to errors as the scattering coefficient, or the absorption coefficient of other pigments in the tissue vary between tissue samples.

1.1.2 Hyperbilirubinemia

Bilirubin is produced from the breakdown of hemoglobin in red blood cells. Under normal conditions the bilirubin is conjugated by glucoronyl transferase, an enzyme present in the liver, and then excreted through the biliary system. Hyperbilirubinemia describes the state where there is excessive bilirubin in the body.

Newborn infants, and particularly premature ones, are susceptible to hyperbilirubinemia. Often this is due to the lack of functioning glucoronyl transferase enzyme in their liver, or excessive red blood cell breakdown associated with erythroblastosis fetalis [Maisels 1988]. Extreme hyperbilirubinemia places neonates at risk of kernicterus, the leakage of bilirubin into the basal ganglia in the brain, and potentially causes neuronal retardation. For this reason, it is desirable to regularly monitor the bilirubin concentrations in the body.

Bilirubin from the blood stains the skin (cutaneous bilirubin) in addition to other tissues of the body. Jaundice refers to the condition when the bilirubin is visible in the skin and sclera. The kinetics of transfer of bilirubin from the blood to the skin are not well understood, but appear to be dependent on various physiological factors in addition to serum bilirubin concentration.

1.1.3 Transcutaneous Bilirubinometry

Non-invasive measurements of the bilirubin concentration in the skin may eliminate the need to draw blood (serum) samples from neonares for bilirubin analysis. Numerous attempts have been made to measure cutaneous bilirubin non-invasively. These attempts include the development of visual reference standards, and more recently transcutaneous reflectance spectroscopy [Hannemann 1978, Hannemann 1982, Hegyi 1986, Kenny 1984, Schumacher 1990, Yamanuchi 1980]. FIG. 1 shows the absorption spectra of bilirubin, oxidized blood, and melanin, the dominant absorbers in the skin. The concentration of these pigments in the skin are highly variable. Since these three pigments have very distinct absorption spectra, the absorption due to cutaneous bilirubin should be determinable by correct analysis of the reflectance spectra.

Reflectance bilirubinometers have obtained reasonable correlations between bilirubin levels determined transcutaneously and serum bilirubin concentrations in homogeneous patient populations, but have failed to give satisfactory correlations when used over a heterogeneous population [Hannemann 1982]. Since patient populations are rarely homogeneous, transcutaneous bilirubinometers have not been widely accepted clinically [Schumacher 1990].

The key to correct interpretation of cutaneous reflectance spectra, is to understand how the measured reflectance is affected by: (i) pigments in different locations of the skin, (ii) in skin with different scattering properties, and (iii) with different combinations of other absorbers, such as blood and melanin.

1.2 Summary Of Invention

The present invention largely avoids the above-noted discrepancies of prior art reflectance bilirubinometers by providing for the correction of errors in the reflectance measurement of bilirubin due to, for example, gestational maturity, melanin content and blood content of the tissue such as skin of an individual being tested.

More specifically, the present invention contemplates illuminating the skin surface or other tissue of an individual under test, and detecting a spectrum of reflected light. Various portions of the spectrum are analyzed to determine gestational maturity of the tissue, as well as melanin and blood content of the tissue, in addition to an uncorrected measurement of bilirubin content. Then, calculations are performed using these four quantities to provide a corrected concentration of bilirubin.

As a by-product of the present invention, measurement of gestational maturity of the skin of neonates is provided.

More specifically, reflected blue light is used to determine uncorrected absorption due to bilirubin. Then, reflected red to infrared light is used to determine absorption due to maturity-dependent optical properties of the skin, reflected red light is used to determine the amount of absorption due to melanin in the skin, and reflected yellow-orange light is used to measure absorption due to blood in the skin. Once the optical absorption due to blood melanin and maturity-dependent optical properties of the skin are measured, the contribution of these factors to the absorption of blue light can be calculated and subtracted from the uncorrected absorption of blue light to yield absorption due to bilirubin alone. Once this is known, the concentration of bilirubin in the skin can be calculated.

The location and quantity of pigments, and the scattering properties of the skin, are important considerations for correct reflectance analysis. Therefore, the architecture and optical properties of neonatal skin have to be determined, and a model developed. The physical bases and mathematical descriptions of optical properties are explained in Appendix A. FIG. 2 shows a histological cross section of a neonatal skin sample. The cross section reveals skin surface 101, epidermis 102, dermis 103 and hypodermis 104. In accordance with the present invention a skin model is developed. Epidermis 102 contains all the melanin, and is modelled as an absorbing layer. Dermis 103 includes collagen fiber bundles 106. Interspersed with collagen fiber bundles 106 are fibroblasts that maintain bundles 106. Blood is present in plexi that branch into a capillary network and feed the dermis. Dermis 103 is modelled as predominantly a scattering medium with some absorption. The blood and billirubin are modelled as being diffusely present throughout dermis 103. Hypodermis 104 is composed primarily of collagen matrix mixed with fat cells. Hypodermis 104 shares its blood supply with dermis 103, and is modelled as an extension of dermis 103. This model has been developed based on histological evidence, and its suitability verified by optical property and Monte Carlo data presented in sections 2, 3, and 4. The model accounts for the melanin in the skin which is located in the epidermis 102, the topmost layer of the skin, and for the dermis 103 which is primarily composed of a collagen fiber bundle matrix and is maintained by interspersed fibroblasts.

This disclosure is separated into sections in order to more clearly describe the scope of the invention. In addition, several Appendices are included for completeness.

In section 2, the optical properties of neonatal dermis are measured in vitro, and the results are reported. A method to determine the optical properties from reflectance and transmission measurements performed in an integrating sphere is discussed. The collagen fiber bundle diameters and concentration are measured in representative skin samples, and Mie theory of scattering is used to relate the number of collagen fiber bundles per unit volume and their size distribution to the dermal scattering.

In section 3, reflectance measurements by distant and surface detectors are discussed. An experimental method and Monte Carlo computer simulations to determine the collection efficiency of a surface optical transducer are presented. The model can be used to systematically study how variations in the optical properties and in the geometry of the transducer affect the collection efficiency of a transducer under design. The effect of epidermal melanin on the measured reflectance is also analyzed, and a method to use the measured reflectance to determine the absorption in a tissue of known scattering coefficient is presented.

In section 4, variations in scattering properties, melanin content, blood depth, skin thickness, and cutaneous bilirubin in neonatal skin samples are discussed. The effect of these variations on the measured reflectance spectra are analyzed. A method to determine the skin scattering and the melanin content in vivo is presented.

In section 5, the optical model of skin, and the considerations of how skin scattering, bilirubin, blood, and melanin affect reflectance are combined to develop an algorithm to determine cutaneous bilirubin in accordance with the present invention. Monte Carlo simulations are used to evaluate the bilirubin algorithm, and compare it to traditional analysis of measured reflectance without consideration of radiative transport theory. The algorithm developed is applied to clinical reflectance measurements obtained in neonates, and the results presented.

In Appendix A, the coefficients which describe light interaction with tissue are presented, and light transport in tissue is discussed. In Appendix B, a convolution procedure to determine the optical patch collection efficiency from Monte Carlo data is presented, and this procedure is implemented in a computer program. In Appendix C, the effect of skin thickness on the measure reflectance spectra is analyzed. Appendix D lists the references appearing throughout this patent disclosure, as Appendix E presents a source code listing of the algorithm of the present invention.

DETAILED DESCRIPTION OF THE INVENTION

Section 2

Figure 1:
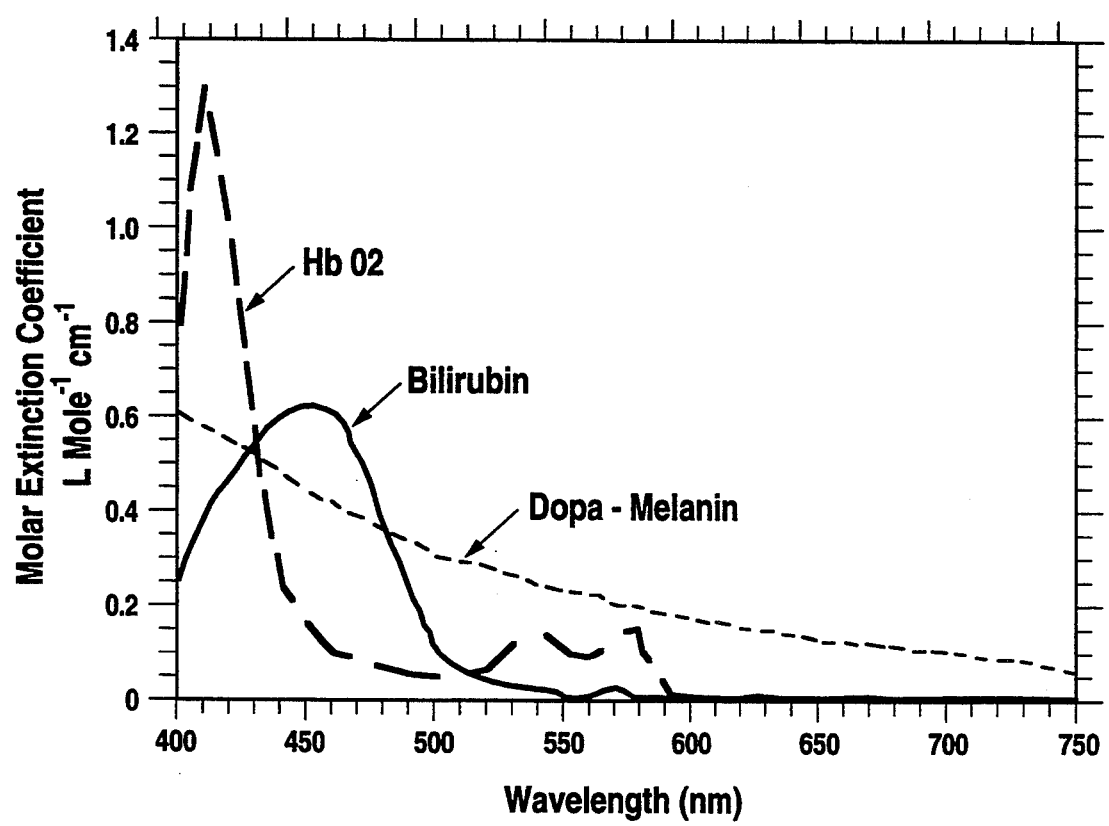
FIG. 1 is a graph of the absorption spectra of bilirubin, oxygenated hemoglobin and dopa-melanin.
Figure 2:
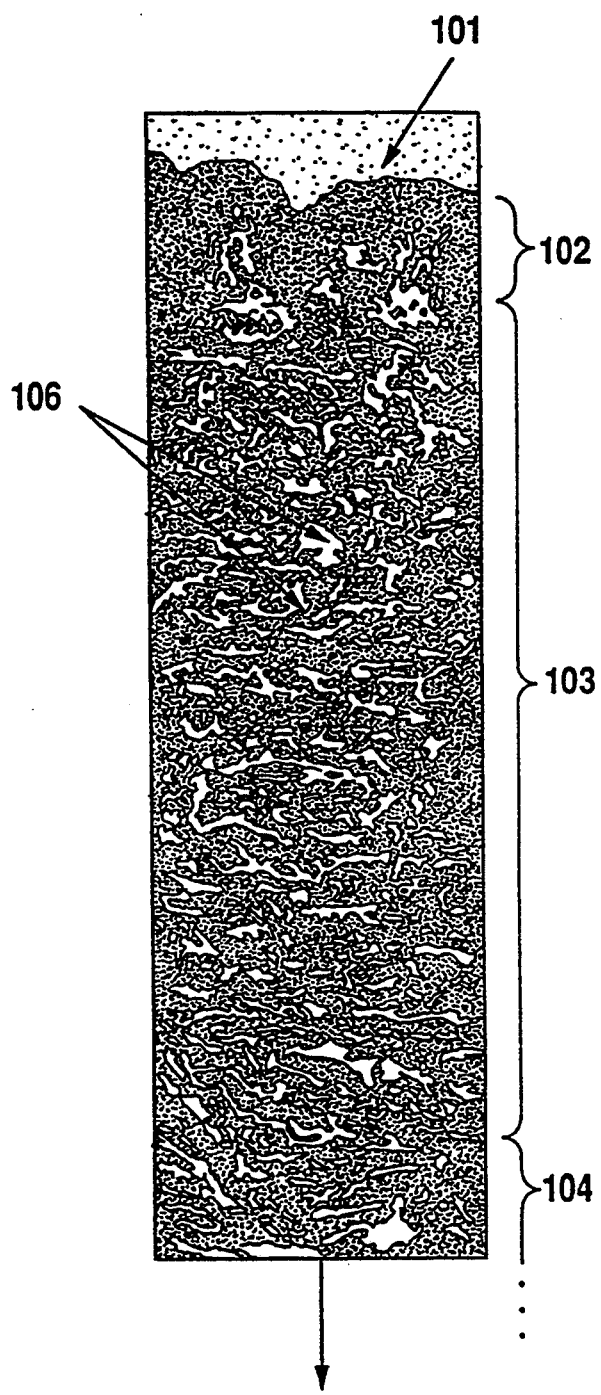
FIG. 2 is a histological section of neo-natal skin.

Optical Properties of Neonatal Skin 2.1 Introduction

The optical interaction coefficients, or optical properties, of tissues describe the behavior of light in tissue. They are the absorption coefficient, $\mu_a$, the scattering coefficient, $\mu_s$, and the anisotropy, g (See Appendix A). The combination $\mu_s(1-g)$ is called the reduced scattering coefficient, and it describes the effective amount of scattering in a tissue. Knowledge of the optical properties is important for the development of diagnostic and therapeutic applications of light to tissue.

For diagnostic applications, knowledge of the optical properties, and of radiative transport theory, enable the development of fundamentally correct diagnostic algorithms that can accommodate the inhomogeneities of tissue samples. The importance of knowing the optical properties of skin for the development of transcutaneous reflectance spectroscopy will be discussed further in sections 3, 4 and 5. Furthermore, the optical properties are desired for the development of therapeutic applications of light, since they dictate the dosimetry of light in the tissue.

The optical properties of adult skin have been studied in the past [Jacques 1987b, Prahl 1989, Anderson 1981, van Gemert 1989, Marchesini 1989, Jacques 1990], but those of neonatal skin samples have not been determined. In this chapter the absorption and scattering properties of neonatal skin are determined, and the relationship between the scattering coefficients and gestational maturity of the infant is studied. The microstructure of the dermis is studied quantitatively. The measured scattering coefficients are related to a combination of Mie theory scattering by the collagen fiber bundles in the dermis, and Rayleigh scattering by smaller particles.

The measured optical coefficients determined in this section are utilized in subsequent sections to study how variables in the skin, such as absorption, maturity, and thickness, influence the measured reflectance spectra. The optical interaction coefficients of neonatal skin are an essential component of the method of the present invention developed to transcutaneously determine the cutaneous bilirubin concentration.

2.2 Materials And Methods

2.2.1 Tissue Samples

Twenty abdominal skin samples were obtained from 15 pediatric autopsies. The estimated gestational age of the subjects varied from 19 weeks to full term ($\sim$38 weeks gestation), and the age of the newborn at death varied from zero to 5 months old. The samples were obtained from a racially heterogeneous population. The samples were excised during autopsy, and sealed in an air-tight bag to maintain their moisture content, but without addition of saline to avoid swelling. The skin was then separated from the subcutaneous tissue with a scalpel and forceps, and placed between glass microscope slides of known thickness that were separated by calibrated spacers of the same thickness as the tissue. This method enforced a uniform tissue thickness with a well defined air/glass/tissue interface, and prevented tissue desiccation. The thickness of the sample, d, was verified by measurements with digital calipers of the glass and tissue sandwich. The average thickness of the skin was 888$\pm$301 $\mu$m (mean$\pm$S.D., n=20), and the average area of the skin sample was approximately 1.5 cm$^2$. The two surfaces of the skin will be referred to as the epidermal and the subcutaneous sides. Experiments were conducted twice, first irradiating the epidermal surface and then irradiating the subcutaneous surface with light. Melanin is present only on the epidermal side, so if melanin content is significant, the epidermal exposure would suffer more than the subcutaneous exposure. The influence of epidermal melanin pigmentation is assessed by determining if the optical properties obtained from either exposure differ markedly. In twelve of the twenty subjects, there was no significant difference in measurements using epidermal versus subcutaneous exposure, implying negligible melanin content.

A separate study of the water content of the skin samples indicated that typical hydration was 65$\pm$4% (mean$\pm$S.D., n=10), based on the difference in mass between fresh and oven-dried samples.

2.2.2 Reflectance And Transmission Measurements

Figure 3A:
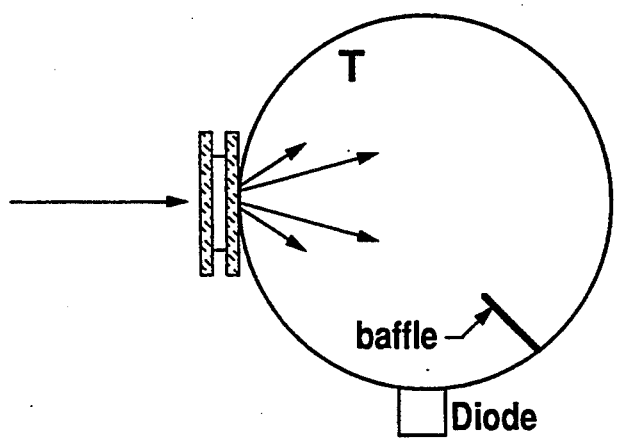
FIG. 3A and 3B are of an integrating sphere spectrophotometer used to measure the diffuse reflection and transmission of tissue samples, in accordance with the present invention.
Figure 3B:
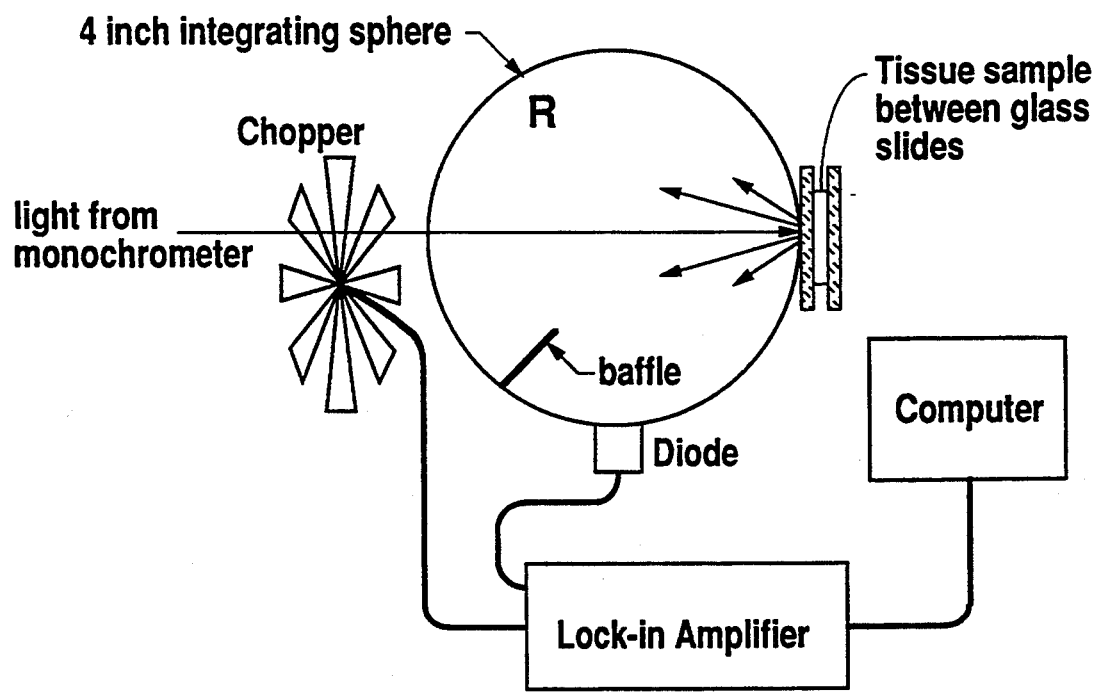

The total reflectance, $R_t$, equals the diffuse reflectance, $R_d$, that is backscattered by the tissue plus the specular reflectance, $R_{sp}$, from the front air/glass/tissue interface of the sample. The total transmission, $T_t$, equals the diffusely scattered transmission, $T_d$, plus the unscattered collimated transmission, $T_c$. The optical experiments measured $R_d$ and $T_t$ using an integrating sphere as shown in FIG. 3A, and measured $R_d$ using an integrating sphere as shown in FIG. 3B.

The integrating sphere (Labsphere Inc., North Sutton, N.H.) had a 4-inch diameter and an inner wall reflectivity of 98.6% (based on unpublished experiments). The measurements in laboratory units (mA of detector diode current) of the diffuse reflectance, $M_R$, and total transmission, $M_T$, of the skin samples were recorded when the sample was placed at the reflectance and transmission port respectively. The specular reflectance, $R_{sp}$, from the front air/glass/tissue interface escaped the sphere through the entrance port and was not measured. A small background signal due to stray light, $M_o$, was measured when nothing was placed at either port and light simply entered the front port and exited at the back port. A calibration measurement, $M_{std}$, of diffuse reflectance from a standard plate of Spectralon TM with a known reflectance of 99.4% (Labsphere Inc., North Sutton, N.H.) was also recorded. Spectrometric data were obtained using a Xenon tube light source (Model-77822, Oriel Corp., Stamford, Conn.) and a 5-nm bandwidth grating monochrometer (Model-77250, Oriel Corp.) that was manually scanned between 400 and 750 nm in increments of 10 nm.

2.2.3 Data Analysis

The total diffuse reflectance, $R_d$, of the skin sample, from both the epidermal and dermal sides, was calculated:

$$R_d = \frac{M_R - M_o}{M_{std} - M_o} (0.994) \tag{2-1}$$

The total transmission, $T_t$, of light through the skin, was calculated:

$$T_t = \frac{M_t - M_o}{M_{std} - M_o} \tag{2.2}$$

Reflectance and transmission defined by Equations 2-1 and 2-2 and based on measurements performed in an integrating sphere are slightly lower than true values. First, the sphere throughput efficiency is less when a lossy sample is at a port than when the calibrating standard (SPECTRALON®) is at the port. Secondly, additional losses occur due to the lateral diffusion of light in the tissue sample and in the glass slide beyond the edges of the sphere port. This effect is accentuated when a thicker glass slide is placed between the tissue sample and the integrating sphere port.

To correct for these losses, an experiment to determine the correction factors was performed. Solutions with known optical properties were prepared from fixed concentrations of intralipid and trypan blue. The optical properties of the intralipid and trypan blue were determined by collimated transmission, total reflectance, and added absorber measurements [Wilson 1986, Cheong 1990]. The true total reflectance and transmittance from a known thickness of these solutions were calculated using an 8-flux adding-doubling routine (explained in the next paragraph). Samples from these solutions were also placed in cuvettes, and their reflectance and transmittance measured with the integrating sphere recorded. The correction factors were then derived by relating the measured reflectance and transmittance values to the true values predicted by adding-doubling. The expressions for calculating the true reflectance and transmittance from the measured values are:

$$\text{corrected } R_d = R_d \times 1.11 \times (1.106 + 1.716 \, \delta - 5.044 \, \delta^2) \tag{2-3a}$$

and $$\text{corrected } T_t = T_t \times 1.111 \tag{2-3b}$$

where penetration depth, $\delta$, is defined as:

$$\delta = \frac{1}{\sqrt{3\mu_a(\mu_a + \mu_s')}} \qquad (2.4)$$

and where $\mu_a$ and $\mu_s'$ were calculated by an iterative 8-flux inverse adding-doubling calculation of the uncorrected reflectance and transmittance.

The corrected values of diffuse reflectance, $R_d$, total transmission, $T_t$, for each wavelength, and thickness, d, were then analyzed using an iterative 8-flux inverse adding-doubling routine by Scott Prahl, Department of Electrical Engineering, University of Texas at Austin [Prahl 1989]. The adding-doubling method was originally developed by van de Hulst to calculate the reflectance and transmission of a slab of known thickness [van de Hulst 1980]. The transmission and reflectance from a very thin slab is calculated by assuming knowledge of a single-scattering event, and the results are used to predict the behavior of successively doubled slab thicknesses until the final sample thickness is reached, yielding the reflectance and transmission of the tissue sample. The iterative inverse routine (an 8-flux calculation [Prahl 1989]) yielded a unique pair of $\mu_a$ and $\mu_s(1-g)$ values from a pair of $R_d$ and $T_t$ measurements at each wavelength for a sample of known thickness. The errors in deduced optical properties are less than 10% for accurate measurements of $R_d$ and $T_t$ [Saidi 1990]. Samples were optically too thick at wavelengths below 450 nm to allow sufficient transmission for accurate analysis. Therefore, no results are reported at these shorter wavelengths.

2.2.4 Mistology

Histological samples were obtained from four representative skin samples, and were stained with H&E and Masson's trichrome stains. The collagen fiber bundle content of the skin samples was measured using a videometric image analysis system (VT150, American Innovision Inc., San Diego, Calif.). With the image analyzer, lines perpendicular to the epidermal surface were projected on each image captured for a histological sample. The numbers and diameters of the collagen fiber bundles were measured along each of these projections, and a collagen concentration coefficient was calculated, defined as the number of collagen fiber bundles per mm. The collagen concentration coefficient was used to calculate the concentration of collagen fiber bundles for the histological sample. The mean collagen fiber bundle diameter along each projection was also measured.

2.3 Results

The results are presented first in terms of the changes in optical properties at a single wavelength as a function of gestational age. Secondly, the wavelength dependence of optical properties are presented for three representative ages. Finally, the ultrastructural measurements of fiber bundle size and concentration are presented.

Figure 4:
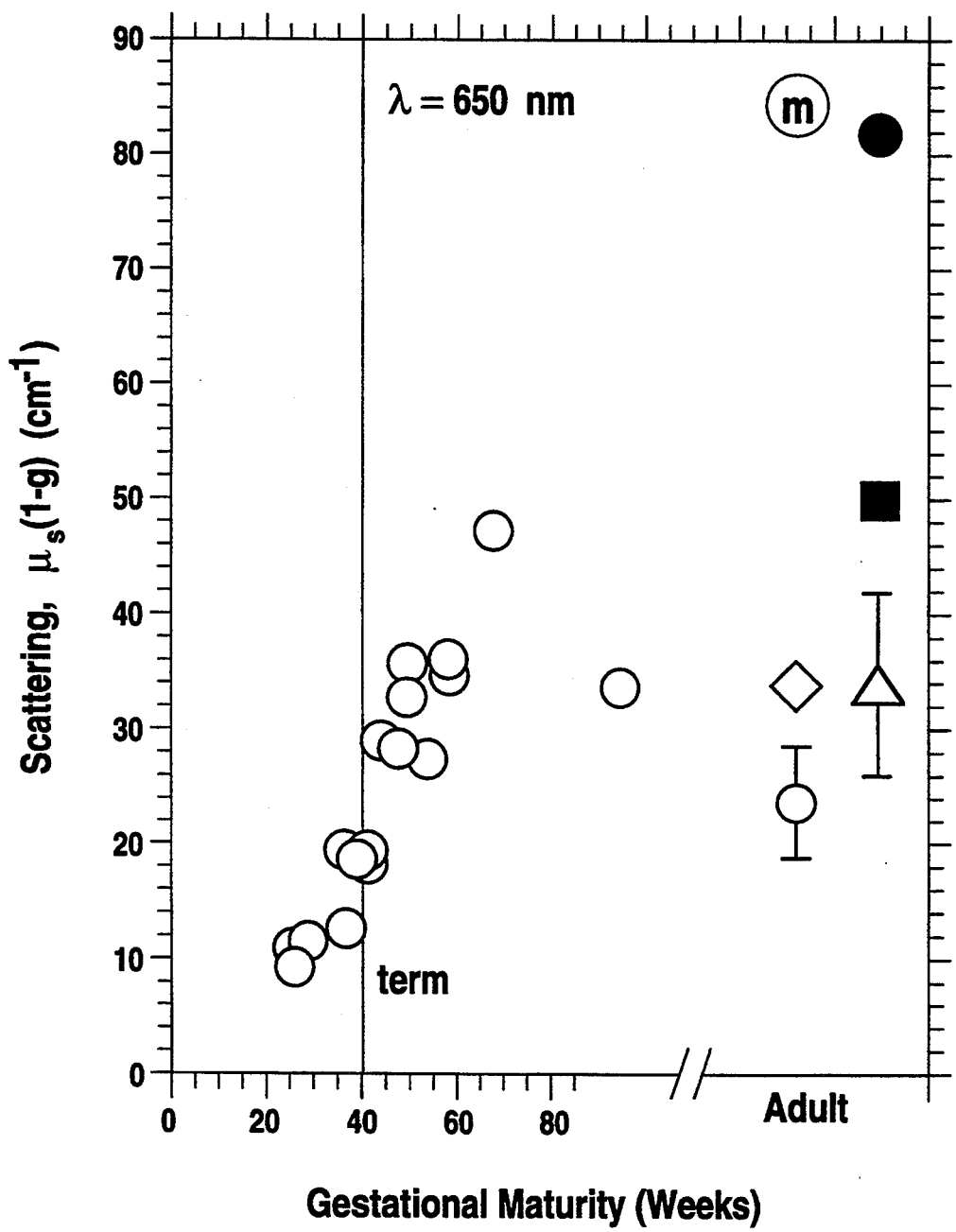
FIG. 4 is a graph of reduced scattering coefficient as a function of gestational maturity.

The scattering coefficient at 650 nm increased linearly with age, as shown in FIG. 4. Age is defined as the estimated gestational period plus the postnatal period before death. Similar relationships were observed for the scattering coefficient at other wavelengths (not shown). Also plotted are the $\mu_s(1-g)$ values for adult skin based on 3 samples included in this study and on reported values in the literature (see Section 2.4). The scattering of neonatal skin at about 60 weeks is comparable to the scattering of adult skin. There is considerable variation in $\mu_s(1-g)$ amongst adult skin samples.

Figure 5:
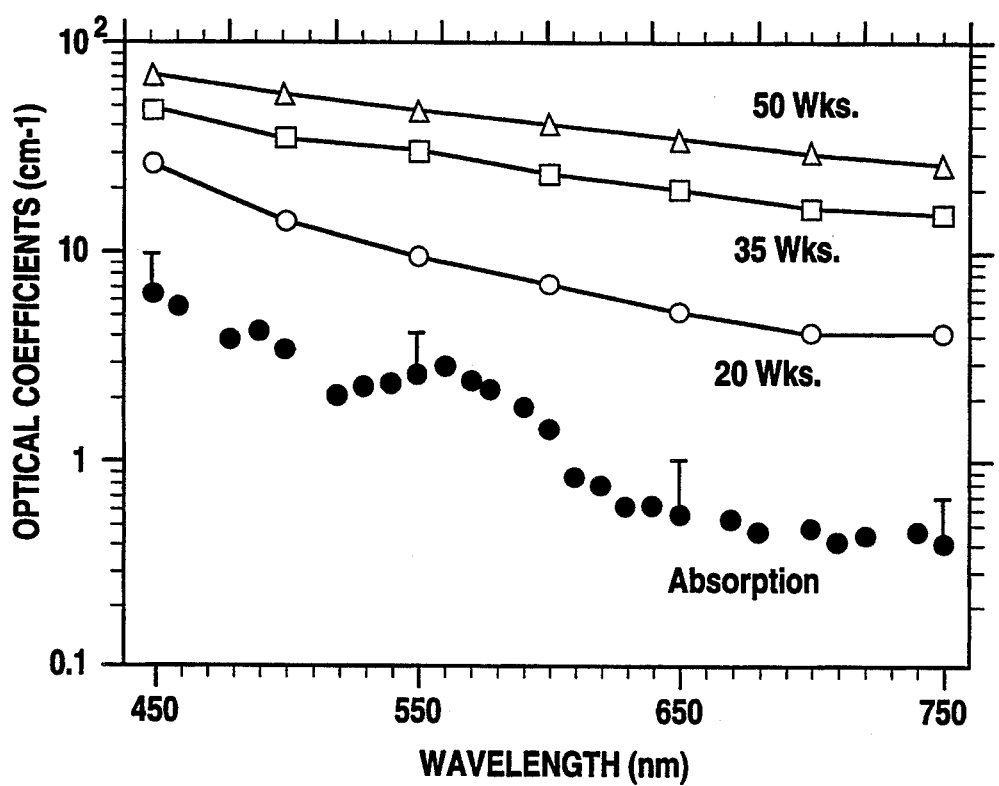
FIG. 5 is a graph of the absorption and scattering coefficients determined for neonatal skin samples of varying gestational maturity.

The wavelength dependence of the absorption and reduced scattering coefficients, $\mu_a$ and $\mu_s(1-g)$, for 12 non-pigmented neonatal skins are plotted in FIG. 5. The optical properties differed by less than 10% when calculated from measurements which delivered light to either the epidermal or subcutaneous sides of the skin. Therefore, the effect of melanin pigmentation was negligible. The reduced scattering coefficients for three ages, 20, 35, and 50 weeks, were determined by interpolation of the $\mu_s(1-g)$ data as a function of age (see FIG. 4). In FIG. 4, results from the present study are shown with open circles, and results reported in the literature are shown with other symbols. Scattering is stronger at shorter wavelengths. Scattering increases with age, apparently as collagen fiber bundles increase in size and concentration, as discussed below. The mean values of $\mu_a$ for all subjects versus wavelength are also shown, along with standard deviations at selected wavelengths. There was no obvious dependence of $\mu_a$ on age.

A linear fit of the $\mu_s(1-g)$ data as a function of age (similar to that in FIG. 4) performed at 50-nm wavelength intervals between 450 and 750 nm yields a y-intercept, $y_{int}(\lambda)$, and a slope, $m(\lambda)$, for each wavelength. The scattering coefficient at a specified gestational maturity, and wavelength is equal to:

$$\mu_s(1-g)(\lambda) = y_{int}(\lambda) + m(\lambda)\,maturity \qquad (2\text{-}5)$$

where $\mu_s(1-g)$ is expressed in $cm^{-1}$, and maturity is expressed in weeks. The empirical fit of the y-intercept, $Y_{int}$, as a function of wavelength is:

$$y_{int}(\lambda) = 22.5 - 0.14267928\,\lambda + 0.000129357\,\lambda^2 \qquad (2\text{-}6)$$

and the fit of the slope, m, is:

$$m(\lambda) = 2.978 - 0.0029985\,\lambda \qquad (2\text{-}7)$$

where $\lambda$ is the wavelength expressed in nm.

The absorption coefficient of the skin did not change predictably with gestational age. A characteristic absorption spectrum for hemoglobin was observed in the 500–600 nm range for most (7 of 9) stillbirths, while not observed in the $\mu_a$ spectra of any of the neonates that died postnatally. A measure of the absorption coefficient due to hemoglobin was calculated by subtracting the $\mu_a$ at 650 nm where hemoglobin absorption is very low, from the $\mu_a$ at 585 nm where there is significant hemoglobin absorption. This calculated difference, $\Delta\mu_a\,585\text{-}650$, attributed to hemoglobin was 4.4 ($\pm 3.8$ SD, $n=7$) $cm^{-1}$ for stillbirths and 1.6 ($\pm 1.4$ SD, $n=10$) $cm^{-1}$ for the neonates that died postnatally. This implies that the stillbirths contained a higher concentration of blood in their skin than did the liveborn neonates.

The average absorption coefficient of the skin, shown in FIG. 5 varied significantly in the 400 to 600-nm range due to variation in bilirubin and blood content in the in vitro skin samples. A fit of the absorption coefficient measured above 620 nm is:

$$\mu_{a\,skin} = 5\,exp(-0.0035\,\lambda)(cm^{-1}) \qquad (2\text{-}8)$$

Figure 6:
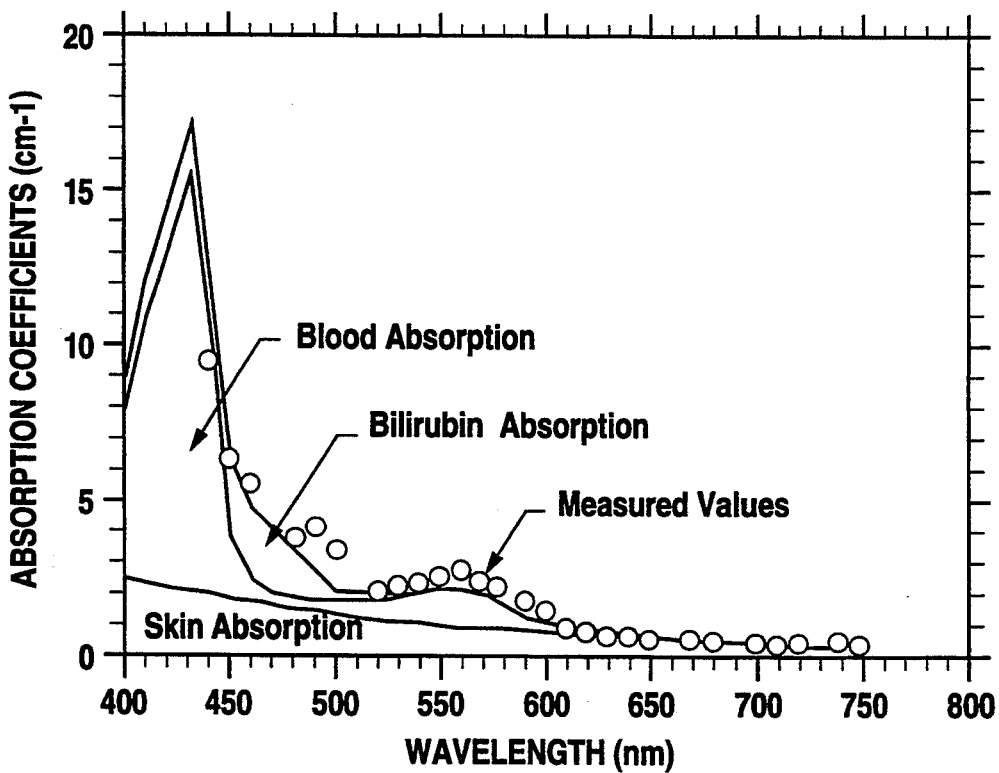
FIG. 6 is a graph of the average absorption coefficient for neonatal skin as a function of wavelength.

FIG. 6 shows the approximate relative contributions of skin, blood, and bilirubin absorption to the total absorption coefficient of skin. The expression for skin absorption, $\mu_{a\,skin}$ as a function of wavelength, $\lambda$ (in nm), is:

$$\mu_{a\,skin} = 27 \exp(-0.006 \lambda)(cm^{-1}) \quad (2\text{-}9)$$

This expression for $\mu_{a\,skin}$ was determined in section 5, and fits the measured absorption coefficients well at wavelengths over 620 nm where the absorption due to blood and bilirubin become negligible. As discussed in section 5.5, this expression for $\mu_a$ is also consistent with the shorter wavelength spectrum in vivo.

2.4 Discussion

2.4.1 Optical Properties

In the epidermis, it is the absorption due to melanin which restricts the penetration of light. In the dermis, however, there is little absorption, except by bilirubin and hemoglobin, so that scattering is an important optical parameter that strongly influences the penetration of light. The scattering coefficients of the epidermis and dermis are similar, while the absorption coefficients can differ [van Gemerr 1989]. By selecting non-pigmented skin samples, in which calculated optical properties were the same (<10% difference) regardless of whether the radiation was delivered to either the epidermal or subcutaneous sides, the essential optical properties of the skin were determined with minimal effect of melanin. The optical absorption spectrum of 0-melanin is known [Kollias 1985, Jacques 1991], and so melanin pigmentation can be quantitatively added to any computational models used to predict the penetration of light in variably pigmented infants.

Adult $\mu_s(1\text{-}g)$ data cited in the literature are included in FIG. 4 (using symbols other than unfilled circles) for comparison with the neonatal values. There is considerable variation in reported values for adult skin.

2.4.2 Hemoglobin Absorption

The vascular development of the skin is defined during the first trimester of gestation [Johnson 1989]. Therefore, all skin samples in our study were expected to have well established vascular supplies, and this was confirmed by microscopic analysis of the histological sections. There was an increase in absorption due to hemoglobin in the skin of stillborns relative to the skin of neonares that expired postnatally.

Fetuses that expire are suspended in amniotic fluid until they are delivered. Blood continues to perfuse the tissues, and intrauterine cutaneous autolysis begins soon after expiration. This can lead to extravasation of the red blood cells, and hemolysis of these cells can lead to generalized dissemination of the hemoglobin in the skin. Infants that die postnatally, however, are usually laid in a supine position which causes pooling of the blood in the back. The abdominal skin samples obtained did not contain significant quantities of hemoglobin that had perfused the skin.

2.4.3 Scattering vs. Gestational Maturity

The most notable optical property that changed with gestational maturity is the reduced scattering coefficient, $\mu_s(1\text{-}g)$. This parameter is sensitive to changes in the skin structural composition that accompany gestational maturation. Collagen fiber bundles are the most important scattering elements in the dermis (as discussed in the next section), and the increase in scattering with gestational age may be explained by the accompanying increase in the size and concentration of the collagen fiber bundles. Studies with scanning electron microscopy and immunogold labeling have revealed that there is an increase in the ratio of type I to type III collagen with gestational age [Smith 1982, Smith 1987, Burgeson 1987]. As gestation progresses, there is an increase in the concentration of collagen fibers, more collagen fibers are associated in fiber bundles, and these bundles have thicker diameters [Smith 1982, Smith 1987, Burgeson 1987]. Quantitative video image analysis of the histological samples confirmed that both the number of the collagen fiber bundles, and the size of these fibers increase with gestational age.

2.4.4 Mie And Rayleigh Light Scattering In Dermis

A description of dermal scattering based on classical theory light scattering by cylinders and small particles is presented. Such a description bridges between the macroscopic scattering observed clinically and measured experimentally, and the theory of light scattering by ideal structures similar to the ultrastructural components of dermis.

We consider both Mie scattering by structures similar in size to the wavelength of light (i.e., collagen fibrils and bundles) and non-Mie scattering by structures that are small in comparison to the wavelength of light. Mie scattering is treated by the Mie theory for scattering by cylinders [Bohren 1983], and has an anisotropic scattering profile (g>0). Non-Mie scattering is treated as Rayleigh scattering which has a $\lambda^{-4}$ wavelength dependence and on the average has an isotropic scattering profile (g=0).

Figure 7A:
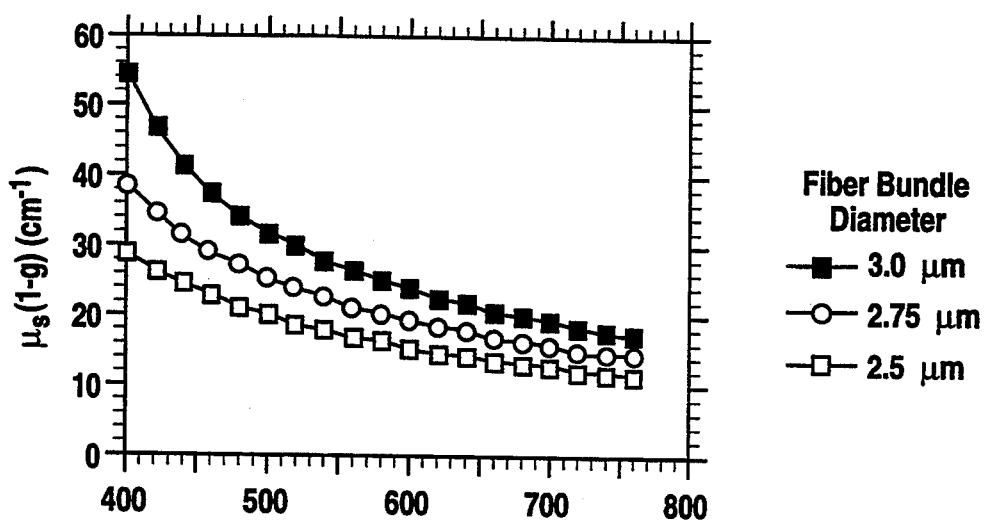
FIGS. 7A, B and C are graphs of the reduced scattering coefficient as a function of wavelength predicted by Mei theory for various collagen fiber bundle characteristics.
Figure 7B:
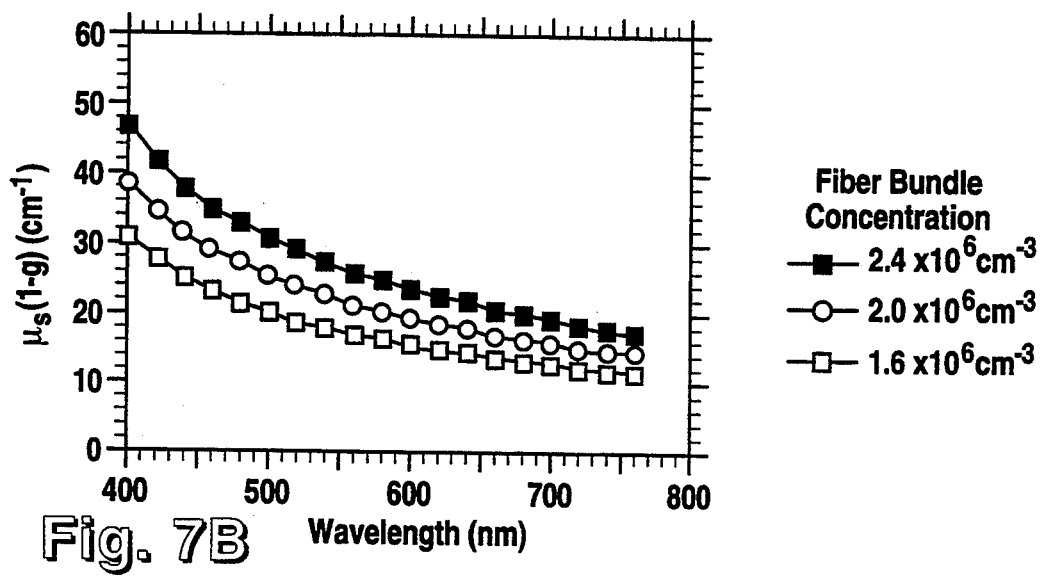
Figure 7C:
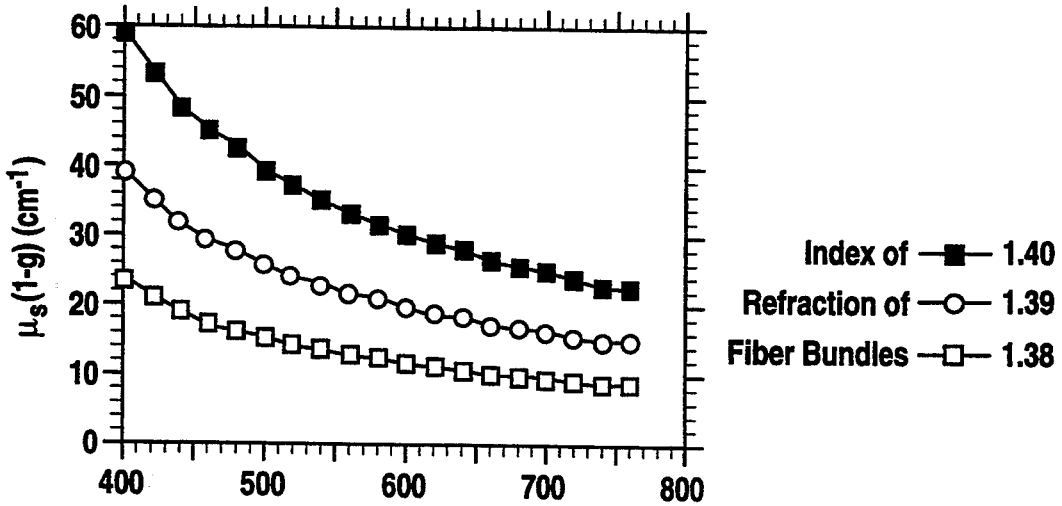

The dermis is primarily composed of collagen fiber bundles. Although oriented in a variable manner in the dermis, the collagen fiber bundles are nevertheless dominated by a general orientation parallel to the skin surface [Montagna 1974, Smith 1986]. Mie theory can model these bundles as infinitely long cylinders and predict the scattering from each fiber [Bohren 1983]. The theory predicts the scattering coefficient, $\mu_s$, and the angular dependence of scattering, $p(\theta)$. The anisotropy, g, was calculated based on $p(\theta)$ (see Equation A-7 in Appendix A). The scattering in a medium with suspended particles is determined by the size of the particles, their concentration in the medium, and the index of refraction mismatch between the medium and the particles. The effect of these three parameters on the scattering magnitude and wavelength dependence is illustrated in FIGS. 7a, 7b and 7c. In each sub-figure the reduced scattering, $\mu_s(1\text{-}g)$, is predicted by Mie theory for collagen fiber bundles oriented parallel to the skin surface, at a concentration of $2.5 \times 10^6$ per $cm^3$ where each fiber bundle has a diameter of 2.75 $\mu m$ and an assumed index of refraction of 1.390. The index of refraction of the medium surrounding the fiber bundles is assumed to be a lower value, 1.346. These choices of the refractive indices are explained in the next paragraph.

The index of refraction of the scattering particles and of the surrounding medium affect the scattering magnitude and wavelength dependence. Both the ratio of the index of refraction of a particle relative to that of the surrounding medium, and the absolute values of the indices of refraction are important determinants of the scattering cross section of the particle. Assignments of 1.390 and 1.346 for the indices of refraction of the particles and of the surrounding media respectively will let the reduced scattering profile predicted by Mie theory in the above model match the wavelength dependence of 35-week gestational maturity skin. Other indices-of-refraction pairs may also be chosen to match the 35-week gestational maturity scattering profile. Indices of refraction of 1.390 and 1.346 are believed to be realistic for hydroxylated collagen and for extracellular fluid respectively.

The values of fiber bundle size, concentration, and indices of refraction assumed in FIGS. 7A, 7B and 7C successfully model the average magnitude and wavelength dependence of scattering in the dermis of a fetus at about 35 weeks gestational age (see FIG. 5). In FIGS. 7A, B, and C, the concentration, diameter, and index of refraction, respectively, of the fiber bundles are varied above and below the average values. The scattering increases as these three parameters increase.

In the dermis, in addition to the fiber bundles that have 1-10 $\mu$m diameters, there are collagen fibrils approximately 100 nm in diameter that do not associate into bundles, and a variety of smaller particles and structures. These scattering elements are much smaller than visible wavelengths of light, and therefore contribute to Rayleigh scattering of light that we have modelled as isotropic scattering.

2.5 Conclusions

The optical properties of neonatal skin were determined in the visible region from 450–750 nm. The reduced scattering coefficient, $\mu_s(1-g)$, increases directly with gestational maturity of the infant, while the absorption coefficient is independent of gestational maturity. Generalized empirical equations were obtained that can be applied to obtain the scattering coefficient spectra for skin of any specified maturity, and dermal absorption spectra for skin at all maturities.

Mie theory can be used to quantitatively explain the scattering properties of the collagen fiber bundles within the dermis. The collagen fiber bundles are the predominant scattering elements in the skin, and the amount of scattering is strongly dependent on the concentration, size, and index of refraction of these bundles. The increase in the reduced scattering coefficient with gestational maturity is quantitatively accounted for by the accompanying increase in both concentration and size of the collagen fibers.

Section 3

Reflectance Measurements With An Optical Patch

3.1 Introduction

Transcutaneous reflectance spectroscopy involves the measurement of light diffusely reflected from the skin. This light has travelled within the skin, and has had an opportunity to sample the absorbers inside the skin. Since light reflected from a tissue is diffuse, the total true reflection can be measured with a distant detector, or an integrating sphere, where all the reflected light is observed equally. The total reflectance of a tissue is dependent on the ratio of its reduced scattering to absorption coefficient, and so evaluation of the quantity of absorbers within a tissue can be inferred from the total reflection only with knowledge of the scattering properties of the tissue. If not all the reflected light is collected during a reflectance measurement, then the reflected spectra can be interpreted if the collection characteristics of the measurement device is known.

Figure 8A:
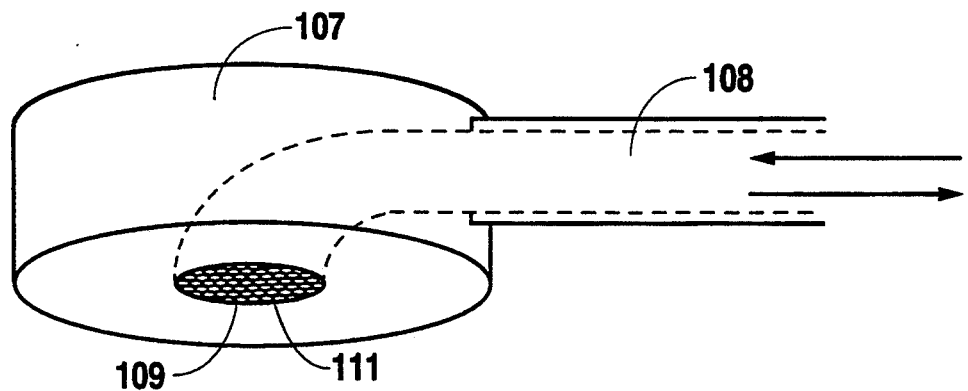
FIG. 8A is an optical patch, in accordance with the present invention.
Figure 8B:
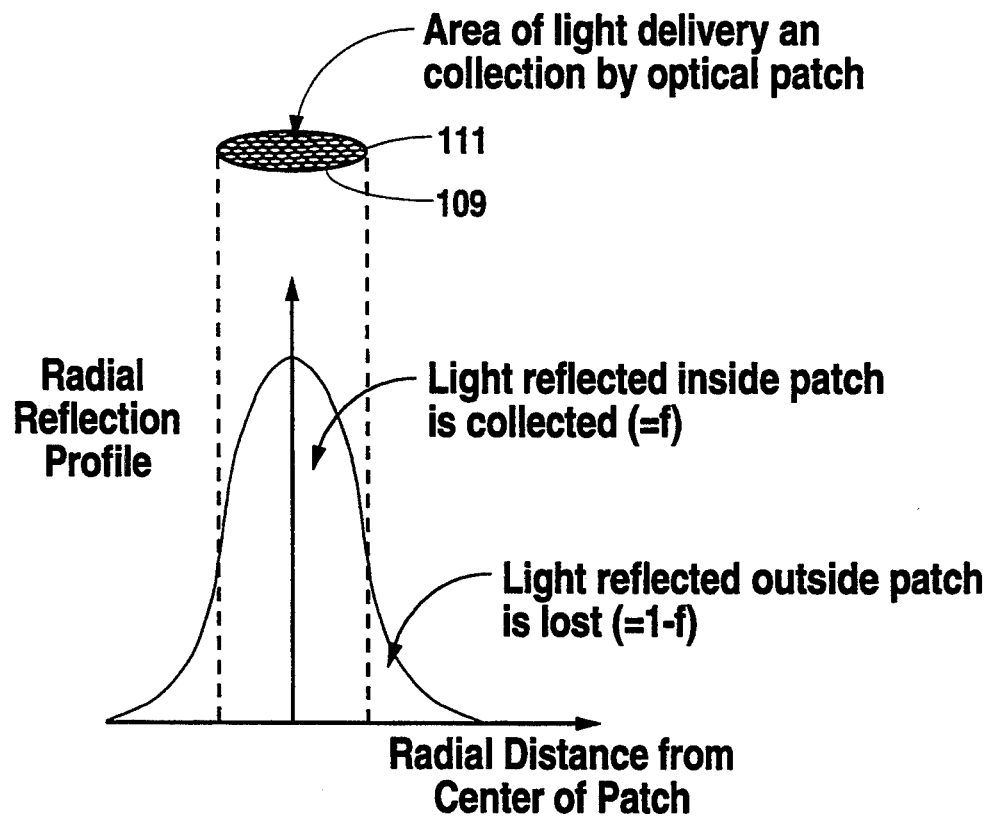
FIG. 8B is a Monte Carlo prediction of the reflectance profile as a function of radius, for the optical patch of FIG. 8A.

For clinical measurements, the devices used should be small, durable, and easy to use. With these considerations in mind, an optical patch 107, illustrated in FIG. 8A, has been designed for transcutaneous reflectance measurements in accordance with the present invention. The patch 107 includes a bundle 108 of mixed light delivery and collection fibers 109 and 111, and is placed flush with the skin surface. FIG. 8B shows the radial reflectance profile from typical neonatal skin, predicted by a Monte Carlo computer simulation of light delivered through the optical patch 107. FIG. 8B illustrates that light delivered through the patch spreads beyond the boundaries of the optical patch, and only a fraction of the reflected light is collected. The collection efficiency depends on the light collection and delivery geometry and on the optical properties of the tissue. Hence, the geometry of the optical transducer, such as an optical patch or a catheter, and the optical properties of the tissue being measured affect correct interpretation of measurements.

The reflected light measured with an optical patch is usually calibrated relative to a standard reference, such as teflon. The reflectance, M, measured with the optical patch can be expressed as:

$$M = \frac{S\,D\,f_{tissue}\,R_{tissue}}{S\,D\,f_{standard}\,R_{standard}} \tag{3-1}$$

where S is the total light source efficiency, D is the total detector efficiency, and f is the collection efficiency of the optical patch for the material measured. The term f physically specifies the fraction of the total reflected light that reaches the collection fibers of the optical patch. The term $R_{tissue}$, or simply R, denotes the true total reflectance of the material measured (tissue or standard). Note that S. and D cancel in Equation 3-1, yielding a measurement that is independent of the light source and detector characteristics.

Equation 3-1 can be written as:

$$M = f^* \, R_{tissue} \tag{3-2}$$

where $$f^* = \frac{f_{tissue}}{f_{standard}\,R_{standard}} \tag{3-3}$$

The combination $f_{standard}\,R_{standard}$ is a constant for a given standard at any particular wavelength. Calculations of $f_{tissue}$, or simply f, can be converted to $f^*$ by division by the appropriate constant ($f_{standard}R_{standard}$) for the reference standard at the wavelength of interest.

The fraction, f, of light collected by the optical patch is dependent on both the absorption, $\mu_a$, and reduced scattering, $\mu_s'$, coefficients of the measured tissue. Since both R and f are functions of both optical coefficients, either $\mu_a$ and $\mu_s'$ can be determined if the other is known and the reflectance is measured. In our case the absorption coefficient is desired while the scattering coefficient of the tissue is known. When measurements are performed relative to a reflectance standard reference, consideration of the collection efficiency, $f_{standard}$, of the optical patch for the standard reference used is as important as the reflectivity of the standard, $R_{standard}$.

The reflectance of a tissue is dependent on the quantity of absorbers within the tissue, and also on the location of the absorbers. Melanin in the skin, which differentiates skin color between people, is present only in the epidermis. The epidermis is the topmost layer of the skin, and is approximately 50 $\mu$m thick. Because of its localization in the epidermis, melanin is expected to affect the reflectance of the skin, and the collection efficiency of the optical patch differently than do diffuse absorbers in the skin.

In Subsection 3.2, the measurement of the true reflectance of a material is discussed. In Subsection 3.3, physical measurements on phantoms are preformed to determine the collection efficiency of the optical patch 107 as a function of the optical properties of the tissue. In Subsection 3.4, Monte Carlo computer simulations are used to predict the collection efficiency of optical patch 107. In Subsection 3.5, the effect of a thin superficial layer, simulating epidermis, on reflectance and on the optical patch collection efficiency is predicted by Monte Carlo computer simulations. Finally, in Subsection 3.6, an iterative method to determine $\mu_a$ from the measurement, M, is presented. This method requires knowledge of the scattering properties of the tissue, and the equations relating $\mu_a$ and $\mu_s'$ to R and f*.

3.2 Measurement Of Diffuse Reflectance

Figure 9:
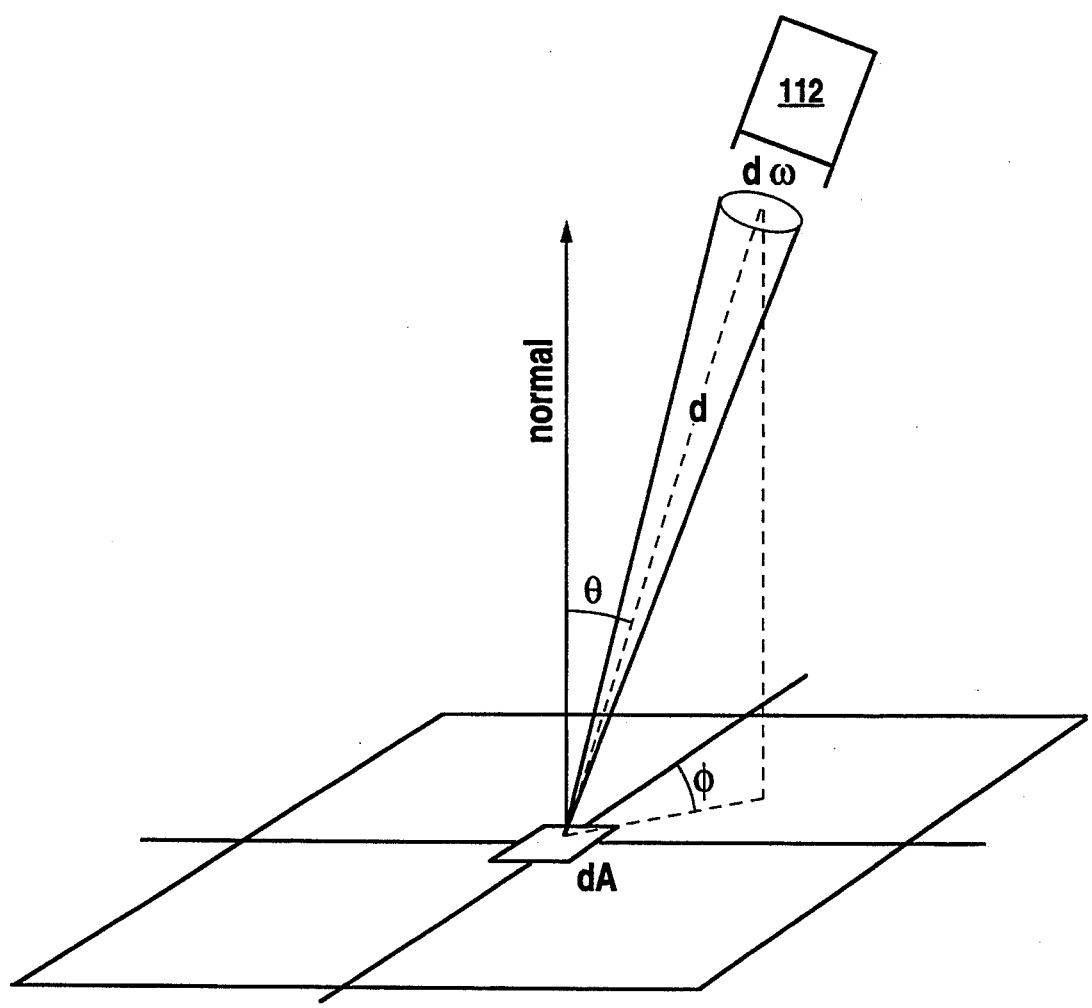
FIG. 9 illustrates the parameters that define the collection of light from a unit surface area by a distant detector.

To measure the true reflectance of a material, the detector has to be placed relatively far away from the material. A fraction of the light remitted from the surface reaches the distant detector. The fraction of the reflected light that reaches the detector can be calculated when performing absolute measurements. When measurements are calibrated relative to a standard of known reflection, the collection fraction remains constant when the reflectance of the sample and of the standard are measured. The light reaching a distant detector depends on several factors, namely the geometry of the light collection arrangement and the profile of the remitted diffuse light. FIG. 9 illustrates the collection fraction for a distant detector 112, and defines the angles and distances which describe the collection geometry of a distant detector.

The reflection signal, C(r,θ,dω), recorded by a distant detector 112 in FIG. 9 is expressed as:

$$C(r,\theta,d\omega) = G(r,\theta,d\omega) \; S \; D \; R \qquad (3\text{-}4)$$

where G(r,θ,dω) is a geometrical factor which accounts for the fraction of reflected light reaching the detector, S is the light from the source, D is the detector 112 response, and R is the true reflectance of the material. As shown in FIG. 9, G, and consequently C, are dependent on the distance, r, of the detector 112 from the material, the angle, θ, of the detector from the normal, and the solid angle of collection, dω.

The angular distribution of the reflected light is dependent on the reflective material and the angel of incidence of the light introduced to the material. In an ideally diffusing material, or Lambertian reflector, the reflected light is isotropic and the angular distribution of the reflected irradiance is independent of the angel of incidence. For a Lambertian surface, the light collected by the detector and G(d,θ) are dependent on cos(θ), as indicated in FIG. 9. All matte surfaces can be considered Lambertian when the angles of incidence and detection are small. The Lambertian approximation is invalid only at extreme angles [Kortum 1969].

The term G(d,θ) should not be confused with the term f introduced in Subsection 3.1. Both terms refer to collection fractions, but G(d,θ) refers only to the fraction of reflected light from a unit surface area, dA, and is dependent only on the location of detector 112 relative to dA. G(d,θ) is applicable when the light detector is far from the reflective unit surface, dA. In this situation, despite any spatial distribution of reflectance profile, R(ρ), gives the amount of light remitted from the surface as a function of the radial distance, ρ, from the center of the reflective source to the point of remittance. The term f, however, referred to the collection fraction for measurements at the tissue surface, and so this collection fraction depended on the diffuse reflection profile, R(ρ), and therefore was also dependent on the optical properties of the tissue.

The diffuse reflectance was measured as a function of distance between the detector and the reflective surface. The effect on the measured signal of varying the reflected light profile was determined, and is described in Subsections 3.2.1 and 3.2.2.

3.2.1 Point Source Delivery

Figure 10:
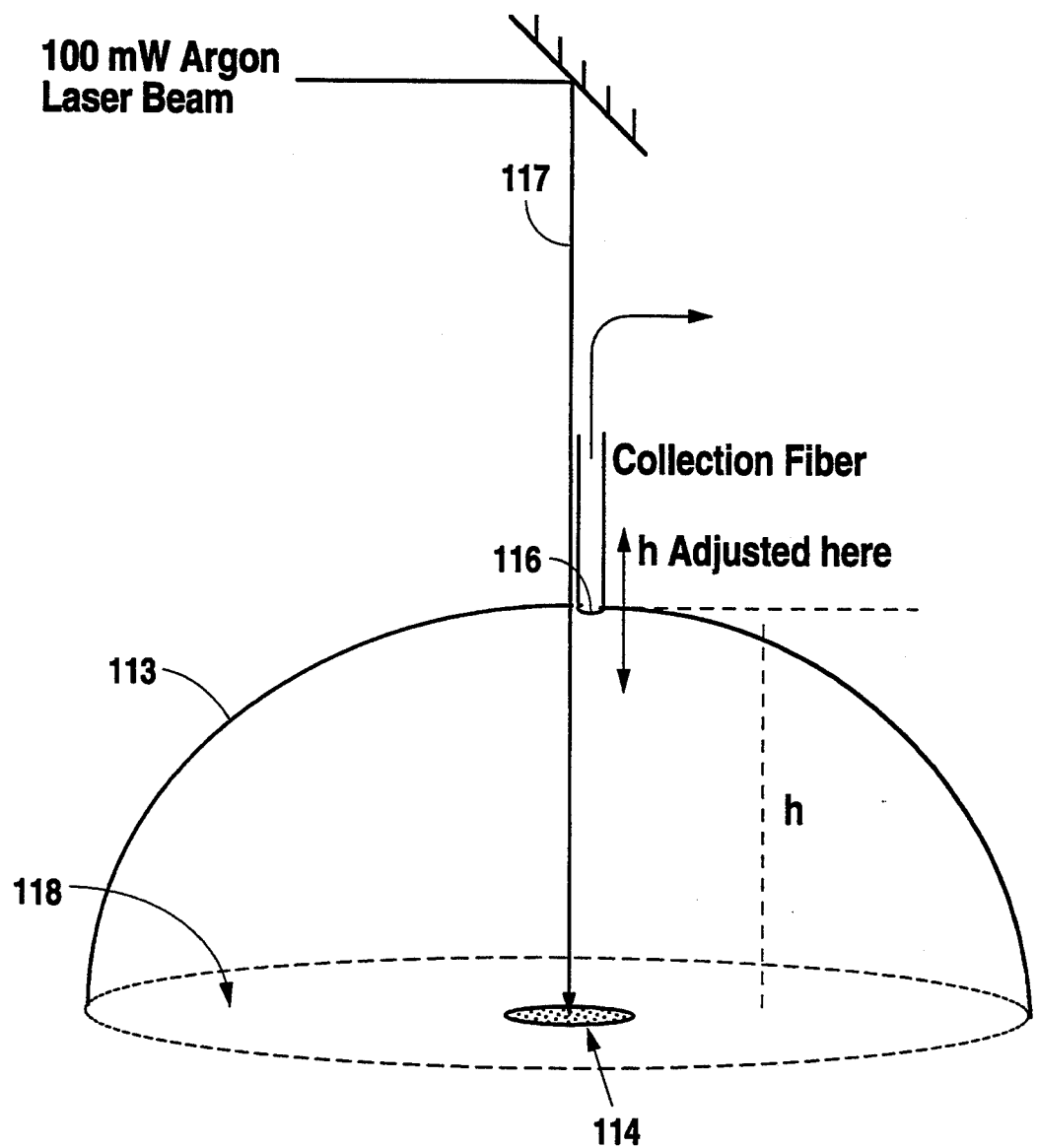
FIG. 10 illustrates reflectance measurement where light is delivered to a medium as a point source.

If the dimensions of the surface area from which the light is remitted from a medium is small relative to d, then the reflected light is distributed in a hemisphere 113 centered at the reflective source 114. This geometry is illustrated in FIG. 10. The distance, d, of the detector 116 from the surface is equivalent to the radius of the hemisphere 113 over which the light is distributed. The surface area of such a hemisphere 113 is $2\pi d^2$. The detector collects the light in a constant area, A, of this hemisphere, and so the light detected, G(d,θ) is equal to:

$$G(d,\theta) = \frac{A}{2\pi d^2} \qquad (3\text{-}5)$$

The angle of collection, θ, remained constant at 0°, and therefore G(d,θ) is a function only of $1/d^2$.

The logarithm of the above equation gives:

$$\log [C(d,\theta)] = \log [A] - 2 \log [2\pi f] \qquad (3\text{-}6)$$

Therefore, the plot of detected light, log[C(d,θ0], and distance, log[d], should have a slope of −2.

FIG. 10 illustrates the experimental arrangement used to verify the behavior of reflected signal as a function of distance when the light is delivered to the reflective material as a point source. The reflective material used was an optically thick block of teflon (dimensions 20 cm×20 cm×5 cm). The argon laser beam 117 (488 nm), delivered normally to the block of teflon 118, spread from the point of delivery before remission.

Figure 11:
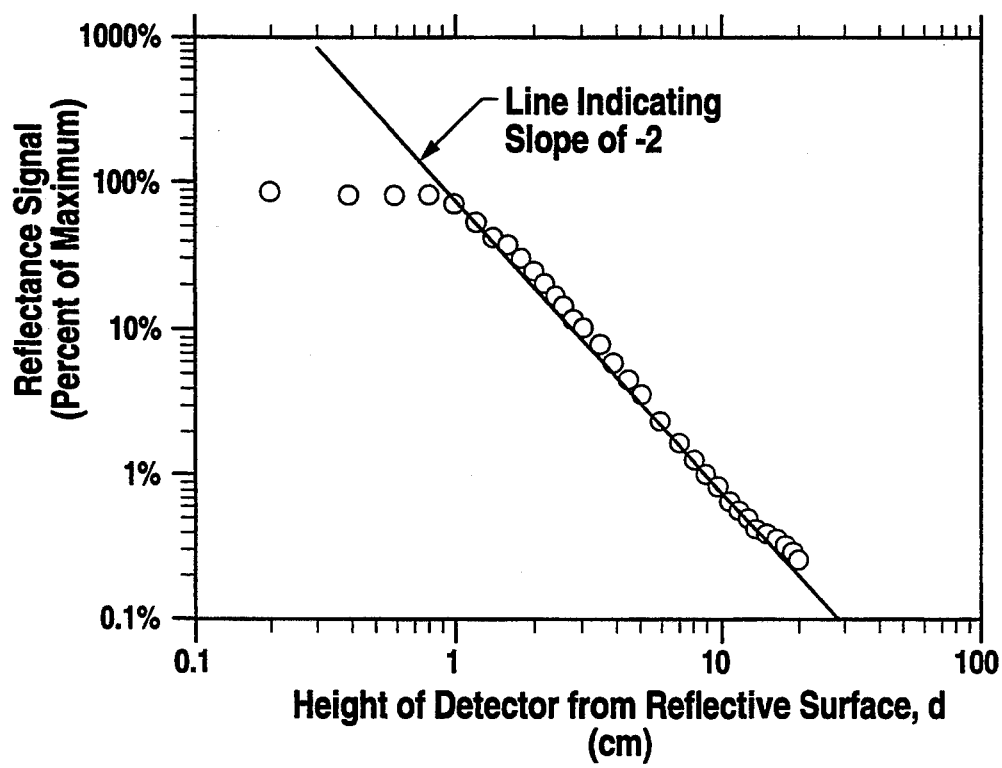
FIG. 11 is a graph of the reflectance signal as a function of the distance from the detector to the reflective surface, with light delivered to the reflective medium as a point source.

The measured reflected signal plotted versus distance of the detector is shown in FIG. 11. It can be seen from this figure, the predicted relationship in Equation 3-6 holds as the height, d, becomes large relative to the diameter of the collection fiber and the diffuse remittance area. At distances close to the reflective surface, this relationship does not hold as the remittance source is not small relative to the radius of the imaginary hemisphere.

3.2.2 Broad-Beam Source Delivery

Figure 12:
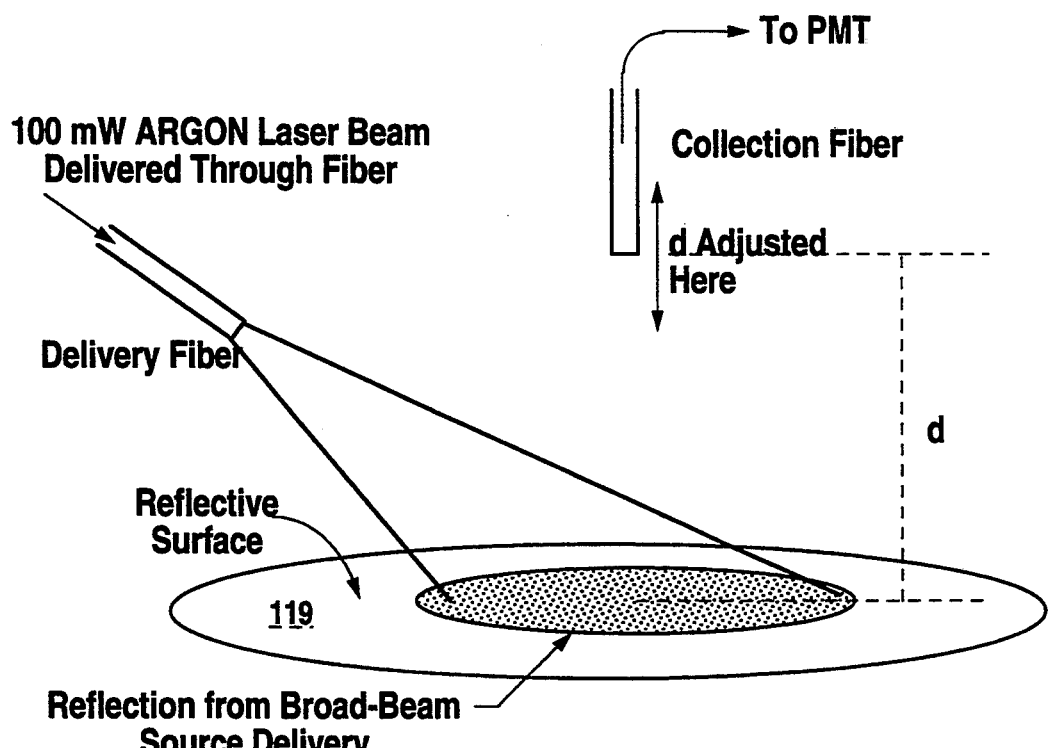
FIG. 12 illustrates reflectance measurement where light is delivered to a reflective medium as a broad-beam source through a fiber.

If light is delivered to the reflective surface as a broad beam, the area of light delivery is not always small relative to the distance of the collection fiber. FIG. 12 shows the experimental arrangement used to study the reflected signal when the light is not delivered to the reflecting material at a single point, but rather as a broad beam. The experiment was performed with teflon as the reflective material 119 (see previous section for description).

Figure 13:
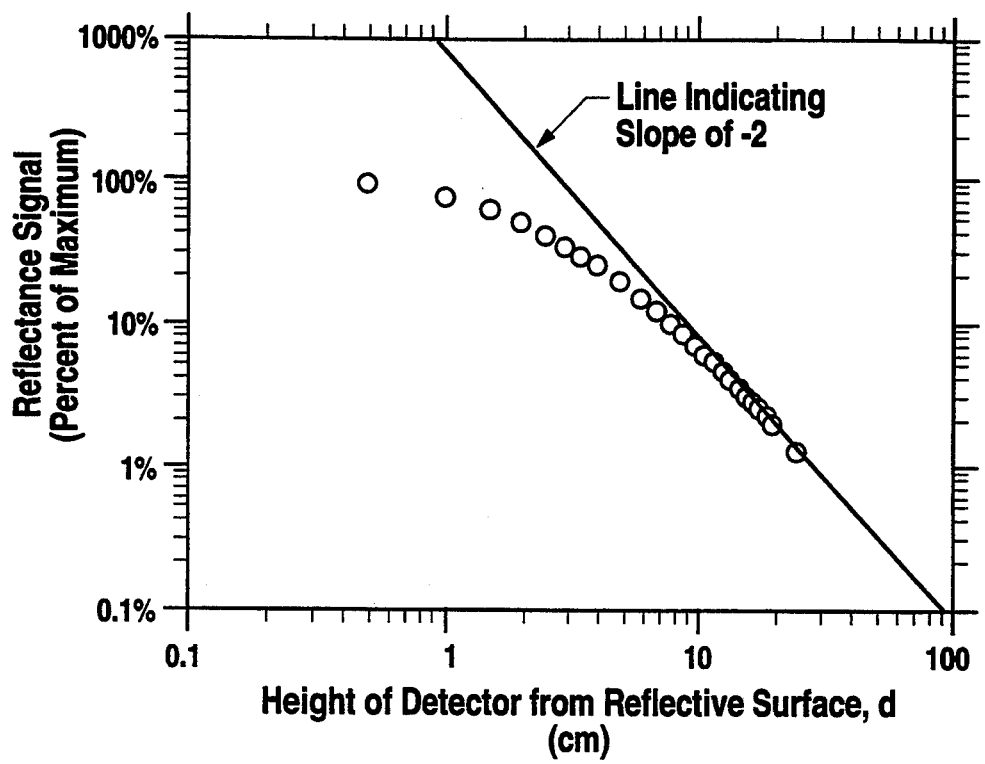
FIG. 13 is a graph of the reflective signal as a function of distance from the detector to the reflective surface with light delivered to the reflective surface with a broad-beam source.

The results are shown with logarithmic scales in FIG. 13. The hemispheric approximation is seen to hold only when the distance, d, is large relative to the diameter of the area of light delivery. Comparing the results in FIG. 13 with those in FIG. 11, it can be seen that broadening of the light source delivery area results in an increase in the distance, d, required before the hemispherical approximation holds. When d is small (<8 cm), the reflectance signal does not decrease as rapidly with increasing d as predicted by the hemispherical approximation. The reason being that decreases in the signal (as $1/d^2$) from each point on the surface is compensated by an increase, with d, in the area of the reflectance source viewed by the fiber.

3.2.3 Conclusions

Based on the definitions of diffuse reflectance and on the above observations, the following considerations should be heeded in order to appropriately measure true reflectance from a surface. The source delivering light to the reflective surface needs to be small relative to the dimensions of the reflective medium, such that all the light is either absorbed in the medium or remitted from the surface. The distance of the detector form the reflective surface should be large relative to the dimensions of the remittance area. This will assure that changes in the amount of light seen by the detector, due to variations in the remitted profiles, are small. Finally, when measurements are performed relative to a standard of known reflectance, the delivery and collection geometry should be kept constant for both measurements. These guidelines will be considered when the true reflectance of phantoms and tissues are measured.

3.3 Physical Measurements Of Collection Efficiency

True reflectance, R, is related to measured reflectance, M, using an optical patch by a factor f*, as discussed in Equation 3-2. In order to relate optical patch measurements to true reflectance measurements, the collection efficiency of the optical patch, f*, has to be known. In a series of phantoms in which the optical coefficients were known, f*, was determined by measuring the true reflectance, R, and the optical patch measurement, M:

$$f^* = \frac{M}{R} \quad (3\text{-}7)$$

The relationships between the optical interaction coefficients of the medium, $\mu_a$ and $\mu_s'$, and f* were determined for these phantoms. Later, in Section 3.4, Monte Carlo simulations are used to predict f* as a function of the tissue optical interaction coefficients.

3.3.1 Phantom Preparation

Liquid phantoms in which the optical properties are known precisely were prepared. The scattering elements in the phantoms were 579-nm polystyrene microspheres for which the scattering coefficient, $\mu_a$, and the anisotropy, g, of the microspheres are calculated by Mie theory, and verified by collimated transmission measurements. Trypan blue, for which the absorption coefficient was carefully measured, was used as an absorption medium in the phantoms. A series of phantoms were made in which the reduced scattering coefficient, $\mu_a(1\text{-g})$, ta 630 nm was set at 6 cm$^{-1}$, 24 cm$^{-1}$, 42 cm$^{-1}$, and 60 cm$^{-1}$. The absorption coefficient of the phantom at 630 nm was varied between 0 cm$^{-1}$ and 20 cm$^{-1}$ by the addition of trypan blue to the phantom.

3.3.2 Measurement Technique

Figure 14A:
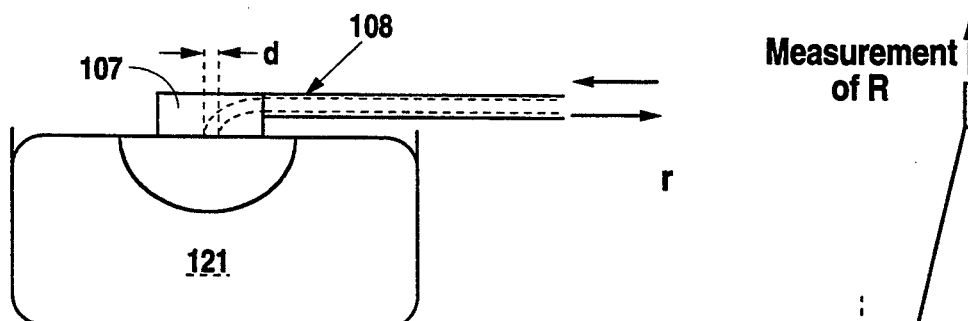
FIGS. 14A and 14B illustrate measurement of the reflective characteristics of phantoms.
Figure 14B:
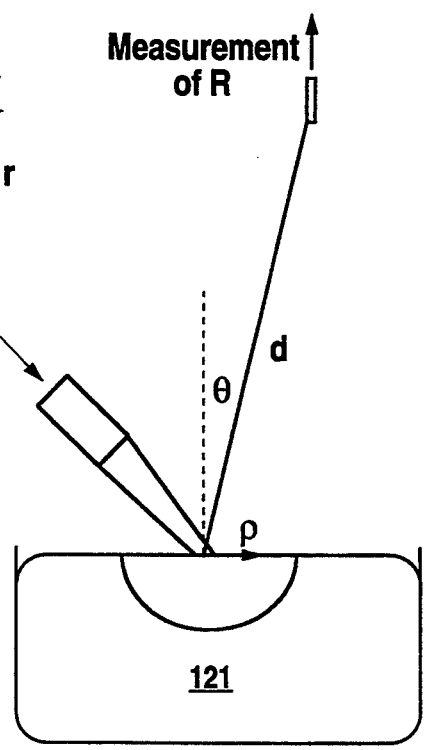

The optical patch measurement of each phantom, SDf$_{phantom}$R$_{phantom}$, normalized by optical patch measurement of teflon, SDf$_{teflon}$R$_{teflon}$, to yield M of each phantom 121 as made, as illustrated in FIG. 14A. The measurement of the phantom, GSDR$_{phantom}$, normalized by measurement of a standard, GSDR$_{standard}$, was then obtained by means of a distant detector, as illustrated in FIG. 14B, to determine the true R$_{phantom}$. The calibration method relative to reflection standards is described mathematically in Subsection 3.3.2a and 3.3.2b. In both situations depicted in FIGS. 14a and b, the light from the collection optical fiber was spectrally separated by a diffraction grating, and measured with a CCD camera (Photometrics Series 200). The true reflectance for each of the phantoms was measured relative to the reflectance of a standard of known reflectance (spectralon TM, Labsphere Inc., North Sutton, N.H.; R$_{standard}$=0.994). The measurements of the phantoms with the optical patch were calibrated relative to measurements on teflon, SDf$_{teflon}$R$_{teflon}$, as is done with clinical transcutaneous measurements, to yield:

$$M = R_{phantom} f^* \quad (3\text{-}8)$$

a) Measured Reflectance with the optical patch

When the light reflected from the phantom is measured with the optical patch, as shown in FIG. 14A, light remitted from the phantom 121 and reaching the patch 107, can be represented as:

$$\text{Measurement of phantom} = S\,D\,f_{phantom}\,R_{phantom} \quad (3\text{-}9)$$

where S and D again represent the source and detector terms, f$_{phantom}$ is the fraction of reflected light that actually reaches the detector, and R$_{phantom}$ is the true reflectance of the phantom.

Since the readings measured on the phantom need to be standardized, a standard is also measured. Again, the light reaching the detector can be represented as:

$$\text{Measurement of standard} = S\,D\,f_{standard}\,R_{standard} \quad (3\text{-}10)$$

where f$_{standard}$ and R$_{standard}$ are analogous to f$_{phantom}$ and R$_{phantom}$ defined above. The measurement of the phantom, M$_{phantom}$, relative to that of the standard can then be reduced to:

$$M_{phantom} = \frac{S\,D\,f_{phantom}\,R_{phantom}}{S\,D\,f_{standard}\,R_{standard}} = f^* R_{phantom} \quad (3\text{-}11)$$

The collection efficiency f* at any wavelength of interest is therefore equal to:

$$f^* = \frac{f_{phantom}}{f_{teflon}\,R_{teflon}} \quad (3\text{-}13)$$

Recalling Equation 3-2, the reflectance measured with the optical patch, M, can be described as the product of f* and the true reflection, R, of the material.

$$M_{phantom} = f^* R_{phantom} \quad (3\text{-}13)$$

b) True Reflectance of the Phantoms

The light collected with a distant detector, C$_{phantom}$, from reflection of the phantom is expressed as:

$$C_{phantom} = S\,D\,G\,R_{phantom} \quad (3\text{-}14)$$

where S represents the light delivered by the source, D represents the detector efficiency, and G represents the amount of light reaching the detector due to the geometry of collection, and R$_{phantom}$ represents the reflection of the phantom. Since the source and detector are both not at extreme angles relative to the normal of the phantom surface, the reflected light can be assumed to be remitted as a true Lambertian, and differences between the angular profiles of the reflected light from the different materials are not significant [Kortum 1969]. The properties of a Lambertian reflector are described in Subsection 3.2.

Similarly, the light collected, $C_{standard}$, from reflection measurements with a distant detector for the standard is:

$$C_{standard} = S \ D \ G \ R_{standard} \qquad (3\text{-}15)$$

where $R_{standard}$ is the reflection of the standard used. Since the terms in common in Equations 3-15 and 3-14 can be factored out, the true reflection of the phantom, $R_{phantom}$, can be calculated as:

$$R_{phantom} = \frac{C_{tissue}}{C_{standard}} R_{standard} \qquad (3\text{-}16)$$

Also, measurements of teflon were made to specify $R_{teflon}$, so that later calculation of $fR_{teflon}$ was possible.

3.3.3 Results

Figure 15:
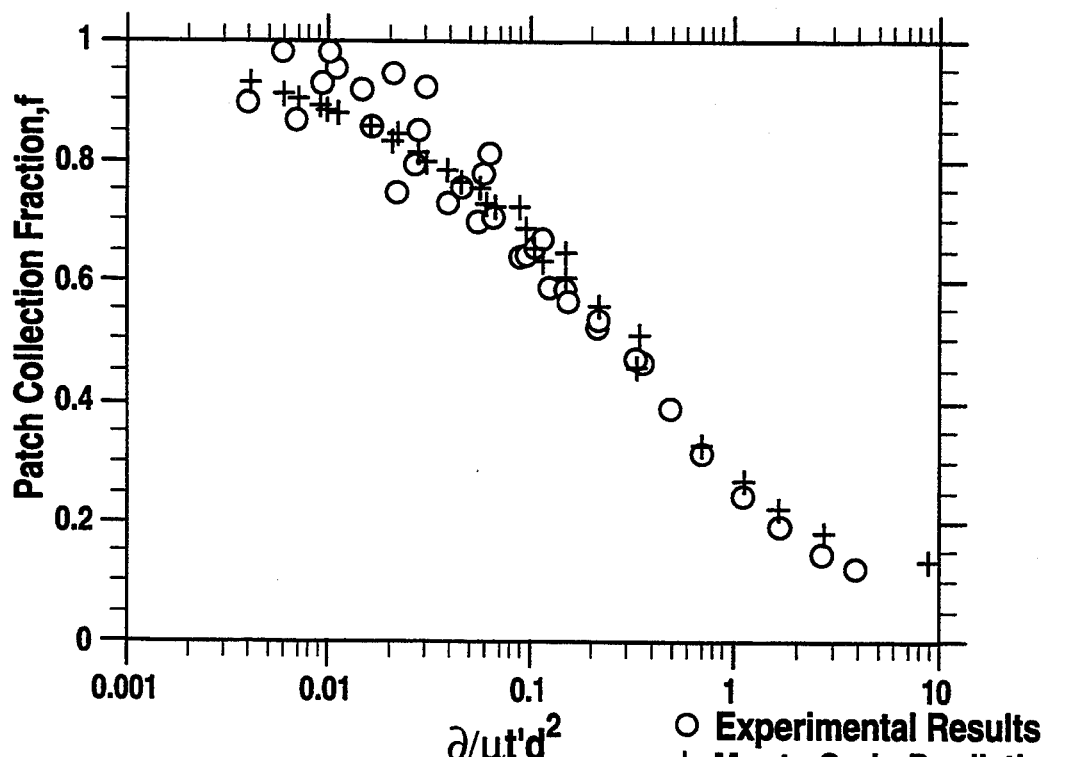
FIG. 15 is a graph of the predicted and experimental results for the collection fraction of the optical patch of FIG. 8A.

The collection efficiency of the optical patch 107 was found to increase with both the absorption and scattering coefficients of the measured material (See FIG. 15).

After further analysis of the f* measurements at 630 nm in phantoms of known optical properties, the collection efficiency, f*, was found to be inversely dependent on $\delta/\mu_t'd^2$, where $\delta$ is the penetration depth of the light in the tissue and is equal to:

$$\delta = \frac{1}{\sqrt{3\mu_a(\mu_a + \mu_s')}} \qquad (3\text{-}17)$$

and $\mu_t'$ is the reduced attenuation coefficient, and is equal to:

$$\mu_t' = \mu_a + \mu_s' \qquad (3\text{-}18)$$

and d is the diameter of the optical patch. The term $\delta/\mu_t'^2$ is dimensionless. At any fixed wavelength, e.g. 630 nm, the product $f_{standard}R_{standard}$ is constant, and so f of the material is equal to the determined f* divided by $f_{standard}R_{standard}$ for the wavelength studied. The relationship between the collection efficiency of the optical patch, f, and $\delta/\mu_t'd^2$ determined by the measurements on phantoms is illustrated in FIG. 15. Also shown in FIG. 15 are the results of f predicted by Monte Carlo as described in the next section. From this relationship, the collection efficiency of the optical patch can be determined for any specified optical properties in the tissue. The effective collection efficiency, f*, is sensitive to the reflectance, $r_{standard}$, and the collection efficiency, $f_{standard}$, of the material used as a reference.

3.4 Monte Carlo Determinations Of Collection Efficiency

The Monte Carlo computer model is a stochastic model of the transport of photons in a medium in which there are defined rules of interactions of the photons with the medium. The Monte Carlo computer model provides a useful tool for studying the light transport in tissue [Keijzer 1989, Prahl 1989a]. A model tissue or phantom can be homogeneous, or contain i layers with distinct optical properties ($\mu_a$, $\mu_s$, g). The Monte Carlo computer program simulates the launching of photons of unit weight, W=1, into a tissue. The weight, $W_{j,n}$, is related to the amount of light energy associated with the $n^{th}$ photon at its $j^{th}$ step within the tissue. Each photon on the average interacts with the tissue after a mean free path of $1/\mu_t$, where $\mu_t = \mu_a + \mu_s$. The computer generates each incremental step, $dl_j$, by using a random number (RND) generator: $dl_j = -\ln(RND)/\mu_t$. At each interaction, a fraction $\mu_a/\mu_t$ of the current photon weight, or a weight $W_{j,n}\mu_a/\mu_t$, is deposited as absorbed energy, and a fraction $\mu_s/\mu_t$, or a weight $W_{j,n}\mu_s/\mu_t$, is scattered into a new angle.

The angle at which the photon scatters is determined by the Henyey-Greenstein function [Henyey 1941]. The Henyey-Greenstein function describes the angular profile of light scattering for a given anisotropy, g. The computer can keep track of the step length $dl_{j,k,n}$ of the $j^{th}$ step of the $n^{th}$ photon i the $i^{th}$ layer of tissue, and calculate the cumulative pathlength, $L_{i,n}$, of each photon in each layer:

$$L_{i,n} = \sum_{j=1}^{J} dl_{j,i,n} \qquad (3\text{-}19)$$

where J is the total number of steps that have been taken.

If a photon, n, of weight $W_{n,j}$ traveling in a medium reaches the upper surface of the medium at step j, a fraction of this photon may escape as reflected light. The fraction, u, that escapes is determined by Fresnel's laws, and is dependent on the angel of incidence of the photon, and the index of refraction of the medium [Prahl 1989a]. The remaining weight of the photon, $(1-u)W_{n,j}$, is internally rejected and continues its propagation in the medium. The fraction that was internally reflected may be absorbed bin the medium, or may be partially remitted at a later time. For each $n^{th}$ photon, there are $J_n$ occurrences of photon weight escape. When the photon weight, $W_n$, drops below a threshold level equal to 1/N, then photon migration is terminated according to a survival roulette algorithm described by Prahl et al. [Prahl 1989a].

Monte Carlo simulations provide statistical determinations of the distribution of light within a medium, and the amount of light emitted at each position from the light input location. The accuracy of the results increase with the number of photons simulate, N, and the error in the results are proportional to $1/\sqrt{N}$. Monte Carlo simulations are time inefficient, and to repeat simulations for each specified set of optical properties is unnecessarily repetitious. It is desirable to use redundant information from Monte Carlo simulations to enable repeated calculations of the reflection from media with variable optical properties.

To enable the repeated calculations, Monte Carlo simulations are used to generate, for each photon launched, the distance of emission from its point of delivery into the medium, r_em, and the its pathlength of travel in an absorptionless medium, $L_i$, for each layer i in the medium. Many photons are simulated, and these distances are recorded, for each photon, in dimensionless units. This procedure is explained in Subsection 3.4.1. The L and r_em distributions can then be used to predict the remission profile for a medium with any desired absorption and scattering coefficients, as explained in Subsection 3.4.2. The remission profile is then used to calculate the collection efficiency of the optical patch in a medium, and this is explained in Subsection 3.4.3.

3.4.1 Photon Histories In An Absorptionless Medium

When the Monte Carlo simulation is conducted with zero absorption specified, then photons are terminated when they are emitted from the medium, and there is never any absorption. Whenever a fraction of photon n is emitted at the $J_{th}$ step of its propagation, the pathlength in each layer i, $L_{i,n}$, is calculated by Equation 3-19, and the distance from the input position in which the photon was emitted, r_em$_{n,j}$, are noted in dimensionless units of effective scattering lengths. The Monte Carlo program keeps track of $L_{i,n}$ and r_em$_{n,j}$ in units of distance (cm), and they are converted to dimensionless units of effective scattering lengths by the following equations:

$$L \text{ (in dimensionless units)} = L_{n,i}\text{(cm) } \mu_s'0(\text{cm}^{-1}) \quad (3\text{-}20)$$

$$\text{r\_em}_{n,j}\text{(in dimensionless units)} = \text{r\_em}_{n,j}(\mu m)\mu_s'0(\text{cm}^{-1}) \quad (3\text{-}21)$$

where $\mu_s'0$ is the scattering coefficient of the absorptionless medium simulated by the Monte Carlo program during generation of $L_{i,n}$ and r_em$_{n,j}$ for each photon emission event.

For each photon simulated, there may be more than one emission event from the medium. Each time an emission event takes place, the photon fraction emitted, the pathlength of travel in each layer, $L_{i,n}$, and the point of emission, r_em$_{n,j}$, are recorded in a single file. We refer to this file as the "photon histories file". Table 3.1 shows an excerpt from a sample photon histories file for a two layer model. As can be seen in this table, for each photon, there usually are several emission events, each time a fraction of the photon weight is emitted.

TABLE 3.1

| I emission event | II photon number | III r_em (D.U.) | IV emitted weight, $W_0$ | V pathlength in layer 1, $L_1$ (D.U.) | VI pathlength in layer 2, $L_2$ (D.U.) |
|---|---|---|---|---|---|
| 1 | 1 | 11.466 | 0.9469 | 1.159 | 216.42 |
| 2 | 1 | 11.56 | 0.0273 | 1.2319 | 220.1 |
| 3 | 1 | 9.436 | 0.0014 | 1.4701 | 469.34 |
| 4 | 2 | 19.858 | 0.9514 | 0.99636 | 388.72 |
| 5 | 2 | 19.131 | 0.0219 | 1.6258 | 388.72 |
| 6 | 2 | 18.732 | 0.0016 | 2.1436 | 388.72 |
| 7 | 2 | 18.871 | 0.0007 | 2.9374 | 393.24 |
| 8 | 2 | 19.717 | 0.0002 | 4.1846 | 393.24 |
| 9 | 3 | 7.4592 | 0.9432 | 0.19463 | 200.12 |
| 10 | 3 | 6,495 | 0.0315 | 0.69934 | 209.54 |
| 11 | 4 | 0.77266 | 0.9463 | 0.41998 | 16.279 |
| 12 | 4 | 3.9246 | 0.0286 | 1.0853 | 26.33 |
| 13 | 4 | 10.543 | 0.0007 | 1.7824 | 441.32 |
| 14 | 5 | 1.114 | 0.9136 | 0.23726 | 2.1554 |
| 15 | 5 | 1.7175 | 0.0597 | 0.55202 | 3.4894 |
| 16 | 5 | 7.1016 | 0.0023 | 0.74358 | 68.178 |
| 17 | 5 | 6.8808 | 0.0006 | 2.8618 | 153.69 |
| . | . | . | . | . | . |
| . | . | . | . | . | . |
| . | . | . | . | . | . |

3.4.2 Calculation Of Reflectance Profile

The photo pathlengths, $L_{i,n}$, and the radii of emission, r_em$_{n,j}$, stored in the photon histories file are subsequently used to predict the profile of reflectance for a medium with any specified optical coefficients, $\mu_a$ and $\mu_s'$. In this new medium, for each emission event, the photon weight emitted, W, is calculated as from the recorded pathlength and absorptionless emission weight, $W_o$, as:

$$W = W_0 \exp\left(-\sum_{i=1}^{N_i} \mu_a L_i\right) \quad (3\text{-}22)$$

where $N_i$ is the number of layers in the Monte Carlo model, and $\mu_a$ is the specified absorption coefficient in the medium. Since $L_i$ is specified in dimensionless units of effective scattering lengths (see Equation 3-20), then $\mu_a$ also is expressed in dimensionless units. The absorption coefficient, $\mu_a$, in dimensionless units is related to the dimensional form (cm$^{-1}$) as:

$$\mu_a \text{ (in dimensionless units)} = \frac{\mu_a \text{ (in cm}^{-1})}{\mu_s' \text{ (cm}^{-1})} \quad (3\text{-}23)$$

where $\mu_a'$ is the scattering coefficient in the medium. When a uniform medium is simulated, (i.e. where the absorption of all layers is equal), then the same $\mu_a$ value is specified for all the layers.

The radial profile of remission (in discrete form) can be calculated from the photon remission data. We define radial remission profile, R(k) as the amount of light (in watts or photons) emitted from the surface annulus with inner radius equal to the product of k and Δr_em, and with annular thickness Δr_em.

For a given radius of remission, r_em, the value of the discrete radius, k, is chosen according to the following condition:

$$k\Delta r\_em < r\_em < (k+1) \Delta r\_em \quad (3\text{-}24)$$

where k=0,1,2, ... $K_{max}$. The maximum discrete radius considered is $K_{max}$. Photon weights found to be emitted at radii, r_em, larger than Δr_em $K_{max}$ are added to the remission profile element R($K_{max}$). The programming statements used to determine k are included in Appendix B. The radial remission profile, R(k) can then be calculated by adding all photons, n, which are remitted at the discrete radius, k, i.e. which satisfy the condition in (3-upper):

$$R(k) = \sum_{n=1}^{N_a} W_0 \exp\left(-\sum_{i=1}^{N_i} \mu_a L_i\right) \quad (3\text{-}25)$$

The remission profiles, R(k), are calculated for media with different specified optical properties. For given optical properties, $\mu_s'$, the absorption coefficient is calculated in dimensionless units (Equation 3-23). The radial remission profile, R(k) is then calculated by Equation 3-24, and 3-25. The $L_{i,n}$, and r_em data for substitution i equations 3-16 and 3-17 are obtained by reading successive lines in the photon histories file (see Table 3.1). The remission profile, R(k) is then used directly in the convolution procedure to find the collection efficiency of the optical patch (see Section 3.4.3, and Appendix B).

In conclusion, this procedure is used to calculate the radial remission profiles for media with different optical properties. For each set of optical properties the photon histories file is used and there is no need to run a new Monte Carlo simulation.

3.4.3 Convolution Of Remission Profiles

If the radial dependence of reflection, $R(\rho)$, from a point source, as described above, is known, the radial dependence for a beam of finite parameters can be calculated by convolution of the radial profile with the input beam profile. Furthermore, the amount of light escaping from a defined area can be calculated if the input and output areas are specified. In this section the convolution of the remission profile predicted by Monte Carlo is described for the case where the input and output areas are two concentric circles. This method is then used to calculate the collection efficiency of the optical patch.

If the light is delivered as a uniform circle with radius $R_{patch}$, then the fraction of reflected light that is remitted and collected within a concentric collection circle of radius $R_{patch}$ is:

$$\text{fraction collected} = \frac{\int_0^{R_{patch}} \text{collected light}}{\int_0^{R_{patch}} \text{collected light} + \int_{R_{patch}}^{\infty} \text{frost light}} \quad (3\text{-}26)$$

The total collected light, and total lost light described above are summed individually as the input is convolved across $R_{patch}$. The geometry description and equations used to calculate the collection efficiency from reflection radial profiles are developed in Appendix B. The equations presented in Appendix B can be applied for other devices with similar delivery and collection geometries.

3.4.5 Results

The collection efficiency, f, for an optical patch measurement from a uniform medium is predicted by Monte Carlo as described above, is also plotted in FIG. 15. The simulations coincide with the measurements in phantoms, which predict a unique relationship between f and $\delta/\mu_t'd^2$. Monte Carlo calculations of f were performed for a variety of optical patch diameters (d=2.1 mm, 4.2 mm, and 6.3 mm) and the non-dimensional relationship presented above was verified.

The relationship was fit by a third order polynomial, so that it may be utilized later to predict f if the optical properties are known. The polynomial fit was:

$$f = M_0 + M_1 x + M_2 x^2 + M_3 x^3 \quad (3\text{-}27)$$

where $$x = \text{Log}_{10}\left[\frac{\delta}{\mu_t' d^2}\right] \quad (3\text{-}28)$$

and $M_0 = 0.3132, M_1 = -0.3204,$
$M_2 = 0.07456, M_3 = 0.044523$

The correlation coefficient, r, for this polynomial fit is 0.996.

The Monte Carlo method described here can be used to determine the collection efficiency of an optical collection device with equal delivery and collection areas, such as another transcutaneous reflectance measurement device, or a catheter used for in vivo fluorescence detection. In addition to information on the absolute collection efficiency of an optical device, this method can be used to derive information on the spectral distortion introduced by the optical device due to different collection efficiencies at different wavelengths. With modifications, the Monte Carlo model can be used to determine the collection characteristics of devices with more complex delivery and collection geometries.

3.5 Collection Efficiency With A Thin Superficial Absorbing Layer: The Pigmented Epidermis Problem The Monte Carlo method described above could simulate a multi-layer tissue, as already explained. We wanted to use this feature to study the effect a thin absorbing layer has on the optical patch collection efficiency. This would simulate the epidermis in skin, which has scattering properties similar to the underlying dermis, but higher absorbing properties because of melanin. The thickness of the epidermis is very small compared to the dermis ($\approx 50$ µm for the epidermis compared to $\approx 900$ µm for the dermis). A two-layer Monte Carlo simulation in which the superficial layer was very thin compared to the infinitely thick underlying layer was used to simulate this.

3.5.1 Monte Carlo Thin Layer Simulation

A two layer Monte Carlo simulation was run in which the superficial layer (layer 1) had a thickness of 0.1 effective scattering lengths (See equation 3-20) and the underlying layer (layer 2) had a thickness of 60 effective scattering lengths. Layers 1 and 2 simulate the epidermis, and in infinite dermis respectively. An example of the output photon histories file for this model was shown in Table; 3.1, and as it can be seen the pathlength traveled by each photon in each layer, 1, and 2, was recorded independently as $L_1$ and $L_2$. Using this model we are able to vary the absorption coefficient in the epidermis and dermis independently by assigning separate absorption coefficients, $\mu_{a1}$ and $\mu_{a2}$, for layers 1 and 2. When the remission profile from the two-layer model is calculated, Equation 3-25 is written as:

$$R(k) = \sum_{n=1}^{N_n} W_0 \exp(-\mu_{a1}L_2)\exp(-\mu_{a1}L_2) \quad (3\text{-}29)$$

to accommodate the two absorption coefficients, $\mu_{a1}$ and $\mu_{a2}$, the remission profiles are convolved to find the collection efficiency, as described in subsection 3.4.5.

3.5.2 Results

Figure 16:
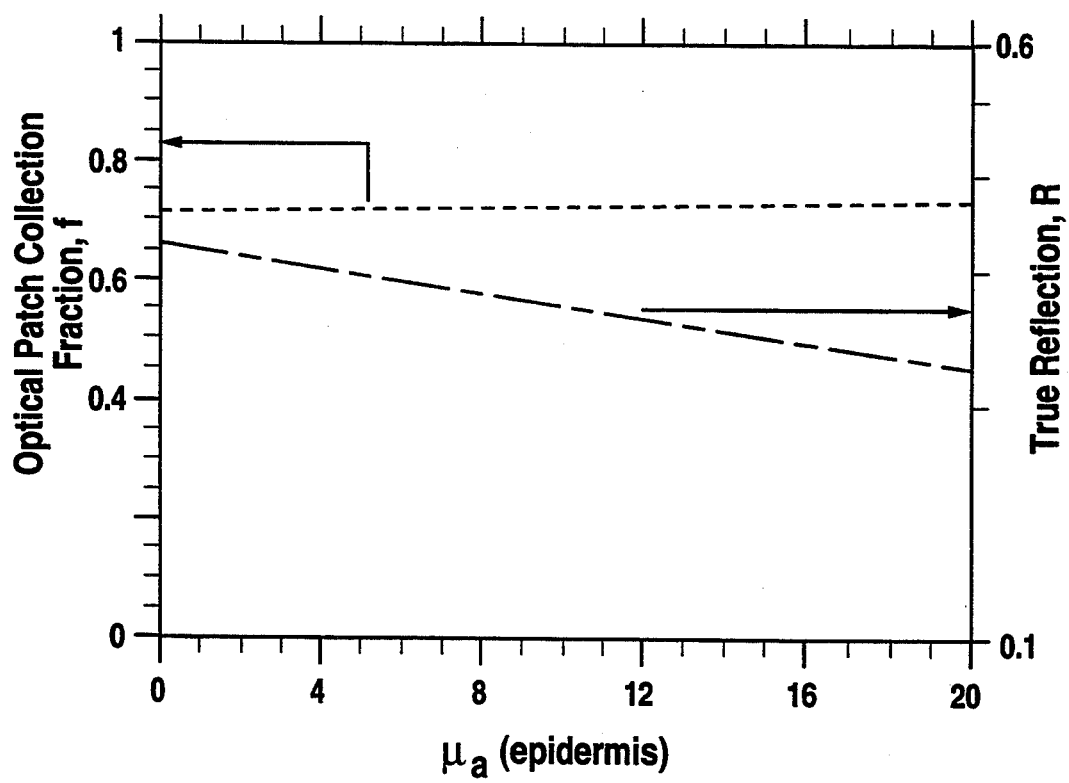
FIG. 16 is a graph of optical patch collection fraction and true reflection as a function of epidermal absorption.
Figure 17:
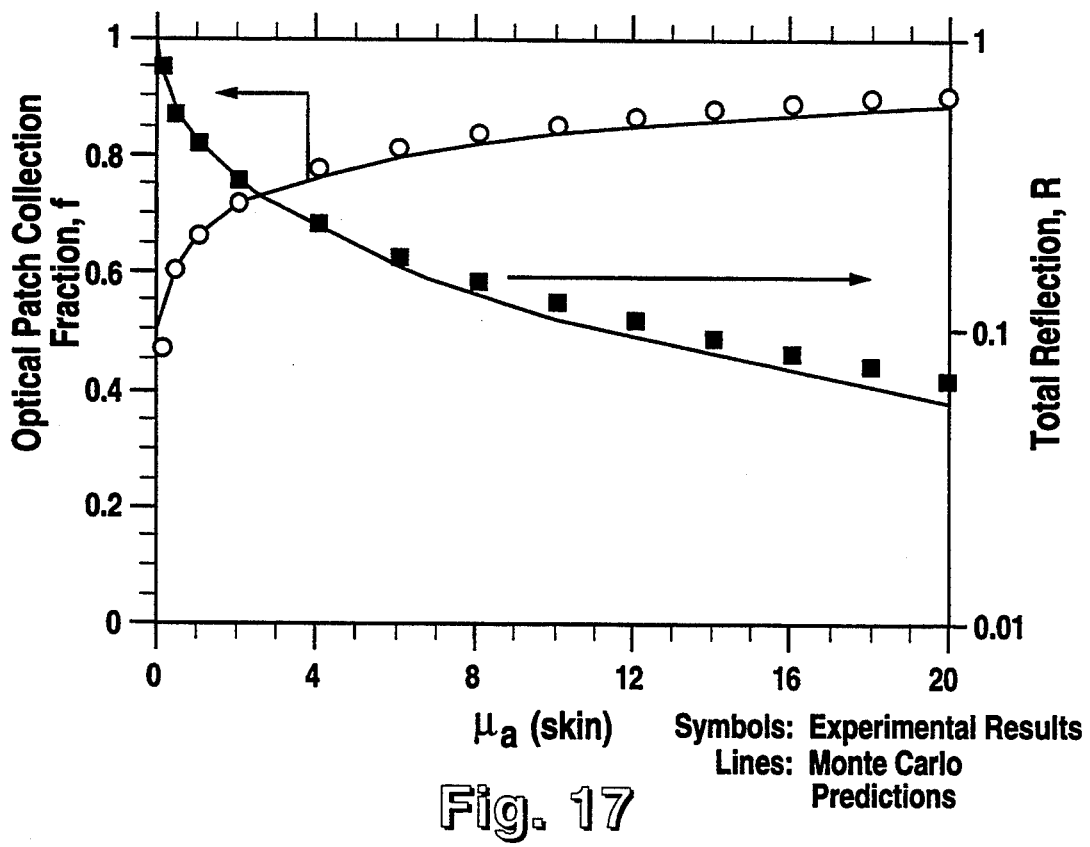
FIG. 17 is a graph of collection fraction and true total reflection as a function of absorption in an infinite medium simulating dermis.

The introduction of an absorbing layer has only a minimal effect of the collection efficiency of the optical patch, and the collection efficiency is still primarily determined by the optical properties in the bulk tissue. This effect is illustrated in FIG. 16 which shows the results of the Monte Carlo simulation in which absorption in the epidermis can result in significant decreases in the total reflection of the tissue, yet will only marginally increase the collection efficiency of the optical patch. For comparison, FIG. 17 shows the effect absorber in the bulk tissue has on both the reflection and the collection efficiency of the optical patch.

Therefore, one can conclude that the absorbance from the epidermis has to be considered separately than diffuse absorbance present in the rest of the tissue. The optical density of the epidermal absorption can be subtracted linearly from the total optical density of the skin, since the effect on R is linear.

Light is attenuated as it passes through the epidermis. The reflectance from the skin can be expressed as the product of two components, namely the reflectance of the dermis, $R_{dermis}$, and a term specifying the attenuation of light by the epidermis:

$$R_{skin} \approx R_{dermis} \exp(-\mu_{a.epidermis} <L>_{epidermis}) \quad (3\text{-}30)$$

where the term $\exp(-\mu_{a.epidermis}<L>_{epidermis})$, describes the attenuation of light in the epidermis, and where $<L>_{epidermis}$ is the average pathlength of photons in the epidermis before remission. Therefore, the effect of absorption in the epidermis on the reflection from the skin is much simpler to describe mathematically than that of absorption in the dermis.

Equation 3-30 can be rewritten as:

$$\ln(R_{skin}) \approx \ln(R_{dermis}) - (-\mu_a\ _{epidermis} <L>_{epidermis}) \quad (3\text{-}31)$$

FIG. 16 shows the relationship between the log of reflectance from the skin and the epidermal absorption, as predicted by Monte Carlo computer simulations. A similar relationship (not shown) exists between the log of the reflectance measured with the optical patch, f*M, and the epidermal absorption, since f does not vary significantly with epidermal absorption. Since the relationship between ln(R) and $\mu_a\ _{epidermis}$ is linear, Equations 3-30 and 3-31 appear to be good approximations of the relationships between measured reflectance from the skin and the epidermal absorption. The slope of the plot of $\ln(R_{skin})$ vs $\mu_a\ _{epidermis}$, shown in FIG. 16, is equal to $<L>_{epidermis}$. The average pathlength, $<L>_{epidermis}$ in the Monte Carlo model shown in FIG. 16 is equal to 186.3 µm, or about 3.72 time the thickness of the epidermis.

3.6 Determining Absorbance From Measured Reflection

The collection efficiency, F*, of an optical patch with a fixed geometry, has been shown in subsection 3.4 to be dependent in a predictable manner on $\mu_a$ and $\mu_s'$. The relationship between f* and $\mu_a$ and $\mu_s'$ is unique, such that for any given $\mu_a$ and $\mu_s'$ only one solution for F* exists.

A unique relationship also exists between the true reflection, R, and the ratio of $\mu_s'$ to $\mu_a$. The total reflection, R, from a tissue as predicted by diffusion theory is given by [Flock 1989]:

$$R = \frac{a'}{1 + 2k(1-a') + \left(1 + \frac{2k}{3}\right)\sqrt{3(1-a')}} \quad (3\text{-}32)$$

where a' is the reduced albedo [$a' = \mu_s'/(\mu_a + \mu_s')$], and where $$k = \frac{1 + r_{int}}{1 - r_{int}} \quad (3\text{-}33)$$

where $r_{int}$ is the total internal reflectance due to the index of refraction mismatch (air/skin) at the surface, and is empirically related to the tissue refractive index, n:

$$r_{int} = -1.440n^{-2} + 0.710n^{-1} + 0.668 + 0.0636n \quad (3\text{-}34)$$

Alternately, the total reflection from a tissue is predicted by Monte Carlo computer simulations, and is equal to [Jacques 1989a]:

$$R = C_0 + C_1 \log_{10}(N) + C_2 \log_{10}^2(N) + C_3 \log_{10}^3(N) \quad (3\text{-}35)$$

-continued where $$N = \frac{\mu_s'}{\mu_s} \quad (3\text{-}36)$$

and $C_0 = 0.057, C_1 = 0.1284, C_2 = 0.138, C_3 = -0.027$ for a tissue refractive index of 1.37. In both equations, there is an assumption of a smooth air/tissue interface. The role of skin surface roughness on $r_{int}$ is not yet investigated.

Diffusion theory and Monte Carlo calculations of total reflection R, shown above in Equations 3-32, and 3-35, agree well for a wide range of optical properties. The Monte Carlo equations are selected for calculations since they are more accurate when the optical properties have a low albedo and reflectance is less than 0.40.

Figure 18:
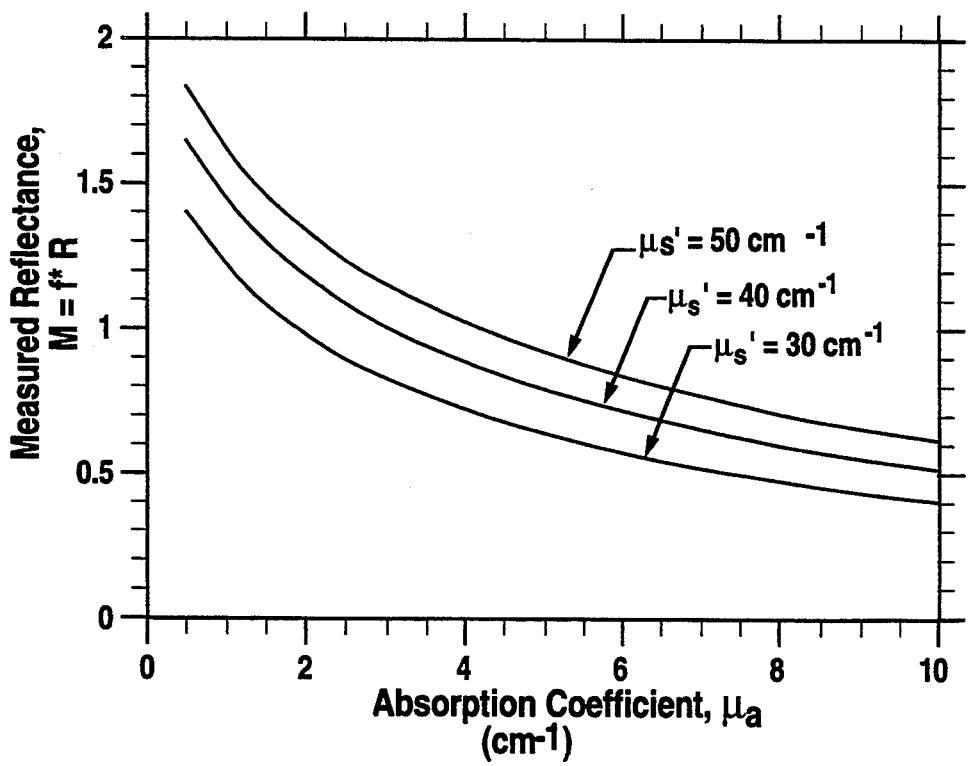
FIG. 18 is a graph of measured reflection, predicted by Monte Carlo simulations, as a function of absorption coefficient.

Since, recalling Equation 3-12, $$M = f^* R = \frac{fR}{f_{standard} R_{standard}} \quad (3\text{-}37)$$

and both f and R are predictable functions of $\mu_a$ and $\mu_s'$, then M can always be predicted from $\mu_a$ and $\mu_s'$ for a given standard. FIG. 18 illustrates this and shows the effect $\mu_a$ has on the measured reflection M at 630 nm for three different scattering coefficients.

The absorption coefficient, $\mu_a$, can not be solved uniquely by reduction of the above equations. However, if one knows M, $\mu_s'$, and the $f_{standard}R_{standard}$ at which the measurement was made, the absorption coefficient can be obtained by implementation of an iterative procedure. This iterative procedure is illustrated in FIG. 19, and is described below.

Figure 19:
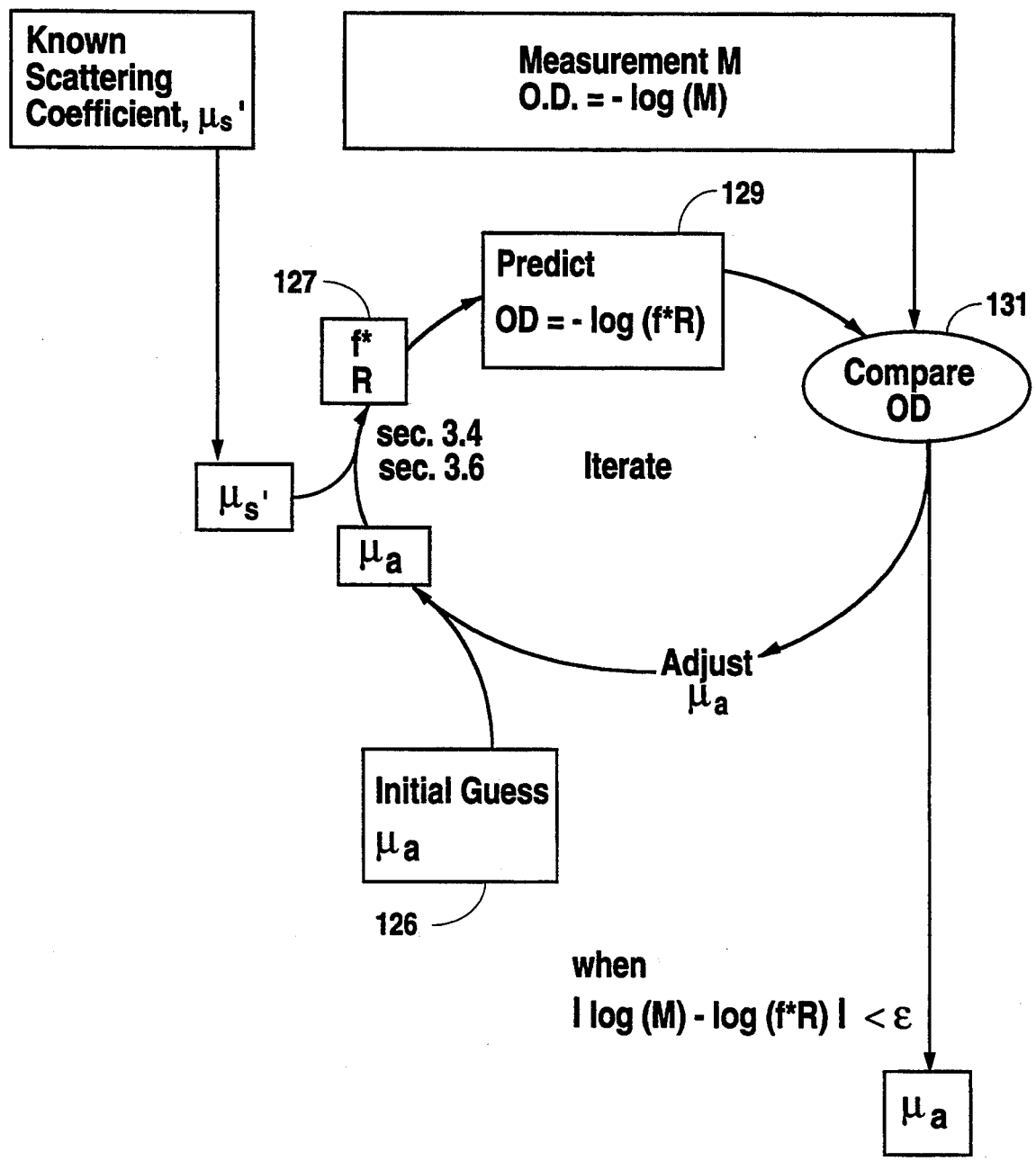
FIG. 19 is a flow chart of the iterative method of the present invention to use optical patch measurement to determine absorption coefficient in a tissue of known scattering properties.

Referring to FIG. 19, the optical patch measurement, M, and the reduced scattering coefficient, $\mu_s'$, are known for the tissue being measured. An initial starting value for $\mu_a$ is guessed in block 126, and the value of f and R are calculated by means of Equations 3-27 and 3-28, and Equations 3-32 and 3-33 respectively in block 127. The value of f* is determined by dividing f by the value of $f_{standard}R_{standard}$ at the particular wavelength used. The negative log of the product f*R, $-\log(f^*R)$, is the predicted optical density and is compared to the measured optical density, $-\log(M)$ in block 129. If $-\log(f^*R)$ is less than $-\log(M)$ as determined by block 131, then the value of $\mu_a$ is increased slightly, an if $-\text{long}(f^*R)$ is greater than $-\log(M)$, then $\mu_a$ is decreased, and the calculation of f* and R are repeated. This procedure is repeated until the value of $-\log(f^*R)$ is equal to the measured, $-\log(M)$, within an assigned tolerance, $\epsilon$. This iterative procedure is implemented in Section 5 to find the diffuse absorbance within a tissue from the measured reflectance.

3.7 Conclusions

Total reflection can be measured by either collecting all the reflected light, or collecting a constant fraction of the reflected light by means of a distant detector. Practical biomedical devices for measuring reflectance, such as the optical patch introduced in chapter 1, collect only a fraction of the reflected light. This collected fraction, f, is dependent on the optical properties of the tissue, and therefore is also wavelength dependent. Correct interpretation of measured reflectance spectra, M(λ), requires knowledge of f(λ) to yield true reflectance spectra R(λ).

The efficiency of the optical patch was determined physically by determining the true reflectance, R, and measured reflectance, M, for a series of phantoms of known optical coefficients. The collection efficiency of the optical patch was found to be dependent on $\delta/\mu_t' d^2$, where $\delta$ is the penetration depth in the measured medium (Equation 3-17), $\mu_t'$ is the total attenuation coefficient (equation 3-18), and d is the diameter of the optical patch.

Knowledge of the collection characteristics of the optical patch, and the dependence of reflectance on the optical coefficients, can be combined to determine the absorption coefficient within a tissue of known scattering coefficients from reflectance measurements with the optical patch.

Section 4
Considerations Of Skin Variation 4.1 Introduction

In Section 3 the importance of optical properties and of measurement device geometry for the interpretation of reflectance signals were discussed. If the optical properties of a tissue, the measurement device geometry, the architecture of structures within the skin, and the relative amounts of different absorbers were fixed, then reflectance spectroscopy algorithms could theoretically be developed empirically without attention to the light transport in tissue. Such analysis has been applied to determine the bilirubin concentration in neonares, and has performed well when measurements were conducted on specific very homogeneous populations but perform poorly with heterogeneous populations [Yamanuchi 1980, Hegyi 1981, Hannemann 1982, Kenny 1984]. The potential success of such techniques are limited due to the variation in skin optical properties and possibly due to variation in the location of different absorbers in the skin. For example, the melanin content, the depth of the blood plexus beneath the surface, and the scattering properties of the skin may vary between subjects. The predominant absorbers in the skin are present in different layers. The melanin is present in the epidermis, the topmost layer of the skin. The blood is predominantly present in the dermal blood plexi. The bilirubin originates in the blood plexus, but seeps into the dermis, and is also taken up by the epidermis [Kapoor 1973]. The absorbers in the different layers, namely diffuse absorbers in the dermis, blood in the blood plexi, and melanin in the epidermis, may have to be considered separately since their effect on the measured reflectance will vary with their depth in the skin.

Consideration of the skin architecture, the possible variations in optical properties between individuals, and the effect these variations will have on the reflectance measurements, will enable development of algorithms that fundamentally are designed to determine the absorption of bilirubin in heterogeneous populations. Blood depth, skin thickness, epidermal absorption, and skin maturity can vary between subjects. To determine the importance of these potential sources of variation on the measured reflectance, they are considered individually in this section.

4.2 Variation In Maturity

In section 3, a significant linear relationship between scattering properties of the skin and gestational maturity was reported at all visible wavelengths. This relationship implies that the measured reflectance will increase with maturity, given that absorption does not vary significantly. The reflection of blue, green, and red light from neonatal skin has been reported to increase with the gestational age of the neonate [Krauss 1976, Ballowitz 1970]. This relationship was reported to hold for neonares of both races up to 32 weeks gestation, and continued to hold within each racial group (black/white) thereafter until term. Changes in reflectance after birth were not studied. Colored filters were used to select the light color. Melanin absorbs light throughout the visible spectrum, and so the observed differences in reflectance between racial groups is due to the melanin. The increase in reflectance with gestational age within each racial group, presumably is due to the increase in scattering properties with gestational maturity (see Section 2.3, 2.3). For the purpose of analysis of the reflected spectra, where one needs to know the scattering properties of the measured skin, it is imperative that variations in the scattering properties of a neonate's skin can be determined regardless of the amount of melanin pigmentation.

The measured optical density of the skin, OD, between 650 and 750 nm can be extrapolated to 837 nm, $OD_{837}$. OD is defined as:

$$OD = -\log[f^* R]) \quad (4\text{-}1a)$$

The extrapolated dermal reflection at 837 nm, $R_{837}$, can be calculated from $OD_{837}$ as:

$$f^* R_{837} = 10^{-OD_{837}} \quad (4\text{-}1b)$$

This extrapolated value, $f^* R_{837}$, is invariant with the melanin pigmentation in human skin. Therefore, $R_{837}$ is dependent only on the scattering properties of the skin, and the relative maturity of the skin can be determined from the optical density spectra of variably pigmented subjects. The scattering at any wavelength of interest can then be estimated since the scattering spectrum of neonatal skin is known for varying gestational maturities (see Section 2). The changes in scattering coefficient versus wavelength for neonates of different gestational maturities due to changes in the sizes of collagen fiber bundles are accounted for by use of the empirical equations of $\mu_s'(\lambda)$ as a function of maturity (eqs. 2-5, 2-6, and 2-7).

4.2.1 Observed Variability In Maturity

Figure 20:
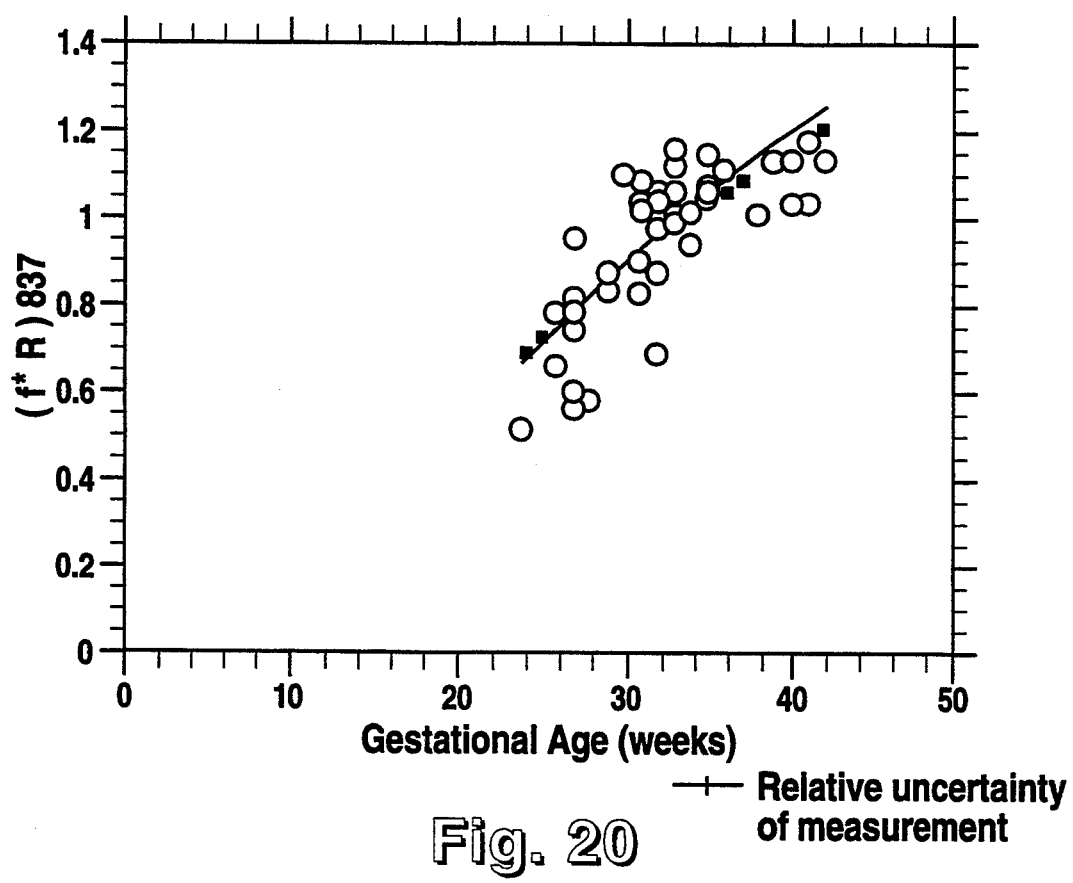
FIG. 20 is a graph of measured extrapolated reflection values at 837 nm as a function of gestational age.

FIG. 20 shows $f^* R_{837}$ measured on the abdomen of 48 newborn infants versus their gestational age. The gestational age was determined conventionally by dates, or by the modified Dubowitz criteria when maternal dates were unreliable [Kirkpatrick 1983]. As discussed in section 3, the reflectance of tissue is dependent on the ratio of $\mu_s'$ to $\mu_a$ [Wilson 1990]. In the operative range between 20% and 70% reflectance, the following linear relationship can be used to approximate reflectance from a material with optical coefficients $\mu_a$ and $\mu_s'$. In Equations 4-2 through 4-4 $C_0$, $C_1$, $C_2$, and $C_3$ stand for constants.

$$\text{Reflection} \approx C_1 \log\left(\frac{\mu_s'}{\mu_a}\right) + C_0 \quad (4\text{-}2a)$$

where $C_0 = -0.5$, and $C_1 = 0.375$ (based on approximations of Equations 3.32 and 3.35).

The scattering coefficient of neonatal skin at all wavelengths increases linearly with gestational age, (see FIG. 4), and can be expressed as:

$$\mu_s \approx C_2 \text{ Maturity} \quad (4\text{-}2b)$$

where $C_2 \approx 0.47$ cm$^{-1}$/week of gestational age.

Therefore the extrapolated measurement, $f^*R_{837}$, can be expected to increase with the logarithm of gestational age:

$$f^* \text{ Reflection} \approx f^* C_1 \log(\text{Maturity}) + f^* C_3 \quad (4\text{-}3)$$

where $C_3 = C_1 \log C_2 - C_1 \log \mu_a + C_0$. The collection efficiency of the optical patch of skin relative to teflon, $f^*$, at 837 nm is about 5.7 (measured on human skin in a method similar to that explained in Subsection 3.3), and $\mu_a$ at 837 nm is believed to be in the range of 0.25 cm$^{-1}$, based on extrapolation of FIG. 5. Placing the approximate values in all the constants above, C0, C1, C2, and $f^*$, the extrapolated reflection at 837 nm can be approximated as:

$$f^* R_{837} \approx 2.14 \log(\text{maturity}) - 2.26 \quad (4\text{-}4a)$$

This relationship is also shown in FIG. 20. From the above calculations, we find that it is reasonable to expect a logarithmic relationship between maturity and $f^*R_{837}$. Therefore, we chose to fit the available data with a logarithmic fit ($r=0.79$, $p<0.001$), also shown in FIG. 20:

$$f^* R_{837} \approx 2.43 \log(\text{maturity}) - 2.72 \quad (4\text{-}4b)$$

Figure 21:
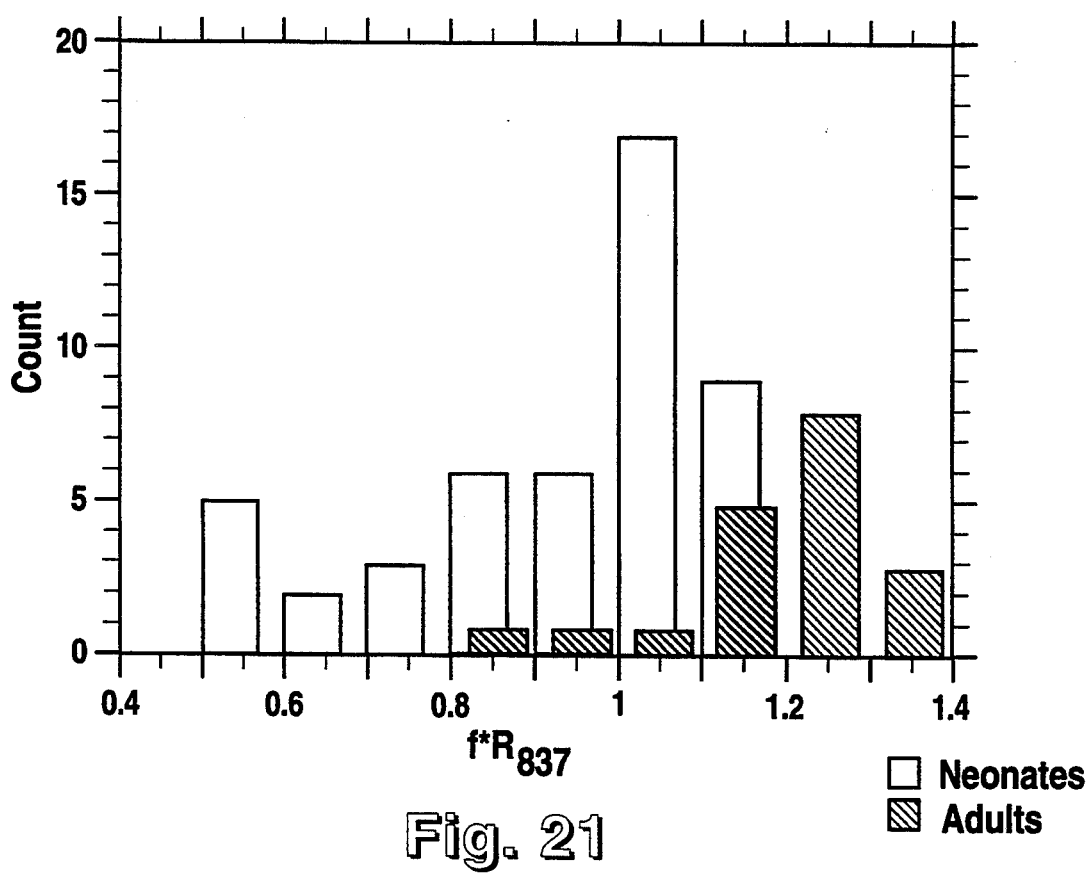
FIG. 21 is a graph of the distribution of measured extrapolated reflection values at 837 nm for neonates and adults.

The above relationship may be used to supplement existing tests to determine the gestational age, or level of maturity, of newborn infants. FIG. 20 also shows the typical error in the reflectance measurement, and the uncertainty with which the gestational age of the infant is known before comparison with reflectance measurements. This shows that the error in the measurement is small relative to the gestational age uncertainty evaluated by conventional means. The error in clinical assessment could possibly account for the dispersion of data in FIG. 20. The actual variation in $f^*R$ versus age is not yet known, since clinical age assessment is only an estimate. The reflectance measurements can provide a subjective evaluation of gestational maturity that is not vulnerable to objective evaluation by the user. FIG. 21 shows the distribution of extrapolated $f$-$R_{837}$ values measured on a group of neonates in the intensive care unit (gestational age range: 24–42 weeks), and also measured on a group of adults. As seen in the figure, the adult population appear to have higher extrapolated $f^*R_{837}$ values than does the neonatal population.

4.2.2 Changes In Reflectance With Added Absorber

Changes in the maturity of the skin being measured will have an effect on the interpretation of the reflected spectra when attempting to analyze the absorption within the skin. Differences in the scattering of the skin will result in a change in the underlying dermal reflectance as explained above, but more importantly, will alter the change in reflection, $\Delta R$, due to the addition of absorber, $\Delta \mu_a$, within the skin [Saidi 1990]. Scattering affects the pathlength of photons in skin, which in turn affect the relationship between $\Delta \mu_a$ and $\Delta R$. Therefore knowledge of skin optics is important in order to interpret the observed changes in reflectance in terms of $\Delta \mu_a$ due to bilirubin or blood. We can determine how the optical density changes, $\Delta O.D.$, due to changes in $\Delta \mu_a$, and how this relationship is dependent on the background optical properties. Consequently, we determine the uncertainty with which we interpret changes in O.D. due to uncertainty in our knowledge of background $\mu_a$ and $\mu_s'$.

The reflection measured at the skin surface can be expressed as:

$$R = e^{-\mu_a L_{eff}} \quad (4\text{-}5)$$

where $\mu_a$ is the absorption coefficient within the tissue, and $L_{eff}$ is defined as the effective pathlength of the reflected photons [Saidi 1990, Jacques 1989]. Optical density, $(O.D. = -\log_{10}[R])$, is therefore:

$$O.D. = \frac{\mu_a L_{eff}}{\ln(10)} \quad (4\text{-}6)$$

It is important to note that $L_{eff}$ is not equal to $<L>$, the arithmetic mean of the pathlengths of emitted photons in the tissue. Changes in the optical density, $\Delta O.D.$, seen with changes in absorption, $\Delta \mu_a$, are:

$$\frac{\Delta O.D.}{\Delta \mu_a} = \frac{L_{eff}}{\ln(10)} + \frac{\Delta L_{eff}}{\Delta \mu_a} \frac{\mu_a}{\ln(10)} \quad (4\text{-}7)$$

Figure 22:
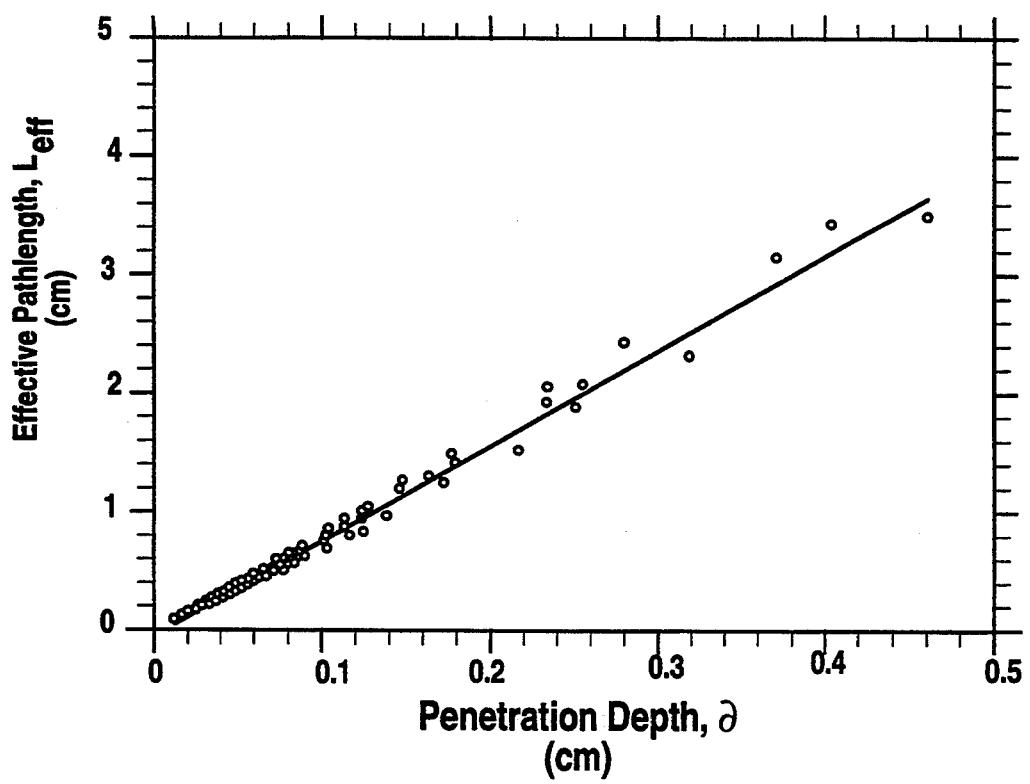
FIG. 22 is a graph of the defective path length as a function of effective penetration depth.

Therefore the changes seen in skin optical density due to the addition of bilirubin has to be interpreted in the context of the $L_{eff}$ operative in the tissue measured. The effective pathlength, as shown in FIG. 22, was found to be directly dependent on the penetration depth of light in the tissue, and so is dependent on both $\mu_a$ and $\mu_s'$. The penetration depth, $\delta$, of light in tissue was defined in Equation 2-4.

FIG. 22 was generated by diffusion theory calculations of R, (Equation 3-32), for various $\mu_a$ and $\mu_s'$, and by calculation of $L_{eff}$ (by Equations 4-5, and 2-4). The linear fit of the data shown in FIG. 22 relating $L_{eff}$ to $\delta$ is:

$$L_{eff} = -0.040112 + 7.9822 \, \delta \quad (4\text{-}8)$$

The coefficient of regression, R, is 0.996, and both $L_{eff}$ and $\delta$ refer to distances, and are expressed here in units of centimeters. The relationship discovered above can be approximated as:

$$L_{eff} = 8 \, \delta \quad (4\text{-}9)$$

and based on these observations, one can approximate the reflectance, R, to be dependent on the $\mu_a$ and $\delta$ as:

$$R \approx \exp(-8 \, \mu_a \delta) \quad (4\text{-}10)$$

Substitution of Equations 2-4 and 4-9 into Equation 4-7 and differentiating to the limit as $\Delta \mu_a$ approaches zero, and then as $\Delta \mu_s'$ approaches zero, one obtains:

$$\frac{dO.D.}{d\mu_a} = \frac{4}{\ln(10)} (2\delta - \delta^3 \mu_a [6 \mu_a + 3 \mu_s']) \quad (4\text{-}11)$$

and $$\frac{dO.D.}{d\mu_s'} = \frac{-12 \mu_a \delta^3}{\ln(10)} \quad (4\text{-}12)$$

Figure 23:
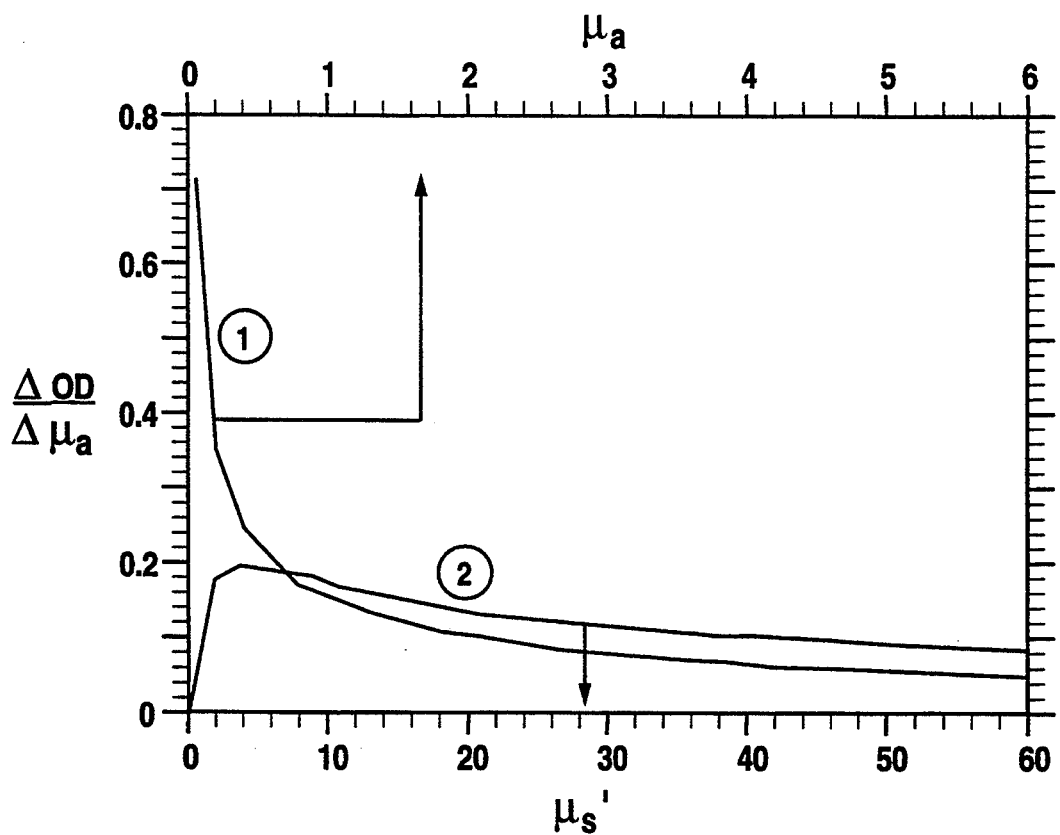
FIG. 23 is a graph of the change of optical density due to the addition of unit absorption, as a function of the absorption and scattering coefficients in tissue.

These expressions indicate the sensitivity of O.D. due to uncertainty in $\mu_a$ and $\mu_s'$. From Equation 4-11, one learns that the change in optical density due to addition of absorber into a medium is dependent on both the $\mu_a$ and $\mu_s'$ in the tissue. Therefore, the addition of absorber into a tissue with one set of optical properties will not yield the same optical density change as the addition of absorber into another tissue with different absorption or scattering coefficients. FIG. 23 shows the change in optical density due to the addition of unit absorption, as a function of the absorption and scattering coefficients in the tissue. In the normal range of optical properties in tissues, the change in optical density of a tissue due to the addition of absorption will decrease as the absorption and scattering coefficients of the tissue increase. Therefore, for example, a skin sample highly perfused with blood will show a smaller change in optical density due to the addition of bilirubin, than will a skin sample with little blood, and the baseline skin optical properties are very important for analyzing observed optical density changes. This phenomena is illustrated further in section 5.

Equations 4-11, and 4-12, are also useful for appreciating some of the uncertainty with which the optical density is predicted due to uncertainty in the absorption or scattering coefficients in the tissue. For example typical optical properties in the skin of a jaundiced neonate at 460 nm are 3 cm$^{-1}$ and 40 cm$^{-1}$ for $\mu_a$ and $\mu_s'$ respectively, and the uncertainty in these two values are 0.3 cm$^{-1}$ and 6 cm$^{-1}$. The resulting uncertainties in the optical density due the uncertainties in absorption and scattering coefficients are (calculated by Equations 4-11, and 4-12):

$$\frac{dOD}{d\mu_a} \Delta\mu_a = (0.0821)(0.3) = 0.0246$$

$$\frac{dOD}{d\mu_s'} \Delta\mu_s' = (-0.0062)(6) = -0.0370$$

Therefore, uncertainty in both absorption and scattering are important in leading to uncertainty in predicting the background optical density of the skin. Interpretation of O.D. Spectra in terms of bilirubin or blood content are equally affected by uncertainty in the background skin optical properties of $\mu_a$ and $\mu_s'$.

4.3 Variation In Melanin

Melanin pigmentation of the skin is what differentiates skin color between individuals. The melanin absorption spectra extends throughout the visible region, and the profile exhibits decreasing absorption from the blue to the red wavelengths [Jacques 1991, Kollias 1987, Blois 1966]. The melanin is usually present only in the epidermis, (see Section 1), and has to be considered separately from other absorbers that are located in the blood layer or the dermis. Melanin is an important absorber to be considered in transcutaneous bilirubinometry since melanin in the epidermis can lower the measured reflectance significantly.

The reflectance of skin has been found to differ markedly between neonates of different races after 32 weeks of gestational age [Krauss 1976]. This difference is due to differences in their melanin pigmentation. In 48 neonates that we have measured in which the gestational age varied from 24 to 42 weeks, the reflectance in the red (650 nm) was found to vary significantly between infants of different ages after about 33 weeks gestational age.

4.3.1 The Absorption Spectrum Of Melanin

There are some differences in the reported absorption spectra of melanin [Jacques 1991, Rosen 1990, Kollias 1985, Blois 1966]. Some of the differences in the reported spectra have been attributed to different molecular forms of melanin. As discussed in section 3, melanin pigmentation essentially does not affect the collection efficiency of the optical patch, f*, since the melanin is usually present only in the epidermis. Therefore the collection efficiency of the optical patch can be factored out when attempting to characterize the melanin absorption spectra by reflectance spectroscopy of pigmented versus unpigmented sites. The following equations illustrate how the collection efficiency factor, f*, can be factored out when measuring the change in optical density due to melanin, $\Delta OD_{melanin}$, when comparing the reflection of a pigmented skin site, $R_{pig.}$, to that of a non-pigmented skin site (e.g. vitiligo), $R_{vit.}$ as seen in the following equations.

$$\begin{aligned}
\Delta OD_{melanin} &= OD_{pig.} - OD_{vit.} & (4\text{-}13)\\
&= [-\log(f^*R_{pig.})] - [-\log(f^*R_{vit.})] & (4\text{-}14a)\\
&= -\log\left(\frac{f^*R_{pig.}}{f^*R_{vit.}}\right) & (4\text{-}14b)\\
&= \log\left(\frac{R_{vit.}}{R_{pig.}}\right) & (4\text{-}14c)
\end{aligned}$$

With the spectrophotometer and optical patch, the optical density spectra of the dorsal and ventral aspect of the forearm of 17 adults were measured. The dorsal and ventral aspects are differentially pigmented, and differences in the spectra are attributed to differences in melanin pigmentation. Five of the 17 spectra were discarded because of visible influence of blood on the reflectance spectra. This can occur where there is a higher blood concentration in one aspect of the forearm than the other. The $\Delta OD_{melanin}$ was calculated using Equation 4-14c.

Figure 24:
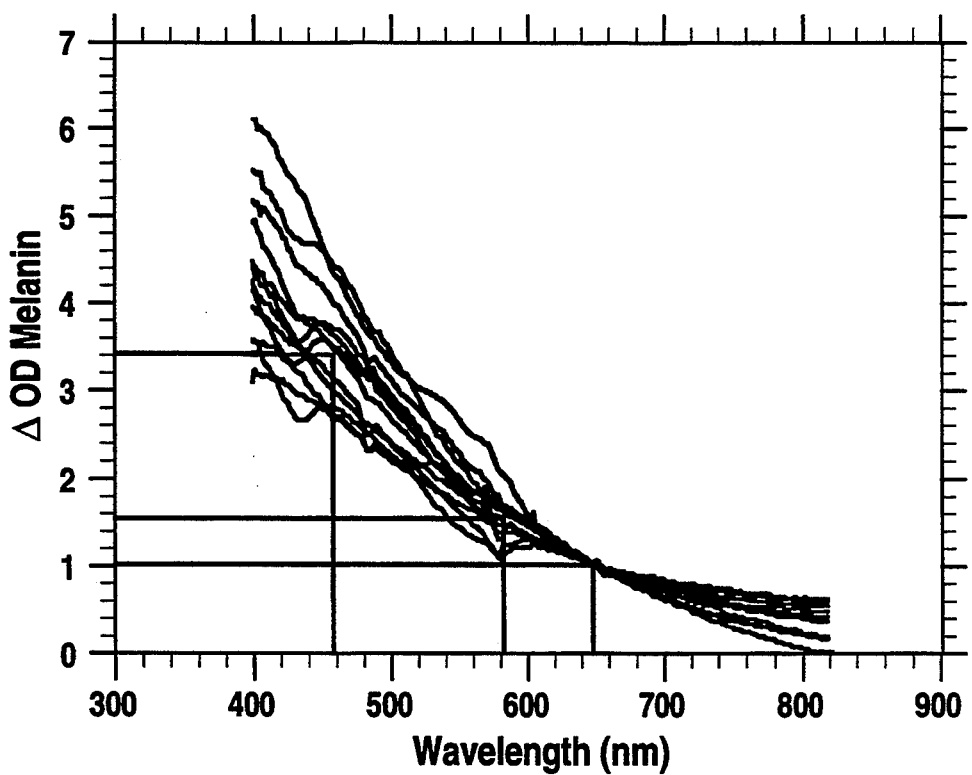
FIG. 24 is a graph of the in vivo melanin optical density spectra measured with the optical patch of FIG. 8A.

The average of the melanin absorption spectra measured is shown in FIG. 24. This spectra correlates well to other measurements of the melanin spectra reported in the literature [Kolias 1985, Blois 1966]. The melanin absorption spectra was found to essentially decrease linearly with wavelength in the visible region. Since the melanin absorption shown varies across the visible spectra in order of magnitudes, variation in the pigmentation will cause large absolute changes in the absorption at shorter wavelengths, but the same magnitude changes will cause relatively minuscule absolute changes in the very long wavelengths (>800). The melanin pigmentation measured in the far red wavelength range (650–750 nm) appears to have a pivot point at around 837 nm. This is in agreement with observations on melanin pigmentation reported in the literature [Kolias 1985] from the absorption spectrum of various concentrations of Dopa-Melanin. Kolias went on to show that the melanin absorption spectra between 620 and 720 nm, measured in vivo as discussed, can be expressed as:

$$a(\lambda) \approx c\left[1 - \frac{\lambda}{837\text{ nm}}\right] \quad (4\text{-}15)$$

where c is a scalar that is related to the concentration of melanin in the skin and $\lambda$ is the wavelength in nm. From the above equation it is determined that extrapolation of the in vivo melanin absorption spectra will appear as zero absorption at around 840 nm.

Figure 25:
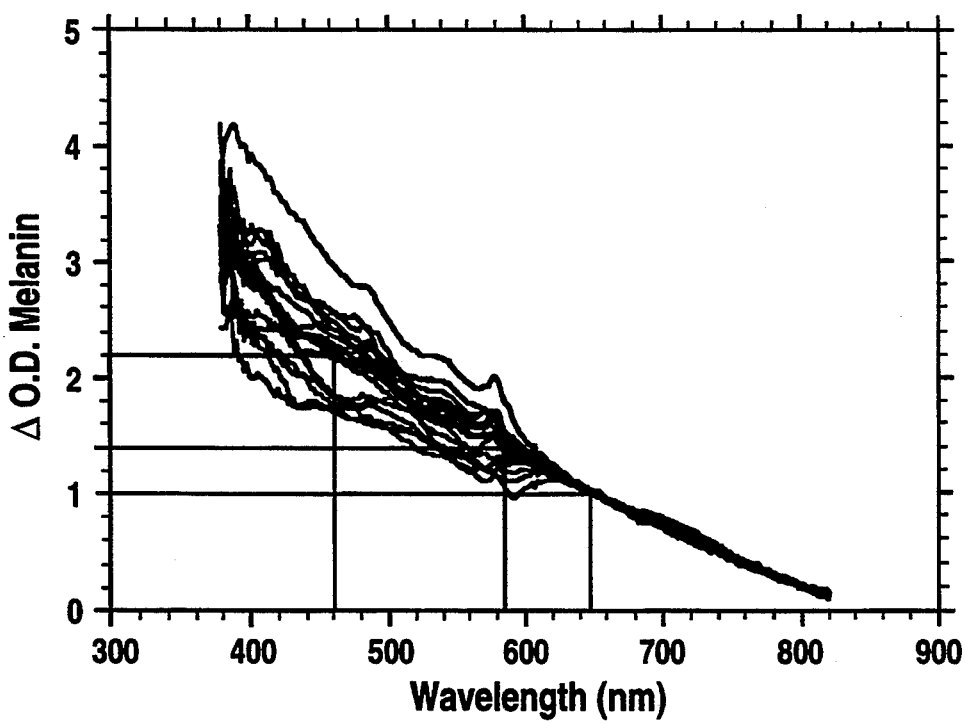
FIG. 25 is a graph of the in vivo melanin optical density spectra measured on neonates with the optical patch of FIG. 8A.

The melanin spectrum in neonates was also measured. The measured optical density spectra from seventeen neonates were subtracted from the spectra measured on neonates with higher melanin pigmentation. The difference between these spectra is due to melanin. The difference in maturity in the neonate pairs was removed by subtraction of the extrapolated optical density at 837 nm, $OD_{837}$, from the entire melanin spectrum. The extrapolated value at 837 nm for each of the melanin spectra measured was therefore equal to zero. The melanin optical density spectra were then all normalized to unity at 650 nm, and averaged. FIG. 25 shows the neonates' melanin optical density spectra measured in this way, and the average of these spectra. It can be seen that below about 600 nm, there is a wide variability in the measured melanin optical density, due to variations in the blood content in the skin of the neonate pairs measured. These variations are expected to average to zero, and the average melanin spectrum, shown in bold, is a good representation of the optical density difference due to melanin.

The melanin spectrum measured on neonates, shown in FIG. 25, increases more gradually at lower wavelengths than the melanin spectrum measured on adults, shown in FIG. 25. The reason for this difference in the absorbance spectra is not clear, but may be due to the fact that neonates have not been subjected to actinic damage to the skin that occurs with age.

4.3.2 Measurement Of The Melanin Content In Skin

Figure 26:
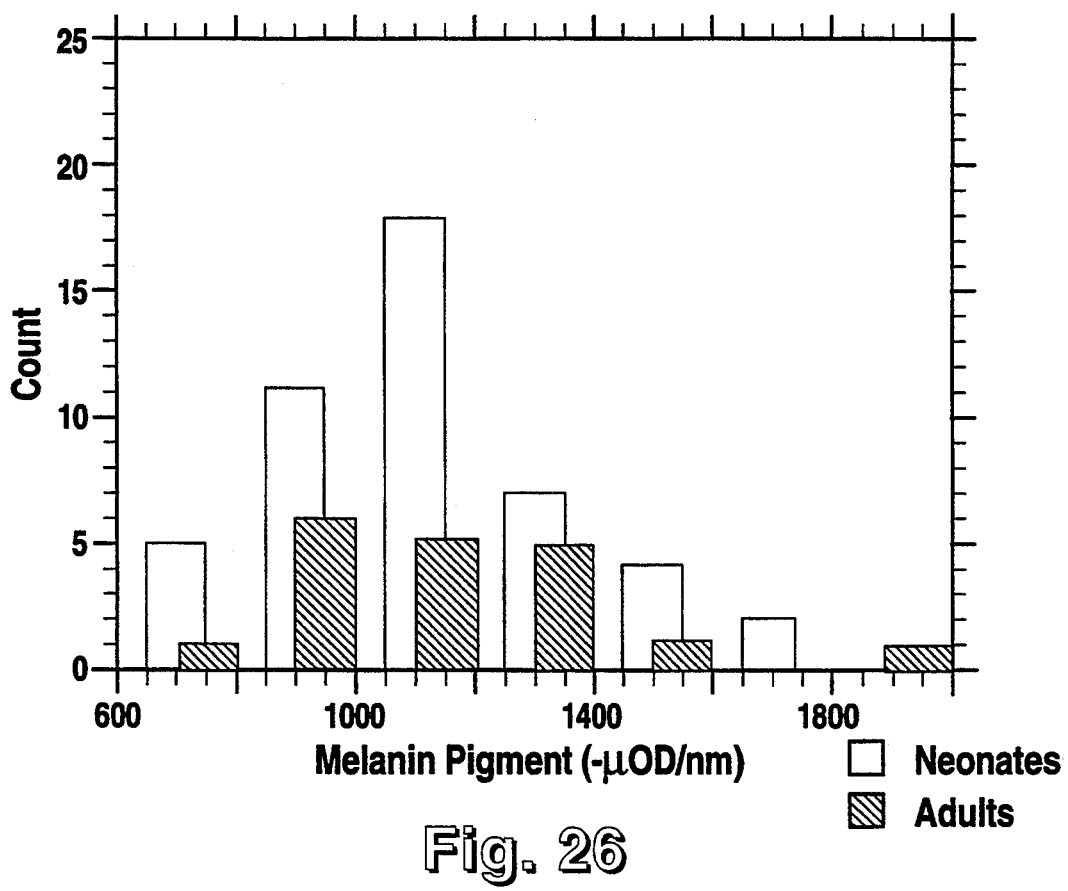
FIG. 26 is a graph of the demographic distribution of melanin pigmentation, measured as the negative slope of the optical density spectrum.

Based on the above observations, the melanin pigmentation has been reported to be determined by the slope of the optical density spectra between 650 and 750 nm [Kolias 1985, Rosen 1990]. FIG. 26 shows the melanin content of 47 neonates and 19 adults measured in this manner. There does not appear to be a significant variation in the melanin pigmentation between neonates and adults.

The slope of the optical density spectra is expected to vary with the nature of the scattering coefficient of a tissue to wavelength (see Section 3). When the collagen fiber bundles in the dermis are smaller on average (such as in a less mature infant), the scattering coefficient is expected to fall off more rapidly with increasing wavelength compared to an older neonate with larger collagen fibers. This more rapid decrease in scattering will cause the reflectance spectrum to also fall more rapidly, and so lower the magnitude of the slope of the optical density spectrum regardless of the pigmentation. This will alter the pigmentation determinations that are performed by measuring the slope only.

An alternate method to determine the melanin concentration in skin that is not sensitive to the maturity of the skin is to determine the difference between the expected reflectance and the true reflectance at 650 nm. The expected reflectance, $R_{expected}$, of the dermis at 650 nm can be calculated since the value of the 650-nm absorption coefficient of skin has been measured, and the 650-nm scattering coefficient of skin is known for any given maturity. The maturity is determined by extrapolation to 837 nm as explained in Subsection 4.2. The blood and bilirubin are not significant absorbers at 650 nm, and so they are not expected to significantly influence the reflectance of the skin at that wavelength. The collection efficiency of the optical patch can also be calculated at 650 nm, since both the absorption and the scattering coefficients are known. The difference between expected optical density, $(-\log(f^* R_{expected}))$, and the measured optical density $(-\log(M))$, is due only to the melanin absorption at 650 nm. This method of measuring the melanin content is employed in the algorithm to determine the cutaneous bilirubin content developed in section 5.

The expected reflection at 650 nm, $R_{expected}(650)$, can be calculated by Equation 3-35 where the absorption coefficient at 650 nm is equal to 0.55 (from FIG. 5 and Equation 2-9). From equations 2-5 through 2-7, the expression for the scattering coefficient at 650 nm can be expressed as:

$$\mu_s'(650) = Y_{int} + m(maturity) \qquad (4\text{-}16)$$

where the maturity is specified in weeks, and Yint and m are specified by Equations 2-6 and 2-7.

The difference between the measured optical density, $-\log(M)$, and the calculated optical density, $-\log(f^*R_{expected})$, is therefore equal to the melanin optical density, $OD_{melanin}$:

$$OD_{melanin} = -\log(M) - (-\log(f^*R_{expected})) \qquad (4\text{-}17)$$

4.4 Variation In Blood Content And Depth

4.4.1 Blood Supply Of The Skin

The dermis is nutritionally supplied by an irregular network of blood vessels. The blood vessels in the skin are usually in great excess relative to the requirements of the tissue they serve, partially because of the cutaneous vessels' function as thermal regulators. Irregularity is the rule for these blood vessels in the skin, yet they tend to be distributed in both superficial and deep plexi. These two plexi have been shown to be interconnected, and are both part of the total cutaneous network that also supplies the hypodermis, the fatty collagenous layer below the dermis [Montagna 1974, Winkelmann 1961]. Other smaller plexi between the superficial and deep plexi, including the second and third venous plexi, ensure that the blood has continuous distribution throughout the skin [Lewis 1927].

4.4.2 Variation In Blood Content

The amount of blood present in the skin can vary between infants, site of measurement, and current physiological state of the infant. To determine how variation in blood content affects the reflectance from the skin, the blood in the skin was modeled to be present only in the papillary dermis as a plexus. The depth of the papillary plexus was varied in the model between 50 and 500 µm, and the blood content in the papillary plexus was varied between 5% and 15% of the plexus volume. Monte Carlo simulations (See Section 3 for introduction) were used to study the reflectance measured at the skin surface due to the variation in the blood content and depth in 30-week mature skin (see Subsection 4.2). Three wavelengths (420, 460 and 585 nm) were modeled.

Figure 27:
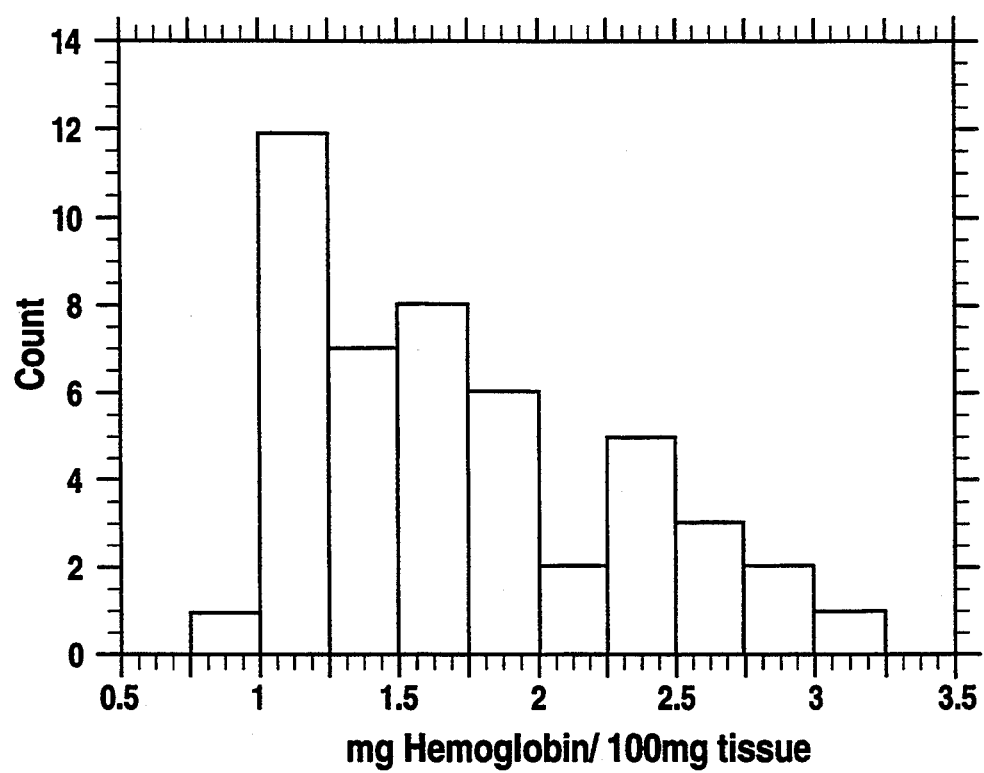
FIG. 27 is a graph of the demographic distribution of blood content in the skin of 47 neonates.

The quantity of blood was found to increase the optical density measured at the skin surface at all three wavelengths. At 585 nm, blood is the only significant variable absorber in the dermis, and so the relationship between 585-nm optical density and blood quantity can be used to determine the blood content of the skin. FIG. 27 shows the cutaneous blood concentration measured on 47 neonates in the intensive care unit. The method by which the cutaneous blood concentration is determined from the measured reflectance is explained in Section 5.

4.4.3 Variation In Effective Depth Of The Blood

The blood in the skin is not truly localized in a 50-μm papillary plexus, however there may be variations in the average depth of the blood beneath the surface. A Monte Carlo model was used to study if any variations in the blood depth, within an expected range, will influence the optical measurements performed at the skin surface. Because shorter wavelengths have shallower penetration depth than longer wavelength, the optical density observed with blue light will vary more strongly with changes in the depth of the blood layer than will the optical density observed with red light. The effect of depth on the observed optical density diminishes with longer wavelengths as the penetration depth increases.

To determine the importance of the depth of the blood below the skin surface, the blood in the skin was modeled, and the resulting reflection calculated by Monte Carlo computer simulations, as explained in section 4.4.2.

Figure 28:
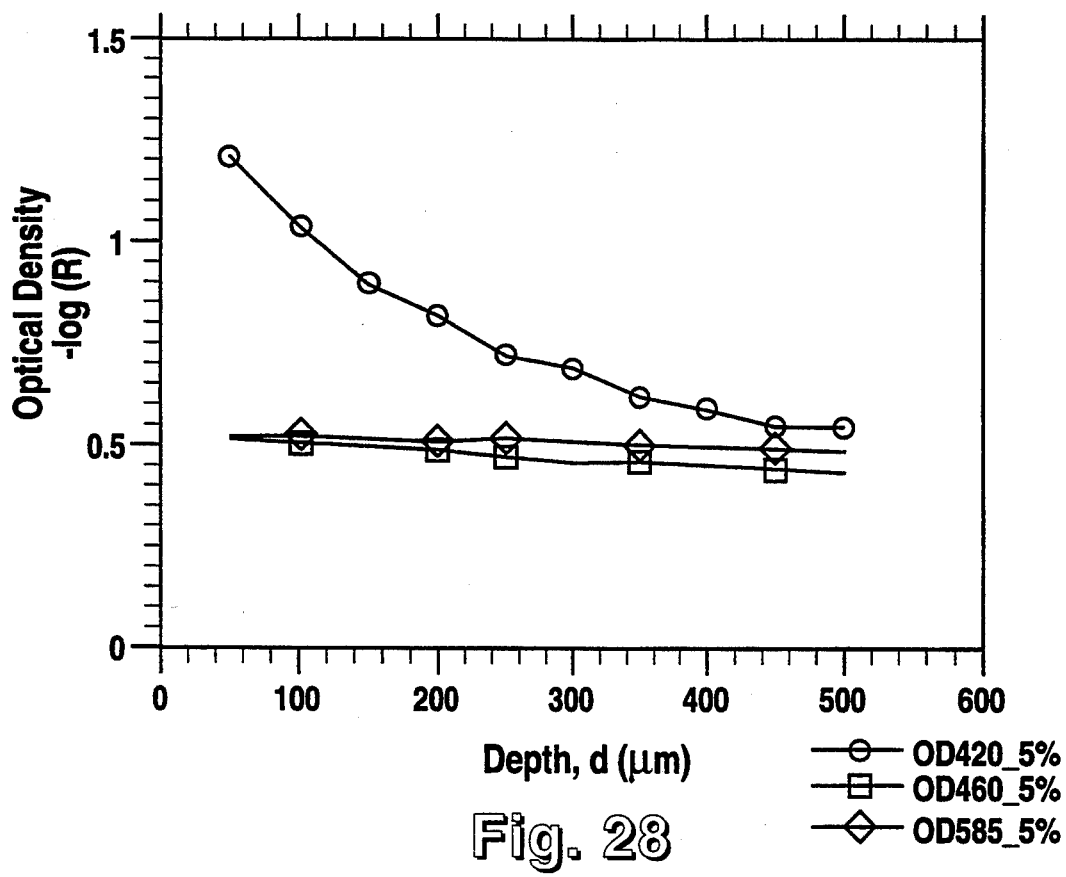
FIG. 28 is a graph of the optical density predicted by Monte Carlo computer simulations, in accordance with the present invention, is a function of depth of the blood in the skin.
Figure 29:
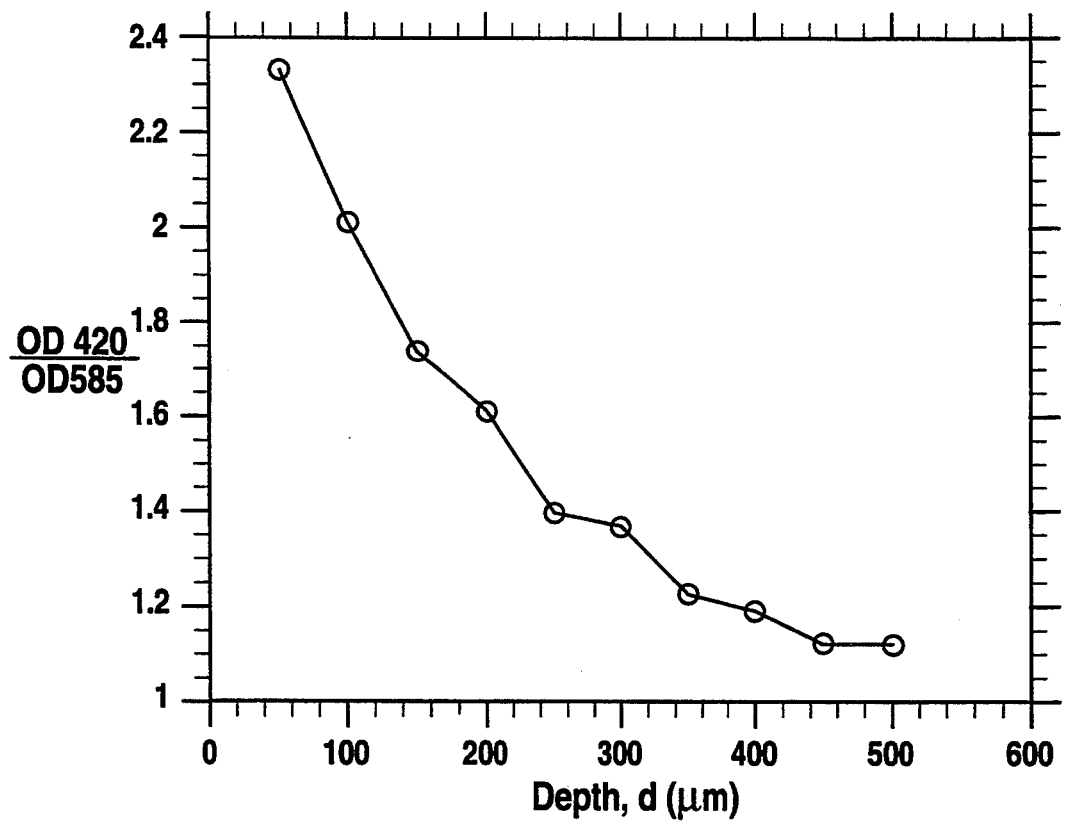
FIG. 29 is a graph of the ratio of the blood in the skin at two measuring wavelengths, as a function of the depth of the blood layer.

FIG. 28 shows the predicted optical density, defined as $-\log_{10}(R)$, at 420, 460 and 585 nm versus the depth of the papillary plexus beneath the skin surface. The results shown are for 5% blood content by volume in the papillary dermis. As can be seen from this figure, the depth of the blood appears to have an important effect on the observed optical density of 420-nm light, however, the depth of the blood does not appear to have a strong effect on the optical density observed at either 460 or 585 nm. This implies that there will not be significant variation in the optical density at 460 or 585 nm due to variation in the blood depth. The details of vascular structure are not expected to affect deduction of blood volume from the optical density spectra. FIG. 29 shows the ratio of optical density at 420 relative to that at 585 nm, as a function of papillary plexus depth. The ratio is obtained by dividing the optical density predicted by Monte Carlo for 420-nm light, by the optical density predicted for 585-nm light.

Figure 30:
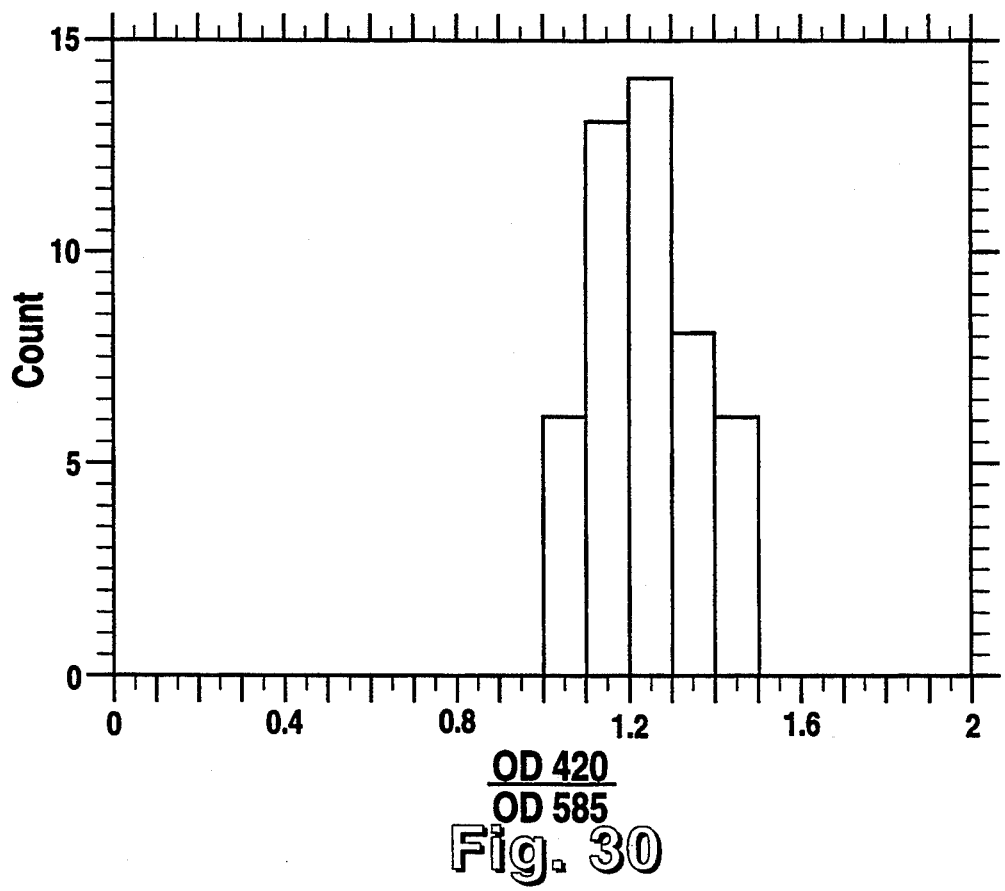
FIG. 30 is a graph of the measured distribution of the ratio of the optical density at 420 nm relative to the optical density at 585 nm.

FIG. 30 shows the distribution of the ratio of optical density at 420 nm relative to that at 585 nm, measured on 47 neonates. As can be inferred from FIG. 28, a typical ratio of 1.2 between OD420 and OD585 corresponds to an average blood depth of 250 μm beneath the surface of the skin.

4.4.4 Conclusions

Based on these observation, one can conclude that the optical densities of the skin at 460 and 585 nm are proportional to blood content and insensitive to its location in the skin. This fact makes analysis of reflectance spectra easier since the blood content can be calculated at 585 nm irrespective of papillary plexi location, and the total bilirubin content in the skin can be determined from the measured reflectance despite any spatial variation that may exist in its distribution within the skin.

4.5 Variation In Skin Thickness

Figure 31:
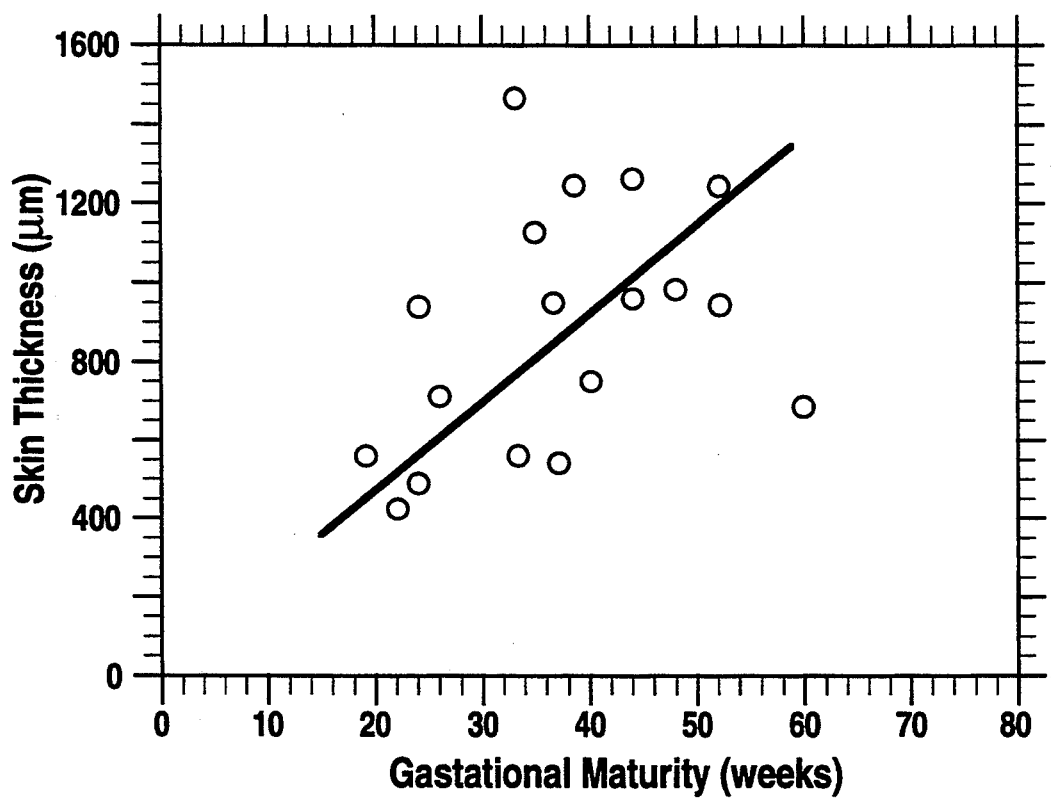
FIG. 31 is a graph of the distribution of measured skin thickness as a function of a gestational maturity.

The thickness of adult skin is reported in the literature to vary according to subject and site, with the mean values reported between 0.9 and 1.3 nun [Alexander, 1979]. The twenty neonatal post mortem skin samples obtained for in vitro optical property measurements had a mean thickness of 888 μm, and a standard deviation of 301 μm (Section 2). The thickness of these skin samples was found to have only a weak correlation with gestational age of the neonate, as seen in FIG. 31. This relationship is:

$$\text{Skin thickness (μm)} = 22.5 + 25 \text{ (maturity)} \quad (4\text{-}18)$$

where maturity is expressed in weeks.

The layer below the dermis is called the hypodermis, and is composed primarily of collagen fibers and fat cells [Millington 1983]. It is a deep extension of the dermis, and collagen fibers connect the two layers. The hypodermis also contains special nerve endings that service the skin, and a sub-dermal plexus of blood vessels.

Variability in the thickness of the skin can lead to variation in the reflectance spectra measured at the skin surface. This problem is of concern primarily at longer wavelengths and for less mature neonates, where the optical depth of the skin is small. The effect of skin thickness on the reflected light measured with the optical patch is analyzed in Appendix C.

The thickness of the skin is found in Appendix C to present a potential source of error in the reflectance spectra measurements at the skin surface. Variation in the skin thickness may alter the reflectance measurements in the 650–750 nm range by about 3%, which in turn will affect the interpretation of the skin maturity. Variation in the skin thickness will play a smaller role in readings in the 400–600 nm range where blood and bilirubin absorb. The existence of a hypodermis consisting of collagen fibers and fat beneath the dermis, and measurement of the reflectance with an optical patch rather than measurement of total reflectance, will both decrease the effect skin thickness has on the measured reflectance. Light that has penetrated deeply into the skin has a higher probability of being diffusely reflected outside the optical patch collection area than shallow penetrating light. Measurement of the reflectance with smaller diameter optical patches restricts the depth sensitivity of the probe and will reduce the error introduced because of skin sample thickness.

4.6 Variation In Cutaneous Bilirubin

Bilirubin "staining" of skin is the foremost sign of jaundice. Elevated levels of bilirubin in the serum are translated into extravascular cutaneous deposition of the bilirubin pigment in the dermis and epidermis [Turkel 1990, Kapoor 1973]. The relationship between vascular and cutaneous bilirubin, and the kinetics of transfer between the two compartments are not well understood. The ratio of serum bilirubin and cutaneous bilirubin appears to be affected by a multitude of factors including exchange transfusion, phototherapy, measurement site, diet, serum albumin concentration, pH, and gestational and chronological age [Rubaltelli 1971, Hegyi 1986, Hegyi 1983, Schumacher 1990, Engel 1982, Knudsen 1989]. The equilibrium between serum and cutaneous bilirubin values is perturbed when there are rapid changes in the bilirubin concentration in either the skin, such as during phototherapy, or in the serum, such as after exchange transfusion. As a result of these factors that disrupt the equilibrium between serum and cutaneous bilirubin and the variables that affect the kinetics of transfer of bilirubin into the skin, one expects the correlation between cutaneous and serum bilirubin readings to be less than perfect. Serum bilirubin, however, is currently accepted clinically as the standard method used to quantify the level of jaundice.

Figure 32:
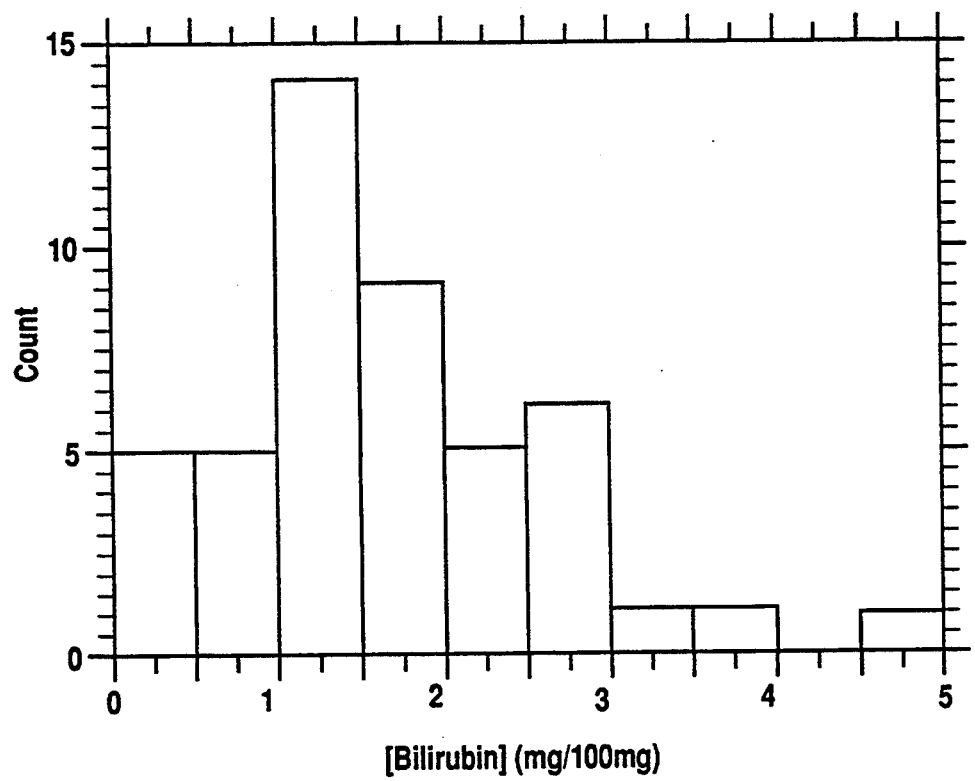
FIG. 32 is a graph of the demographic distribution of cutaneous bilirubin concentrations measured in the skin of 47 neonates.

FIG. 32 shows a sample distribution of the bilirubin concentration in the skin of 47 neonates measured in the neonatal intensive care unit. Some of these neonates were jaundiced. The method employed to determine the cutaneous bilirubin concentration is explained in Section 5.

4.7 Conclusions

The increase in scattering properties of neonatal skin with gestational maturity causes a decrease in the optical density at 837 nm, extrapolated from the measured optical density between 650 and 750 nm. This relationship is used to predict the maturity of in vivo skin samples. Variation in both the absorption and scattering coefficient in the dermis will change the sensitivity of optical density, $dOD/d\mu_a$, observed due to the addition of absorber, $\Delta\mu_a$, for example bilirubin or blood. This means that observed changes in the optical density can not be translated to changes in the bilirubin or blood content in the skin without analysis of the operative optical properties in the tissue.

The melanin spectra has been measured in vivo, by determining the $\Delta O.D$ for dorsal versus ventral forearm, and by measuring the $\Delta OD$ between variable pigmented neonates. The amount of melanin in the epidermis can be determined at 650 nm, where there is negligible absorption due to blood or bilirubin.

Blood is seen histologically to be present in the dermis in a collection of plexi that are interconnected. Monte Carlo simulations of light reflection from neonatal skin reveal that the depth of the blood beneath the surface does not affect the reflectance of 460-nm or 585-nm light. The reflection of 420-nm light, however, significantly increases with increasing depth of the blood vessels beneath the surface. Therefore, based on histological evidence and the Monte Carlo results, the blood and bilirubin can be modelled to be diffusely distributed throughout the dermis.

Monte Carlo simulations indicate that a decrease in the thickness of the skin lowers the measured reflectance spectrum. The effect that the skin thickness has on the measured reflectance is diminished by the fact that the hypodermis, the layer underlying the dermis, is composed primarily of collagen and fat cells and is expected to have a high reflectance value. Furthermore, light that has penetrated deeply into the skin has a higher probability of being diffusely reflected outside the optical patch collection area than shallow penetrating light. However, variation in skin thickness can still be a source of error in determinations of the skin maturity from the reflectance spectra. Appendix C treats this problem, and estimates the error.

Bilirubin in the blood stains the epidermis, and there is expected to be an equilibrium between serum concentrations and cutaneous bilirubin concentrations. The correlation between serum and cutaneous bilirubin is expected to be less than perfect and the equilibrium is affected by several factors, such as blood pH, albumin concentration, and phototherapy status of the neonate. The cutaneous bilirubin is considered to be diffuse throughout the dermis in the model of jaundiced neonatal skin.

Section 5

Determining Cutaneous Billrubin From Reflectance Measurements

5.1 Introduction

As discussed in Section 4, serum bilirubin levels are not expected to correlate perfectly with cutaneous bilirubin concentrations. The relationship between the two is influenced by blood pH, albumin concentration, phototherapy status, and other physiological parameters. Nevertheless, this invention measures cutaneous bilirubin in a manner that is independent of skin optics. To correctly determine the cutaneous bilirubin concentration, one has to interpret the reflectance with consideration of the variation in scattering properties of the tissue, and the non-linearity of the changes in bilirubin with addition of absorption.

In Subsection 5.2, a Monte Carlo model of skin was devised in which the cutaneous bilirubin concentration was varied in skin of three different gestational maturities. The reflectance predicted by the Monte Carlo calculations were analyzed by iterating to find the absorption coefficient in the skin, as explained in Section 3. This method of calculating the absorption coefficient which is then related to the cutaneous bilirubin concentration is compared to the traditional method in which the optical density is related to the cutaneous bilirubin concentration.

In Subsection 5.3 the method to determine absorption from a tissue with known scattering properties, are combined with the model of skin, and the considerations discussed in Section 4, to develop an algorithm to determine the cutaneous bilirubin concentration from optical patch reflectance measurements in accordance with the present invention. In Subsection 5.4, this algorithm is applied to measurements performed on neonates, and the algorithm is refined in Subsection 5.5, based on serum bilirubin values, since that is the only reference available for the degree of jaundice. In Subsection 5.6, the potential errors in our cutaneous bilirubin determinations are estimated.

5.2 Monte Carlo Model Of Cutaneous Billrubin

To test the fundamental ability to determine the concentration of an absorber in skin with different scattering properties, a Monte Carlo model was used to simulate variably scattering skin with specified concentrations of uniformly distributed bilirubin in the dermis. The Monte Carlo model predicts the reflectance from tissues in which the absorption and scattering coefficients are precisely known. This model was used to determine whether, and by what kind of analysis, we can predict the absorption in a tissue with known scattering properties.

In an in vivo population, a number of variables in the properties of the skin can vary between patients. For example, blood concentration, melanin concentration, and the scattering coefficient in the infant's skin may not be precisely known. Furthermore the concentration of the cutaneous bilirubin concentration is not precisely known, since serum concentrations are measured, and the relationship between serum and cutaneous concentrations are not fully understood as discussed in Subsection 4.5. With a Monte Carlo model of the skin, however, all the variables can be controlled while the bilirubin concentration is varied.

The Monte Carlo model is used to determine if the absorption coefficient in a tissue can be determined from the reflectance, once the scattering of the tissue is known. Once verified with the Monte Carlo model, the algorithms developed based on radiative transport theory can then be applied to in vivo measurements.

5.2.1 Monte Carlo Simulations

The Monte Carlo model simulated skin in which the scattering corresponded to 20, 30, and 40 weeks gestational maturity. The blood was simulated as occupying 5% of a 50-$\mu$m thick papillary plexus layer at 150 $\mu$m below the skin surface. This model was explained in Subsection 4.4. The bilirubin was simulated to be uniformly distributed throughout the skin. No melanin was included in the model. The values chosen for the cutaneous bilirubin concentrations approximate the range of concentrations reached in skin under normal and jaundiced conditions [Rubaltelli 1971]. The cutaneous bilirubin concentrations used in the Monte Carlo simulations, the corresponding absorption values at 460 nm, due to bilirubin, and the resulting reflectance values predicted by the Monte Carlo simulations at 460 nm are shown in Table 5.1.

TABLE 5.1

| Bilirubin | | Skin Maturity (weeks) | | |
|---|---|---|---|---|
| Concentration (mg/100 g) | $\mu_a$ at 460 nm (cm$^{-1}$) | 20 | 30 | 40 |
| | | Reflectance | | |
| 0 | 0 | 0.177 | 0.182 | 0.250 |
| 1.27 | 3.25 | 0.114 | 0.122 | 0.168 |
| 2.54 | 6.50 | 0.076 | 0.095 | 0.137 |
| 3.81 | 9.75 | 0.057 | 0.081 | 0.113 |
| 5.08 | 13.0 | 0.049 | 0.064 | 0.095 |

5.2.2 Analysis By Optical Density Method

Figure 33:
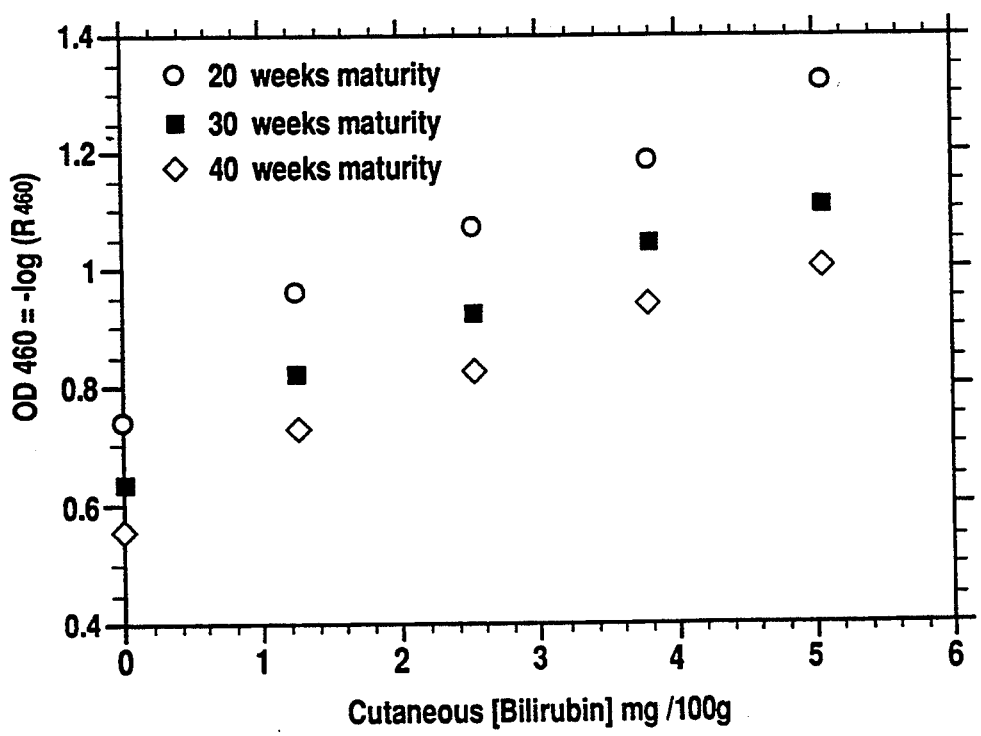
FIG. 33 is a graph of the optical density predicted by Monte Carlo simulations, in accordance with the present invention, as a function of cutaneous bilirubin concentrations for neonatal skin of three maturities.

The reflectance values predicted by the Monte Carlo simulations described above emphasize the importance of taking the scattering of the tissue and radiative transport theory into consideration for correct analysis of the reflectance spectra. FIG. 33 shows the optical density at 460 nm as a function of the cutaneous bilirubin concentration for the three skin maturities tested. The optical density is equal to $-\log_{10}(R)$, where R is the reflectance predicted by the Monte Carlo simulations. The optical densities are shown to increase with added bilirubin in a nonlinear manner. Moreover, the relationship between optical density and added bilirubin varies with the maturity of the skin. (How $(dOD/d\mu_a)\Delta\mu_a\,_{bili}$ varies with variable scattering is discussed in Section 4.2). Simple subtraction of a baseline optical density measured at another wavelength will not solve this problem since $\Delta OD/\Delta\mu_a$ is still variable with maturity. Furthermore, additional absorption due to another pigment, such as blood, will affect the change in optical density due to bilirubin absorption.

5.2.3 Analysis By Determining The Tissue Absorption Coefficient

Figure 34:
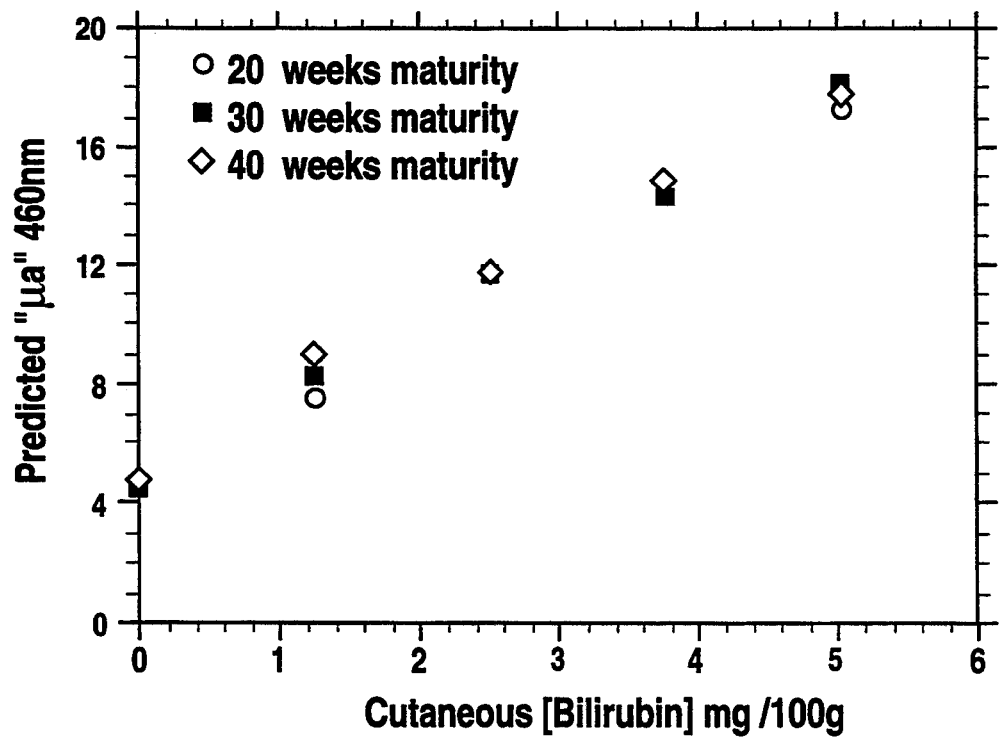
FIG. 34 is a graph of the predicted absorption at 460 nm as a function of bilirubin concentration for neonatal skin of three maturities.

Since direct analysis of the reflectance, or $-\log(R)$, can not be applied to accurately determine the absorption in a tissue, radiative transport theory can be used as explained in Section 3. The equations relating absorption within the tissue and scattering are iterated with the known scattering fixed and the absorption adjusted until a solution for the measured reflectance is reached. This method was introduced and explained in Subsection 3.6. FIG. 34 shows the total absorption predicted in this manner at 460 nm for the Monte Carlo reflectance results as the bilirubin concentration is varied in the skin. If FIG. 34 is compared to FIG. 33, the absorption can be seen to be calculated much more reliably if knowledge of the scattering coefficients of the tissue is utilized, and the change in optical density with added absorber is not assumed to be constant.

5.2.4 Conclusions

The Monte Carlo model illustrates what is required to correctly determine the average bilirubin concentration in the tissue, and why simpler analysis of the optical density changes in tissue due to added absorption do not give predictable results. The variation in such analysis is due to (i) variation in the scattering properties of the measured tissue, and (ii) variation in $(dOD/d\mu_a)\Delta\mu_a\,_{bili}$ when the quantity of other absorbers (e.g. blood) are variable. Furthermore, the relationship between changes in optical density, and absorption in the tissue is not linear. Therefore, linear regression analyses to correlate the bilirubin concentration in newborn infants to cutaneous optical density changes will not give good correlations in populations in which the skin scattering properties, or skin blood concentration vary.

Figure 35:
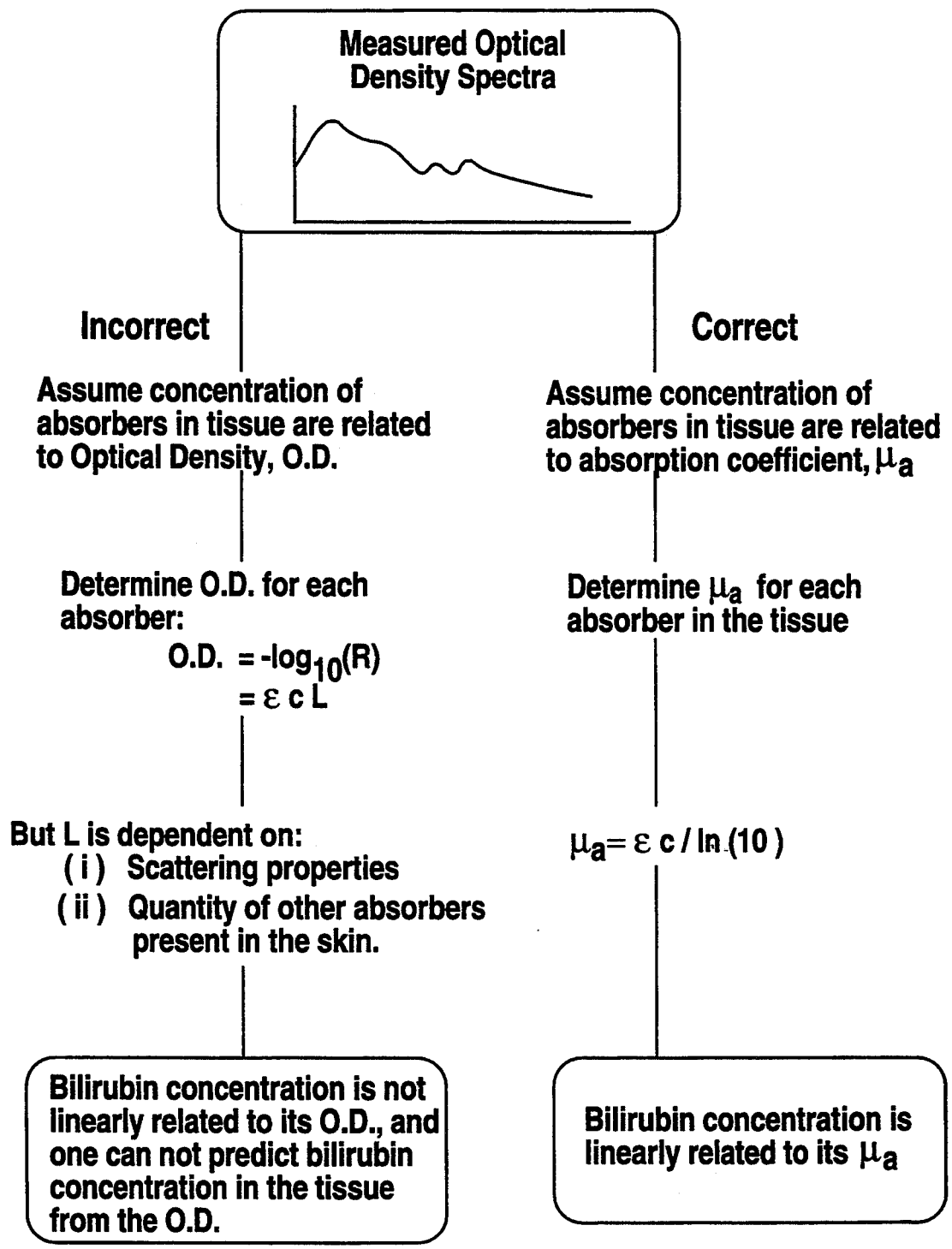
FIG. 35 is a flow chart comparing two methods of determining cutaneous bilirubin concentration.

Finally, transcutaneous reflectance spectra are often measured with an optical device, such as an optical patch, in which not all the reflected light is collected [Kopola 1990, Hegyi 1983, Hannemann 1978, Krauss 1976]. The collection efficiency, f*, of the optical patch is partially dependent on the scattering of the tissue (see Section 3). Variation in the f* will accentuate the differences in measured reflectance from skin of different scattering properties. FIG. 35 summarizes the correct considerations required to determine the concentration of an absorber in a tissue from measurement of the reflectance spectra. The fundamental errors in interpretation of the measured spectra by means of direct analyses of the optical density measurements are also presented again in this figure.

5.3 Algorithm To Determine The Cutaneous Bilirubin

The Monte Carlo model in Subsection 5.2 illustrates the best method to determine the total absorption coefficient of a tissue from the reflectance measurements. In Section 3, a method was developed to determine the absorption coefficient within a tissue of known scattering properties. In Section 2, the scattering coefficient and basal absorption coefficient of neonatal skin were determined. In Section 4, the various sources of variability and their effects on measured reflectance were discussed individually. These considerations are combined in this section to derive an algorithm that can be applied on neonatal skin to determine the cutaneous bilirubin concentration. This algorithm will be applied on the neonates measured in vivo, and the results correlated to serum levels measured.

The basic purpose of the algorithm of the present invention is to deduce the absorption due to bilirubin from reflected blue light. However, other tissue components also absorb in the blue light spectrum, including skin, melanin and blood. According to the present invention, reflectance at other wavelenghts is used to specify the maturity-dependent optical properties of skin, the amount of melanin, and the amount of blood in the skin. Once the optical absorption of skin, melanin or blood is known at one wavelength, its contribution to blue light reflectance can be predicted and subtracted from the total absorption of blue light, to yield the absorption due to bilirubin alone. From this quantity, an average concentration of bilirubin in the skin can be determined.

The wavelengths of reflectance measurements that are specified for use in this disclosure have been chosen for the reasons articulated in the following paragraphs. However, it will be understood that in general the entire reflectance spectrum from 350-800 nm may be used by the present invention.

To specify the gestational maturity of the skin under test, reflectance measurements are taken in the red to infrared light spectrum, for example, in the range of 650-800 nm. These measurements are then extrapolated to 837 nm to specify the reflectance at 837 nm, which is related to the gestational maturity of the neonatal skin. Once the maturity of the skin is established, the maturity-dependent optical properties are specified (using equations 2-5 to 2-9). These equations yield the absorption, $\mu_a(\lambda)$, and scattering, $\mu_s(\lambda)$, as a function of wavelength, $\lambda$ for use by the other portions of the algorithm.

To detect melanin content in the skin, the reflectance, M, of red light is used, for example, 650 nm. Red light is chosen because the absorption of blood is substantially negligible. It should be noted that any wavelength between 600–800 nm could be used to detect melanin content, but 650 nm provides for a strong absorption by melanin and avoids strong absorption by blood. The values for absorption and scattering are then calculated, once again in accordance with equations 2-5 to 2-9. The predictions of true reflectance, R650 and the probe collection efficiency, f*650, are provided by equation 3.3 in section 3.3.3. The product, (f*650) (R650), or f*R650, yields the expected measurement, M650, in the absence of the melanin. The optical density due to melanin, ODmelanin650 can then be specified, and the melanin absorbance in the yellow-orange spectrum and in the blue range of the spectrum can be specified. This is then subtracted from optical densities measured in the blue spectrum and in the yellow-orange spectrum to yield optical densities essentially independent of melanin, which allows the remainder of the algorithm to ignore the effects of melanin and to consider only the effects of skin, blood and bilirubin.

To specify the blood (hemoglobin) content of the skin, reflectance in the yellow-orange spectrum is detected, for example, 585 nm. Bilirubin does not absorb at 585 nm. The choice of 585 nm uses the isobesic wavelength of hemoglobin absorption, such that the absorption by blood is the same regardless of the oxygen saturation of the blood. There are several other isobesic wavelengths for hemoglobin that could also be used. To convert optical density detected in the yellow-orange spectrum into an absorption coefficient, an iterative cycle is used to deduce the absorption in the yellow-orange region of the spectrum independent of melanin, and independent of the effects of scattering and probe geometry. The result is absorption due to skin and blood. The absorption due to skin, calculated with gestational maturity, is then subtracted from the total absorption to yield the absorption in the yellow-orange region of the spectrum which is due to blood alone. This quantity specifies the amount of blood in the skin.

To determine a raw value for absorption due to bilirubin, reflectance in the blue light spectrum is detected, for example, 460 nm. The measured reflectance is converted into optical density in the blue spectrum, which in turn is converted into an absorption coefficient, using the same iterative procedure as discussed above with respect to the yellow-orange spectrum. The result is an absorption coefficient in the blue spectrum due to bilirubin, blood and skin, independent of bilirubin, and independent of the scattering and probe geometry. Absorption due to bilirum alone is then calculated by subtracting absorption due to blood and absorption due to skin from the total absorption calculated in the blue spectrum. Once the absorption due to bilirubin is calculated, the average bilirubin concentration in the skin can be calculated.

Finally, reflectance measured in the purple-blue spectrum, for example, 420 nm, is used to detect the depth of blood in order to calculate a correction factor, $\chi$, which accounts for spectral distortion resulting from different penetration depths of the measuring wavelengths.

5.3.1 Determining The Maturity Of The Infants Skin

The first step in the algorithm is to determine the maturity of the neonatal skin. The measured optical density between 650 and 800 nm is extrapolated to 837 nm, as discussed in Subsection 4.2. The extrapolated reflection at 837 nm, f*R837, was found to be related to maturity (in weeks) by the following relationship (See FIG. 20):

$$\text{maturity} = 10^{([2.72 + (f^*R837)]/2.43)} \qquad (5\text{-}1)$$

This relationship was determined by a fit of the f*R837 values measured as a function of known gestational maturity. The form of this relationship was discussed in Subsection 4.2.1 (See Equation 4-3).

5.3.2 Subtraction Of Melanin

As discussed in Section 3 and 4, the melanin is only present in the epithelium, and so has to be treated separately than absorbers present diffusely within the skin. As presented in Section 3, the impact of melanin on the collection efficiency of the optical patch, f*, can be neglected relative to impact of other absorbers within the dermis. Therefore, the melanin spectra (shown in FIG. 25) can be subtracted from the measured reflectance spectra, $M(\lambda)$, before correction of the spectra for f* is made.

The melanin content of the epidermis is determined at 650 nm, where the effect of blood and bilirubin on reflectance is relatively small. At this wavelength, the expected reflectance from the dermis can be calculated since the scattering and absorption at 650 nm is known. The optical density at 650 nm due to melanin content is then calculate as:

$$OD_{melanin}(650) = -\log[M(650)] - (-\log(\text{predicted } M(650)]) \qquad (5\text{-}2)$$

where $$\text{predicted } M(650) = -\log(f^*R(650)) \qquad (5\text{-}3)$$

and where f* and R at 650 are those predicted for the dermis and are calculated from the optical properties (see Equations 3-27 and 3-35).

The effect of melanin on the optical density spectra at wavelengths of interest can be calculated by multiplying the $OD_{melanin}(650)$ value by a constant. The constant corresponds to the optical density of melanin at the wavelength of interest relative to that at 650 nm. Therefore, the component of the measured optical density at 460 nm due to melanin is:

$$OD_{melanin}(460) = k1 \, OD_{melanin}(650) \qquad (5\text{-}4)$$

and that at 585 nm is defined as:

$$OD_{melanin}(585) = k2 \, OD_{melanin}(650) \qquad (5\text{-}5)$$

The values of k1 and k2 can be determined from FIG. 25, and are 2.2 and 1.4, respectively.

The measured optical density at 460 nm, OD(460), that has the effect of melanin removed is therefore:

$$OD(460) = -\log[M(460)] - OD_{melanin}(460) \qquad (5\text{-}6)$$

and that at 585 nm, OD(585), is:

$$OD(585) = -\log[M(585)] - OD_{melanin}(585) \qquad (5\text{-}7)$$

Figure 36:
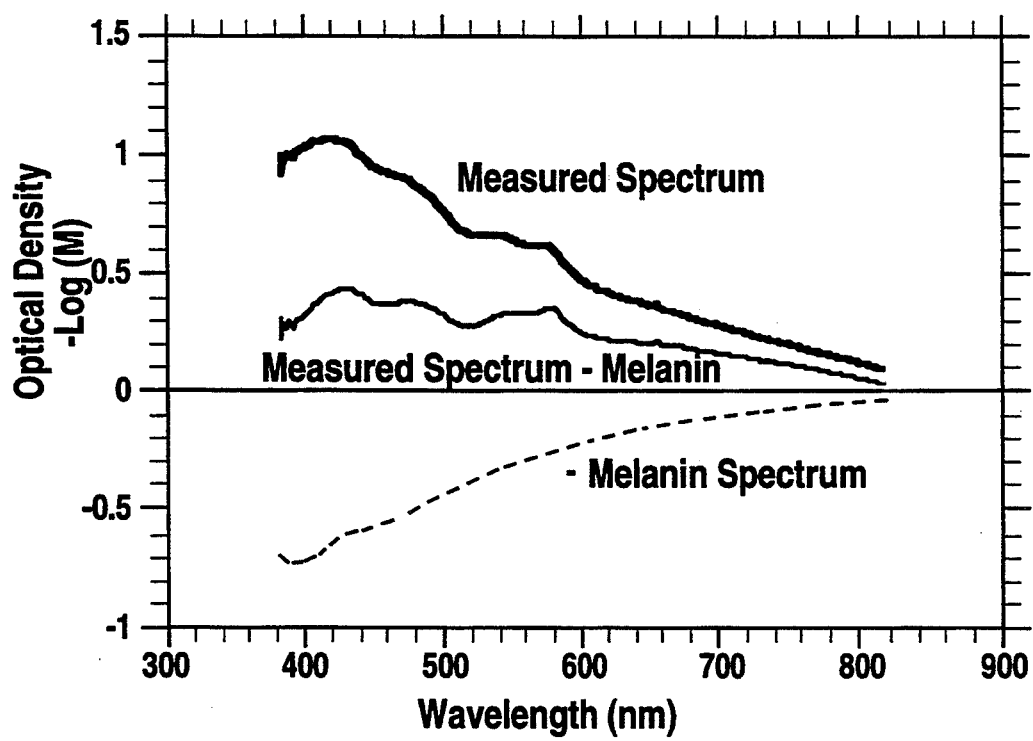
FIG. 36 is a graph of the optical density spectrum of melanin subtracted from the measured optical density spectrum.

FIG. 36 illustrates how a sample optical density spectra measured on a neonate is divided into the melanin component, which is subtracted away, and the remaining measured optical density due to the skin, blood, and bilirubin.

5.3.3 Determining Absorption Of Blood And Bilirubin

Data presented in Subsection 4.4 showed that the penetration of 460 nm and 585 nm light into neonatal skin was sufficiently deep such that the reflectance from tissue at those two wavelengths does not vary significantly with possible variations in the location of the blood papillary plexus, and bilirubin deposition within the skin. Therefore, the chromophores at these two wavelengths can be treated as diffuse absorbers distributed within the tissue.

The optical density after subtraction of the $OD_{melanin}$, at any particular wavelength of interest, is dependent on the scattering of the tissue, and the absorption due to the tissue, blood, and bilirubin at that wavelength. The scattering coefficient, $\mu_s'$, and the total absorption coefficient, $\mu_a$, within the tissue determine the reflectance, R, and the collection efficiency of the patch, f*. As discussed in Subsection 3.6, the procedure to find R and f* from the optical coefficients can be iterated, each time adjusting the absorption coefficient until the predicted and measured O.D. match. A small reflectance adjustment factor (which is presented and explained in Appendix C) is introduced in the iteration procedure to partially correct for skin thickness error. In this manner, the total absorption coefficient in the tissue is specified.

The above iterative procedure to determine the absorption coefficient is implemented at 460 and 585 nm, to obtain $\mu_a 460$ and $\mu_a 585$, respectively. At 460 nm, there is significant absorption from bilirubin blood and skin, while at 585 nm, the absorption due to bilirubin is negligible, and blood and skin are the only absorbers. As described in Section 2, the absorption due to skin is known, and is not expected to vary significantly from person to person, even for neonates of different gestational ages.

The absorption coefficients that were determined in the skin at 460 and 585 nm attributed to bilirubin and blood, are equivalent to diffuse absorption and are insensitive to possible variations in the location of the bilirubin and blood in the skin. This phenomena was discussed in Subsection 4.4

To calculate the absorption due to blood, the absorption of the skin is subtracted from the total absorption determined at 585 nm:

$$\mu_a\, blood(585) = \mu_a(585) - \mu_a\, skin(585) \qquad (5\text{-}8)$$

The absorption of blood at 460 nm is equal to a fraction of the absorption at 585 nm, as determined from the blood absorption spectra. This relationship is expressed as:

$$\mu_a\, blood(460) = \chi k3\, \mu_a\, blood(585) \qquad (5\text{-}9)$$

where k3 is the factor that relates the absorption coefficient of blood at 460 nm to the at 585 nm, and is equal to 1.40 [Jacques 1990a, Nahas 1951].

It has been determined that measured optical density decreases as the depth of blood layer increases, and that the rate at which the optical density decreases with increasing blood depth varies for different frequencies. Thus, in equations 5-9, correction factor, $\chi$, is used to account for this spectral distortion. The ratio of the optical density detected at 420 nm, OD420, to the optical density at 585 nm, OD585, is related to the depth of the blood layer beneath the skin. In the present application, it has been determined that $\chi$ can be set to 1.0.

The bilirubin absorption at 460 nm can then be calculated, by subtraction of the blood and skin absorption at 460 nm.

$$\mu_a\, bilirubin = \mu_a(460) - \mu_a\, blood(460) - \mu_a\, skin \qquad (5\text{-}10)$$

The cutaneous bilirubin concentration, [Bilirubin], expressed in mg/100 g tissue, is related to the bilirubin absorption, $\mu_s$ bilirubin expressed in cm$_{-1}$, by the following expression:

$$[\text{Bilirubin}]\ \text{in mg/100 g} = 2.56\, \mu_a\, \text{bilirubin} \qquad (5\text{-}11)$$

Figure 37A:
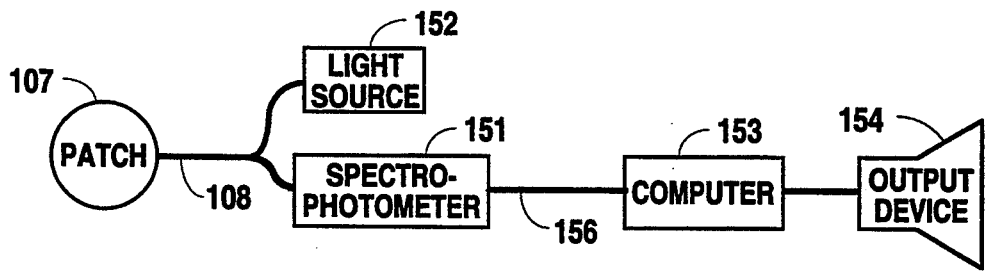
FIG. 37a is a block diagram of a hardware embodiment of the present invention.

FIG. 37A is a block diagram of a hardware embodiment of the present invention including optical patch 107 connected to spectrophotometer 151 and light source 152 through fiber optic bundle 10B. Spectrophotometer 151 is connected to computer 153, including display or other output device 154. The structure of optical patch 107 is discussed above with reference to FIG. 8A. Spectrophotometer 151 can be, for example, a type 8452A spectrophotometer available from Hewlett-Packard. Light source 151 can be, for example, a tungsten-halogen lamp that emits a relatively constant light output for the wavelengths of interest (300-800 nm). Computer 153 can be, for example, a laptop computer available from Toshiba, Zenith or Datavue. Computer 153 communicates with spectrophotometer 151 via IEEE-488 bus 156, or the equivalent.

Figure 37B:
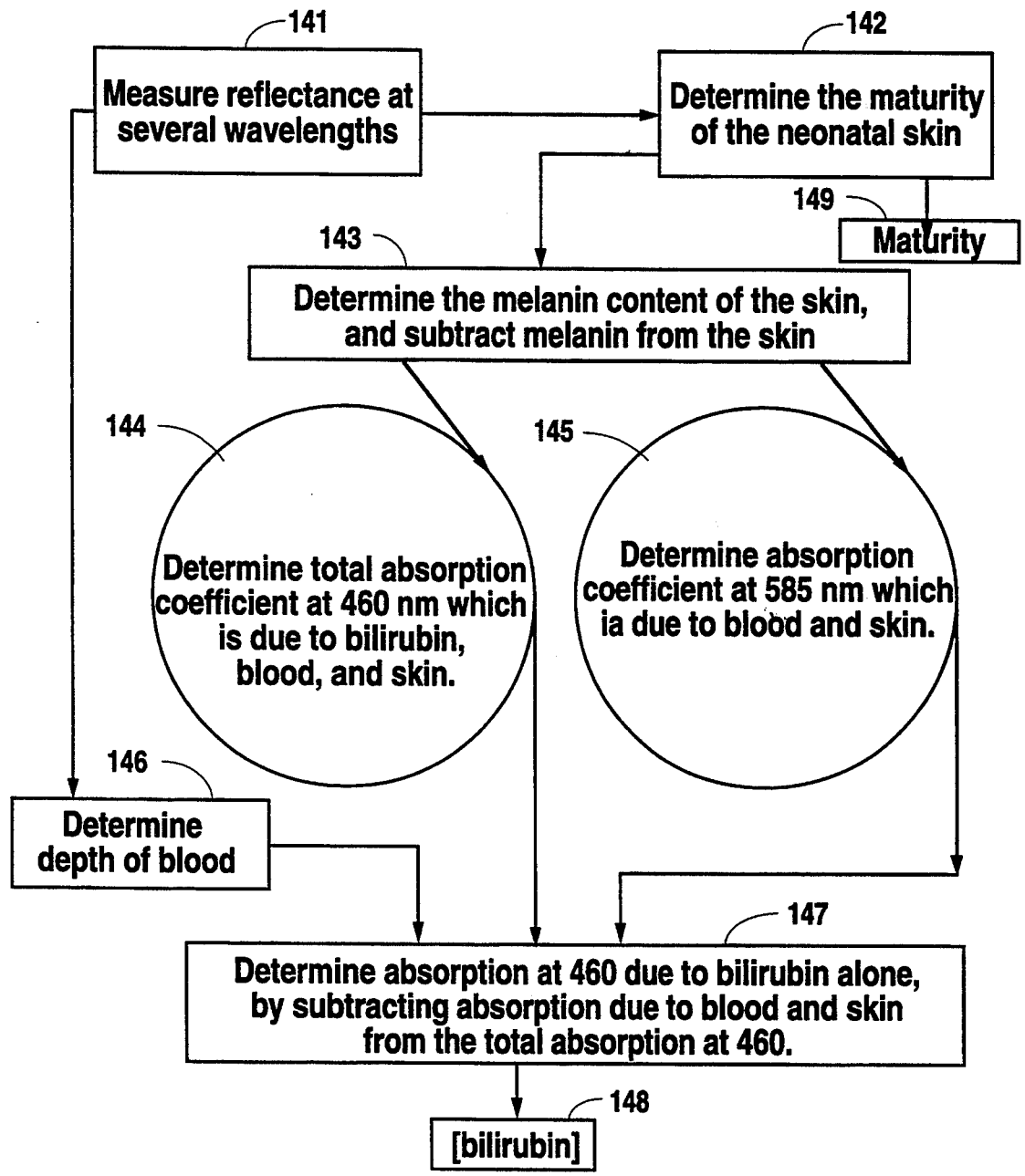
FIG. 37b is a flow chart of the method of the present invention to determine cutaneous bilirubin concentrations from measured reflectance spectra.

FIG. 37B, is a block flow chart that summarizes the algorithm of the present invention that determines the concentration of cutaneous bilirubin. This algorithm can be applied with a different optical delivery and collection device, if the relationship between optical coefficients and f* for optical patch 107 is substituted by that appropriate for the device used.

Referring to FIG. 37B, in block 141, reflectance from skin under test is measured at various wavelengths. Control then passes to block 142 where maturity of the skin is determined. As a by-product, gestational maturity is determined in block 149.

From block 142, control passes to block 143 where the melanin content of the skin is determined, and subtracted from the absorption due to skin calculated in block 142. Control then passes to iterative loops 144 and 145. In loop 144, the total absorption coefficient in the blue spectrum is calculated, and in loop 145, the total absorption coefficient in the yellow-orange spectrum is calculated. Block 146 calculates the depth of blood in the skin. Then, the products from blocks 144, 145, and 146 are applied to block 147 where the absorption due to bilirubin alone is calculated by substracting the absorption due to blood and skin from the total absorption of blue light, with blood depth taken into consideration. Control then passes to block 148 where the cutaneous bilirubin concentration is calculated.

Figure 37C:
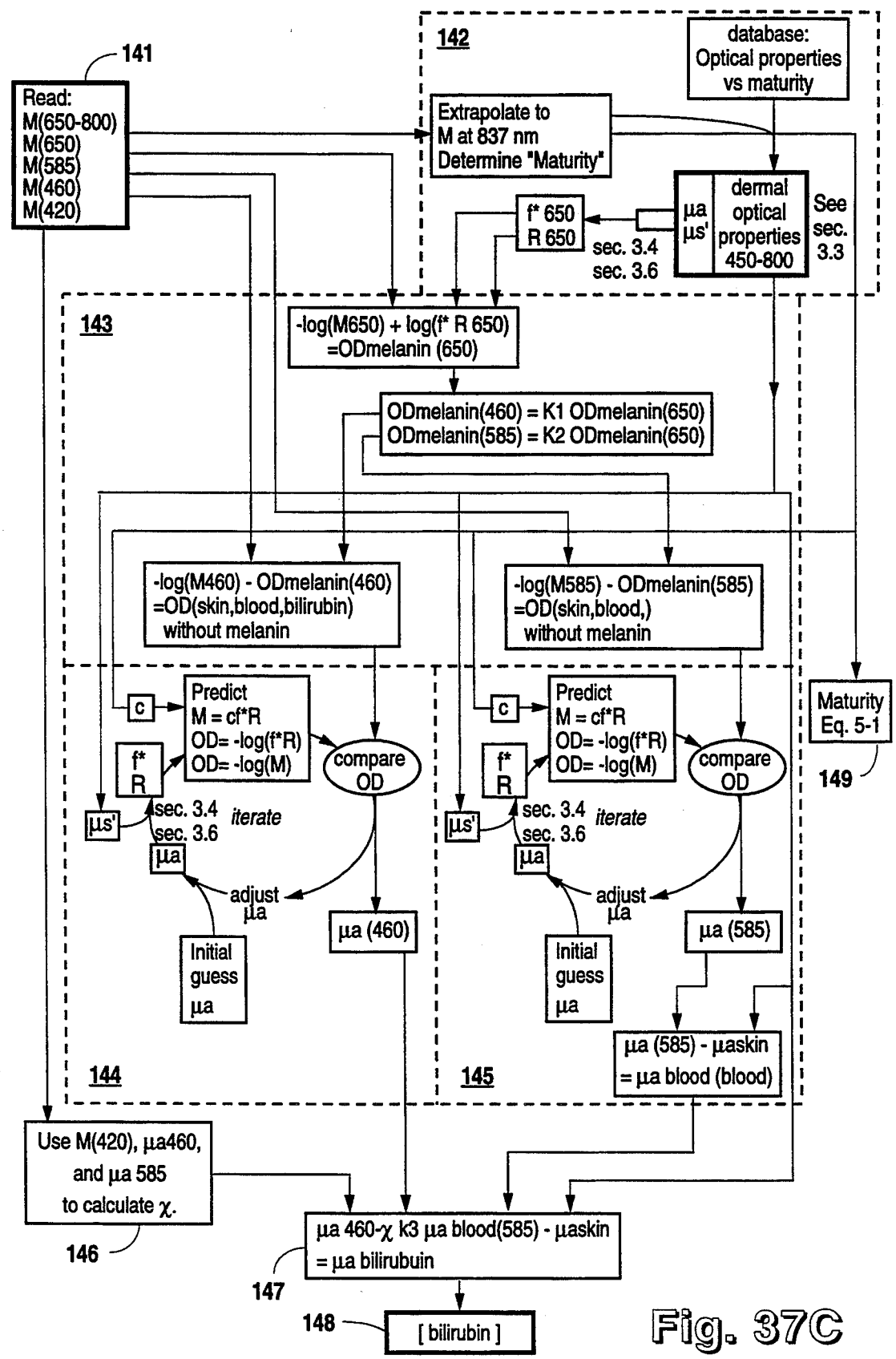
FIG. 37c is a more detailed flowchart of the method of the present invention depicted in FIG. 37b.

The flow chart of FIG. 37C presents a more detailed version of the flow chart of FIG. 37A. The equations used by the algorithm in FIG. 37C are shown in Table 5.2. Appendix E includes a source code program that embodies the flow chart of FIG. 37C. In practice, a program written in accordance with a flow chart of FIG. 37C, for example, like that shown in Appendix E, is loaded into the program memory of computer 153 in order to operate the hardware shown in FIG. 37A to perform the transcutaneous bilirubin measurement method of the present invention.

5.5 Algorithm Refinement

To evaluate and refine the algorithm which measures the cutaneous bilirubin concentration, the following procedure was implemented. As expressed earlier, there

татBLE 5.2

| | | |
|---|---|---|
| acquire data | measure $f^*R$ = (=M) at 420,460,585,650–800 nm | Sec. 5.3 |
| | $OD = -\log(f^*R)$ | Eq. 3-7, 4-1a |
| determine maturity | extrapolate $OD_{650-800}$ to 847 nm → $OD_{837}$ | Sec. 4.2 |
| | $f^*R_{837} = 10\triangleright(-M_{837})$ | Eq. 4-16 |
| | maturity = $10\triangleright((2.72 + f^*R_{837}/2.43)$ | Eq. 5-1 |
| remove melanin | $\mu_a 650 = 0.55$ $\mu_s'650 = -6 + 0.68(\text{maturity})$ | Eq. 2-5, 2-6, 2-7, 2-9 |
| | $f_{650} = f(\mu_a 650, \mu_s'650)$ | Eq. 3-27 |
| | $R_{650} = f(\mu_a 650, \mu_s'650)$ | Eq. 3-35 |
| | $f^*_{650} = (f_{650})/0.31$ | Eq. 3-3, Sec. 3.3.3 |
| | predicted_$M_{650} = -\log(f^*R_{650})$ | Eq. 5-3 |
| | $OD_{mel650} = -\log(M_{650}) - (-\log(\text{predicted}\_M_{650})$ | Eq. 5-2 |
| | $OD_{mel460} = k1\ OD_{mel650}, k1 = 2.2$ | Eq. 5-4 |
| | $OD_{22mel585} = k2\ OD_{mel650}, k2 = 1.4$ | Eq. 5-5 |
| | $OD_{460} = -\log(M_{460}) - OD_{mel460}$ | Eq. 5-6 |
| | $OD_{585} = -\log(M_{585}) - OD_{mel585}$ | Eq. 5-7 |
| slight adjustment factor for thickness | $C_{460} = 1 - 0.26\exp(-0.088\ \text{maturity})$ | Ex. C-4 |
| | $C_{585} = 1 - 0.27\exp(-0.057\ \text{maturity})$ | Eq. C-5 |
| convert OD to $\mu_s$ | $\mu_s' skin460 = = -15.9 + 1.5\ (\text{maturity})$ | Eq. 5-19 |
| | $\mu_s' skin585 = = -12.0 + 1.1\ (\text{maturity})$ | Eq. 5-20 |
| | initial guess for $\mu_a 460$ and $\mu_a 585$ is 1 cm$^{-1}$ | |
| | Send $OD_{460}$ and $OD_{585}$ through iterative cycle to yield: | FIG. 47 |
| | $\mu_a 460$, and $\mu_a 585$ | |
| linear analysis of absorption coefficients | $\mu_a\ skin460 = 1.71\ (\text{cm}^{-1}), \mu_a\ skin585 = 0.81\ (\text{cm}^{-1})$ | Eq. 5-18 |
| | $\mu_{ablood585} = \mu_a\ 585 - \mu_a\ skin585$ | Eq. 5-8 |
| | $\mu_a\ blood460 = \%k3\mu_a\ glook585, k3 = 1.40, \% \approx 1.0$ | Eq. 5-9 |
| | $\mu_a\ bilirubin = \mu_a\ 460 - \mu_a\ blood460 - \mu_a\ skin460$ | Eq. 5-10 |
| | $[\text{bilirubin}]_{avg}$ in mg/100 g tissue = $(\mu_a\ bilirubin)(2.56)$ | Eq. 5-11 |

5.4 Cutaneous Bilirubin Prediction In Clinical Measurements

As discussed in Subsection 4.6, the mechanisms of transfer of serum bilirubin to the skin are not fully understood. Cutaneous bilirubine concentrations increase with serum concentrations, but the two concentrations are not perfectly correlated since certain factors such as acidity, and phototherapy status are known to disrupt the relationship. The algorithm developed above for the determination of cutaneous bilirubin concentration is correlated to serum bilirubin levels here since there is not a better measure of the cutaneous bilirubin concentrations available.

The algorithm presented in Subsection 5.3 was applied to transcutaneous reflectance measurements performed with the optical patch connected to a Hewlett-Packard diode array spectrophotometer (model 8452-A). Serum bilirubin readings were available for 47 of the newborn infants measured. The neonates measured varied from 24 to 42 weeks gestational age, and comprised of 18 white, 6 hispanic, 23 black infants. Ten of the neonates measured were undergoing phototherapy at the time of measurement.

The forehead reflectance measurements were analyzed, since the forehead of those neonates undergoing phototherapy, was covered with an eye patch, which avoided photobleaching of the skin site measured. Also, skin in the cephalic regions of the body is documented to stain with bilirubin earlier than caudal regions, and therefore cutaneous levels there are expected to correlate more closely to serum bilirubin concentrations [Knudsen 1989].

Based on the results of the clinical measurements, some parameters in the algorithm of FIG. 37B were refined, as discussed in Subsection 5.5, where the clinical results are presented.

is not a reliable independent measure of the cutaneous bilirubin concentration. The serum concentrations are all we have as an indication of the degree of jaundice. For each neonate measured, we would expect the absorbance of cutaneous bilirubin, $\mu_{a\ bili}$, predicted by our algorithm to be proportional to the serum concentration, [Bili]serum, of the neonate. We chose to refine the algorithm in order to ensure that the ratio of $\mu_{a\ bili}$ to [Bili]serum is independent of the melanin and blood content of the skin. This assumes that variations in the rate of transfer of bilirubin from blood to the skin are due to physiological considerations of the infant, such as blood pH, and not dependent on the degree of melanin concentration, Melanin650, and blood content, measured as $\mu_{a\ blood}(585)$, in the skin.

Figure 38A:
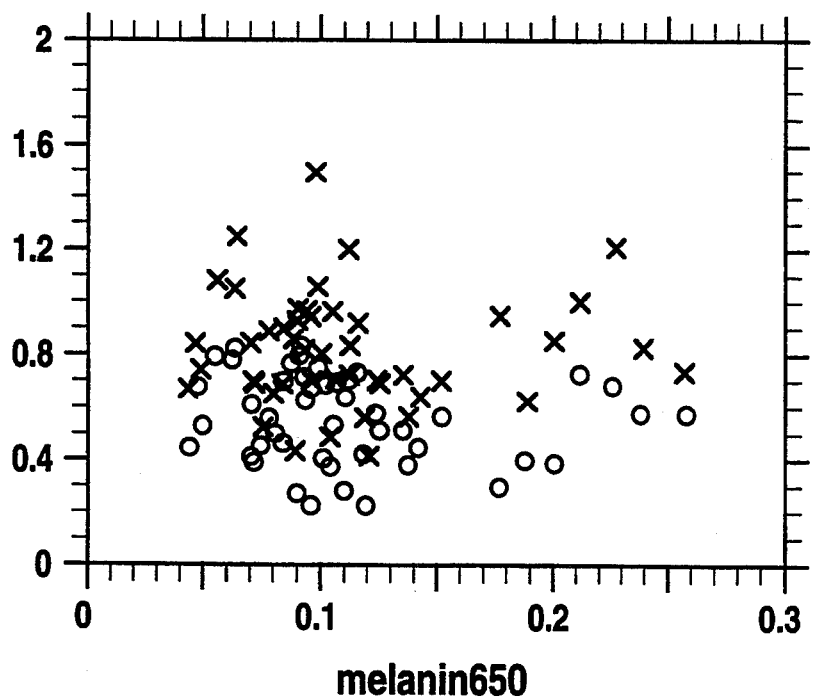
FIGS. 38A, 38B and 39 are graphs illustrating the function of the present invention.

The dependence of $\mu_a$bili/[Bili]$_{serum}$ on blood and melanin content was plotted as shown in FIGS. 38A and B. The $\mu_a$bili was calculated by the algorithm as presented in FIG. 37 and Table 5.2. A score was used to evaluate the dependence of $\mu_a$bili[Bili]$_{serum}$ on the independent variable, Melanin650, or $\mu_{a\ blood}(585)$. This score is explained in the next paragraph.

5.5.1 Calculations Of The Score

Figure 39:
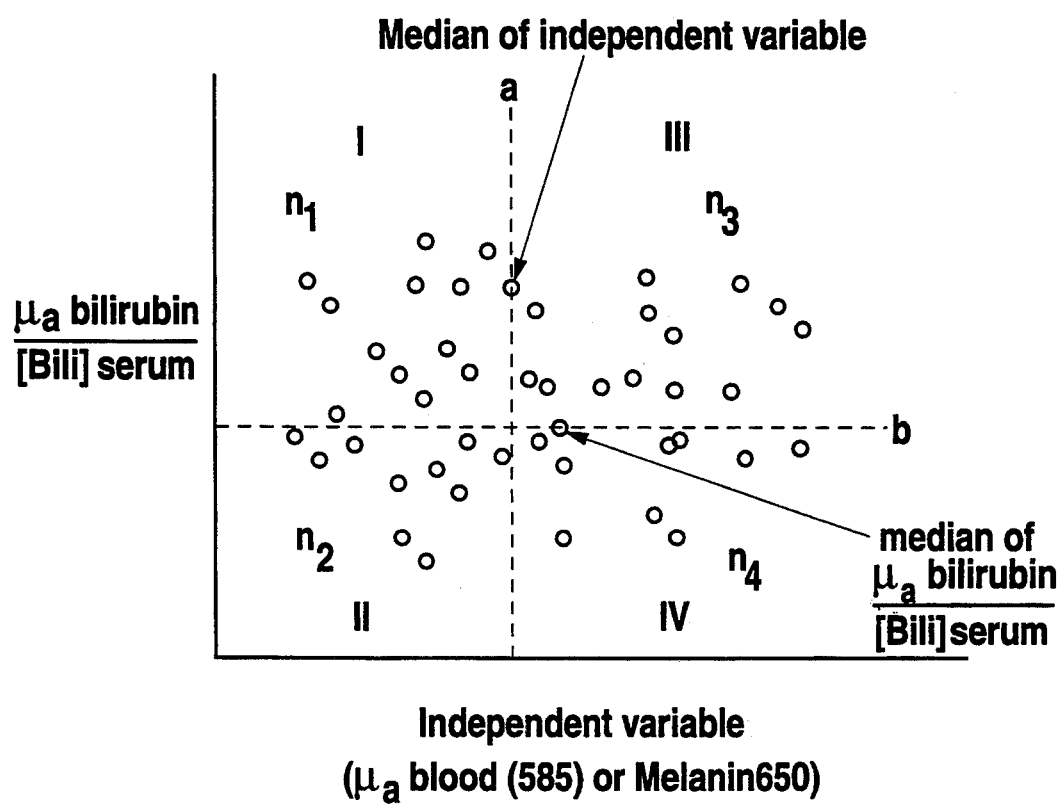

There is a spread in the values of the fraction, $\mu_a$bili/[Bili]$_{serum}$, and in the value of the independent variable, Melanin650, or $\mu_{a\ blood}(585)$, when they are plot. Four quadrants, I, II, III, and IV, are assigned on the plot, and the lines are set according to the median values of $\mu_a$bili/[Bili]$_{serum}$ and of the independent variable, as shown in FIG. 39. The number of points in each quadrant, I, II, III, or IV, are then assigned as $n_1$, $n_2$, $n_3$ or $n_4$, respectively. The score is then calculated as:

$$\text{Score}_{variable} = \frac{1}{2}\left|\frac{n_1}{n_1 + n_2} - \frac{n_3}{n_3 + n_4}\right| \tag{5-12}$$

The score for each variable is chosen such that a strong dependence (with a positive or negative slope) of the fraction, $\mu_a$bili/[Bili]$_{serum}$, on the independent variable will lead to a score approaching one half, while complete independence of the two variables will result in a score approaching zero. A score, Score$_{blood}$, was calculated for the dependence of $\mu_a$bili/[Bili]$_{serum}$ on blood absorption, $\mu_a$ $_{blood}$(585), and an independent score, Score$_{melanin}$, was calculated for the dependence of $\mu_a$bili/[Bili]$_{serum}$ on melanin content, Melanin650. The total Score is equal to the sum of Score$_{blood}$ and Score$_{melanin}$, as shown below, and may vary between zero and one.

$$Score = Score_{blood} + Score_{melanin} \quad (5\text{-}13)$$

5.5.2 Iteration To Optimize Equations Of Optical Coefficients

The algorithm was originally tested with the initial equations used for the absorption of skin as a function of wavelength (Equation 2-8), and the scattering at 460, 585, and 650 nm as a function of maturity (from Equation 2-5 through 2-7). These equations are:

$$\mu_a\text{skin} = a \exp(-b\lambda) = 5 \exp(-0.0035\lambda) \text{ (cm}^{-1}) \quad (5\text{-}14)$$
$$\mu_s'460 = \text{yint}_{460} + \text{slope}_{460}(\text{maturity}) \quad (5\text{-}15)$$
$$= -15.7 + 1.6 \text{ (maturity) (cm}^{-1})$$
$$\mu_s'585 = \text{yint}_{585} + \text{slope}_{585}(\text{maturity}) \quad (5\text{-}16)$$
$$= -16.7 + 1.22 \text{ (maturity) (cm}^{-1})$$
$$\mu_s'650 = \text{yint}_{650} + \text{slope}_{650}(\text{maturity}) \quad (5\text{-}17)$$
$$= -15.6 + 1.0 \text{ (maturity) (cm}^{-1})$$

Figure 40:
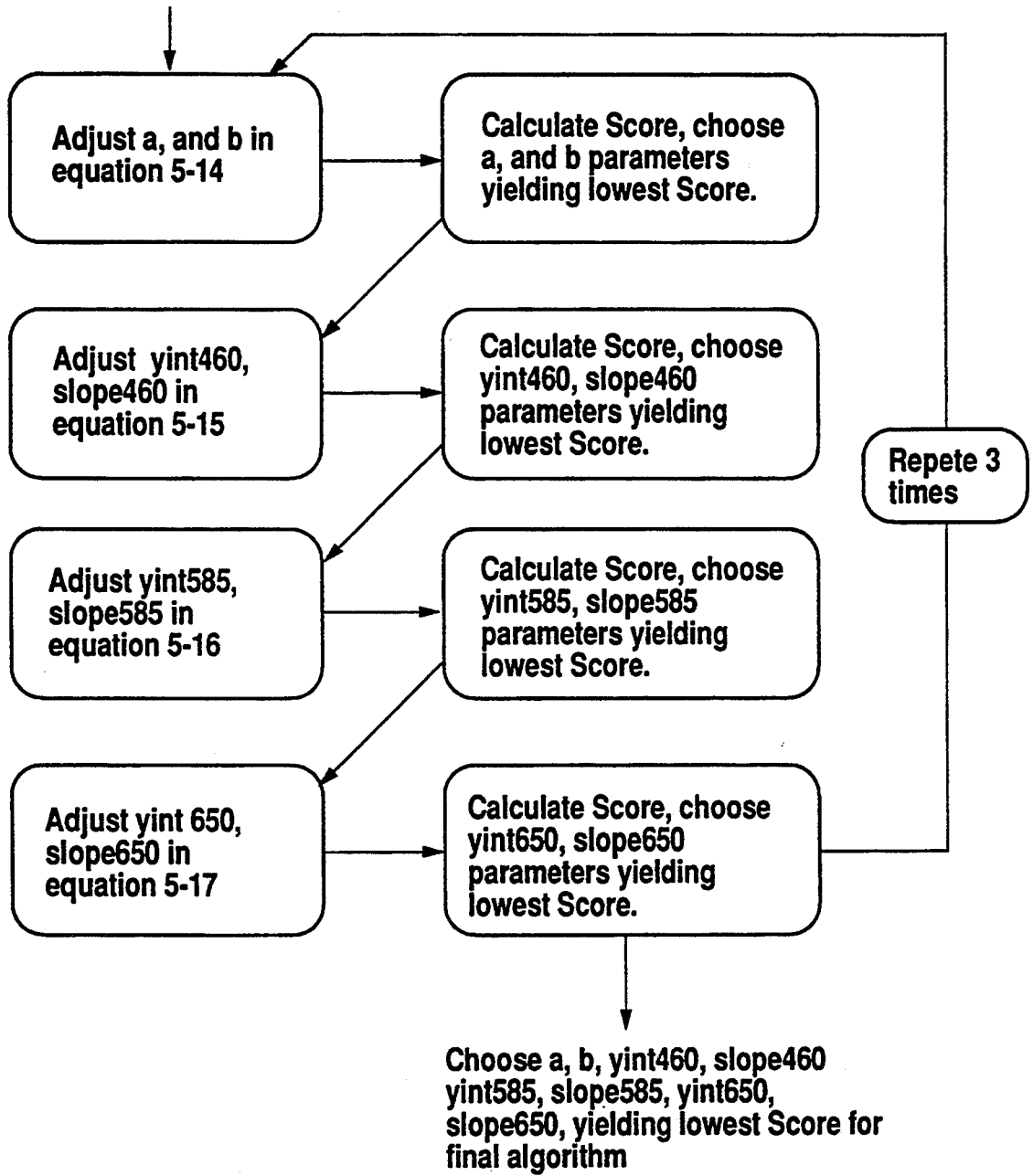
FIG. 40 is a flow chart of a method, in accordance with the present invention, to refine the method illustrated in FIG. 37 to determine cutaneous bilirubin concentrations.

For each of the neonates measured, the fraction of $\mu_a$bili/[Bili]$_{serum}$, was calculated and used to determine the total Score for the algorithm. To find the minimum Score, the parameters in the Equations 5-14 through 5-17 were varied in a range that resulted in changes in the optical properties of less than about 15%. Parameters which yielded non-sensible results (for example $\mu_a$bilirubin, or $\mu_a$blood values less than zero) were disregarded. The procedure followed to adjust these parameters is illustrated in FIG. 40. After the procedure in FIG. 40 was followed, the new expressions for $\mu_a$skin($\lambda$), $\mu_s'460$(maturity), and $\mu_s'650$(maturity), were obtained, and are presented below. These values are included in Table 5.2 where the final algorithm to deduce the cutaneous bilirubin concentration is presented.

5.5.3 Results

The fraction $\mu_a$bili/[Bili]$_{serum}$ is plot as a function of Melanin650 and $\mu_a$ $_{blood}$ in FIGS. 38a and b, respectively. The data for these graphs were generated using the final functions for $\mu_a$skin, $\mu_s'460$(maturity), $\mu_s'585$(maturity), $\mu_s'650$(maturity). These functions are:

$$\mu_a\text{skin} = a \exp(-b\lambda) = 27 \exp(-0.0006\lambda) \text{ (cm}^{-1}) \quad (5\text{-}18)$$
$$\mu_s'460 = \text{yint}_{460} + \text{slope}_{460}(\text{maturity}) \quad (5\text{-}19)$$
$$= -15.9 + 1.5 \text{ (maturity) (cm}^{-1})$$
$$\mu_s'585 = \text{yint}_{585} + \text{slope}_{585}(\text{maturity}) \quad (5\text{-}20)$$
$$= -12.0 + 1.1 \text{ (maturity) (cm}^{-1})$$
$$\mu_s'650 = \text{yint}_{650} + \text{slope}_{650}(\text{maturity}) \quad (5\text{-}21)$$
$$= -6.0 + 0.68 \text{ (maturity) (cm}^{-1})$$

Equation 5-18 above expresses the absorption coefficient of skin as a function of wavelength ($\lambda$ in nm) in terms of parameters a and b. The reduced scattering coefficient of skin at 460 and 585, and 650 nm as a function of maturity (in weeks) are expressed in Equations 5-19 and 5-20, and 5-21 above.

Also shown in FIG. 38a and b are the values of $\mu_a$bili/[Bili]$_{serum}$ as a function of Melanin650 and $\mu_a$blood calculated using the original expressions for optical coefficients (Equations 5-14, 5-16 and 5-16 and 5-17). From these graphs the Score$_{blood}$ and Score$_{melanin}$, and consequently the total Score was calculated.

Figures 41A, 41B:
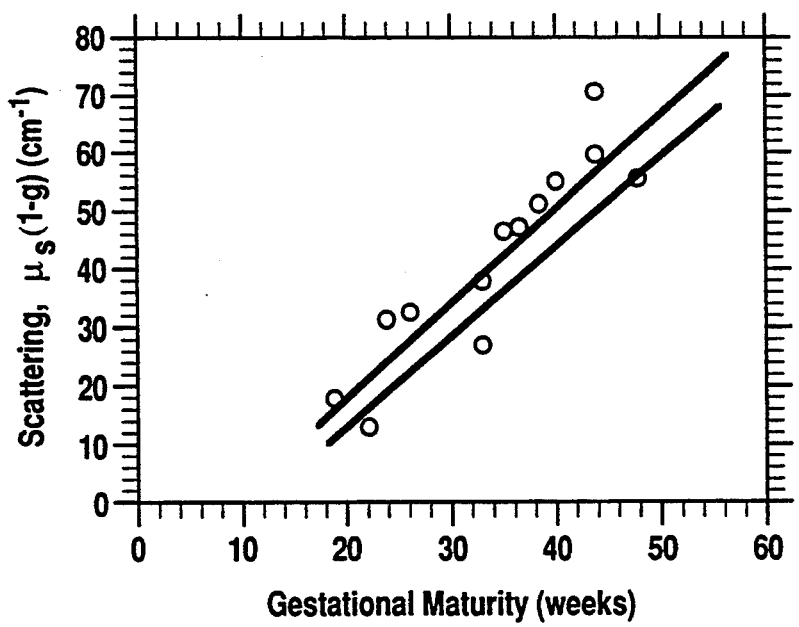
FIG. 41A is a two dimensional array showing the variation of total score as a function of parameters defining the relationship between reduced scattering coefficient and gestational age.
FIG. 41B is a graph of the scattering coefficient of skin at 460 nm as a function of gestational maturity.

FIG. 41a illustrates how the Score varies as the parameters that define $\mu_s'460$(maturity) namely, yint$_{460}$ and slope$_{460}$, were varied. The FIG. 41b shows how the new estimate of $\mu_s'460$ as a function of maturity, shown in Table 5.2, compares to the original function shown from Equation 5-14. FIG. 41b also shows the in vitro measurements of $\mu_s'460$ as a function of maturity. It can be seen that the variation in the measured $\mu_s'460$ and the final expression used in the algorithm is on average less than 10%, which is within the error with which we can optical properties from in vitro measurements. A graph showing how the new function for skin absorption as a function of wavelength compares with data measured in vitro was shown in FIG. 6. The difference between the final values of optical properties arrived at here, and the in vitro measurements may be contributed to due to differences in hydration between in vitro skin samples and in vitro skin. The difference between the initial and final values of the scattering coefficient at 585 nm was also less than 10%.

5.6 Estimate Of Errors

When the cutaneous bilirubin concentration is determined from the transcutaneous reflectance measurements, there is a degree of uncertainty in the bilirubin determination because of intersubject as well as intrasite variations in measurements. Intrasite variation means the variation in reflectance measurements performed repeatedly on the same in vitro skin site on a single subject. Intersubject variations are possible variations in skin properties between individuals, which will lead to changes in the cutaneous bilirubin determinations. To estimate the uncertainty with which the cutaneous bilirubin concentrations are reported, the cutaneous bilirubin concentrations were determined under a variety of conditions.

To estimate the uncertainty caused by simple measurement (intrasite) variation, the algorithm was used to predict the cutaneous bilirubin concentration for ten measurements performed on the same patient at the same skin site. All the ten measurements were performed in a three-minute period. The standard deviation in the calculated cutaneous bilirubin concentrations, and in the equivalent serum bilirubin concentrations, are reported in Table 5.3.

TABLE 5.3

| | Estimated Standard Deviation (+ S.D.), (% Variance) | Effect on Predicted Cutaneous Bilirubin Absorption Coefficient, + S.D. | Effect on Predicted Serum Bilirubin Concentration, + S.D. |
|---|---|---|---|
| Measurement (f*R) | +4% | ±0.188 (cm$^{-1}$) | ±0.69 (mg/dl) |
| Skin Thickness | +250 μm | ±0.095 (cm$^{-1}$) | ±0.35 (mg/dl) |
| Scattering Coefficient | +15% | ±0.414 (cm$^{-1}$) | ±1.51 (mg/dl) |
| Absorption Coefficient | +15% | ±0.225 (cm$^{-1}$) | ±0.82 (mg/dl) |
| Cumulative Standard | | ±0.516 (cm$^{-1}$) | ±1.88 (mg/dl) |

TABLE 5.3-continued

| Estimated Standard Deviation (+ S.D.), (% Variance) Deviation | Effect on Predicted Cutaneous Bilirubin Absorption Coefficient, + S.D. | Effect on Predicted Serum Bilirubin Concentration, + S.D. |
|---|---|---|

The main sources of intersubject variations that can lead to errors in the transcutaneous bilirubin determinations are skin thickness, and skin optical property estimates, as discussed in Section 4. Skin thickness is partially corrected for by lowering the estimated reflectance from skin of given optical properties in the algorithm iteration procedure, as discussed in Appendix C. Variation in the skin thickness, however, can still yield intersample variation in the etimated skin reflectance.

To determine the effect of skin thickness variation on transcutaneous bilirubin concentrations, the bilirubin algorithm was run on all the clinical samples with the measured reflectance adjusted according to the changes expected due to variation in skin thickness. The skin thickness was simulated to vary by 250 μm, the standard deviation in the mean skin thickness measured on in vitro skin samples on viable neonates (>24 weeks gestation). The resulting variation in the cutaneous and serum bilirubin estimates is reported in Table 5.3.

To determine the effect of skin optical properties on the transcutaneous bilirubin concentrations, the bilirubin algorithm was run on the clinical measurements with the scattering coefficient, and then with the absorption coefficient, used in the algorithm altered by ±15%. This is the estimated precision with which we can predict the optical coefficients for skin of given gestational age. The resulting variation in the bilirubin concentrations are shown in Table 5.3. Variation in skin absorption coefficients will directly lead to changes in the calculated absorption coefficient that is attributed to bilirubin.

Figure 38B:
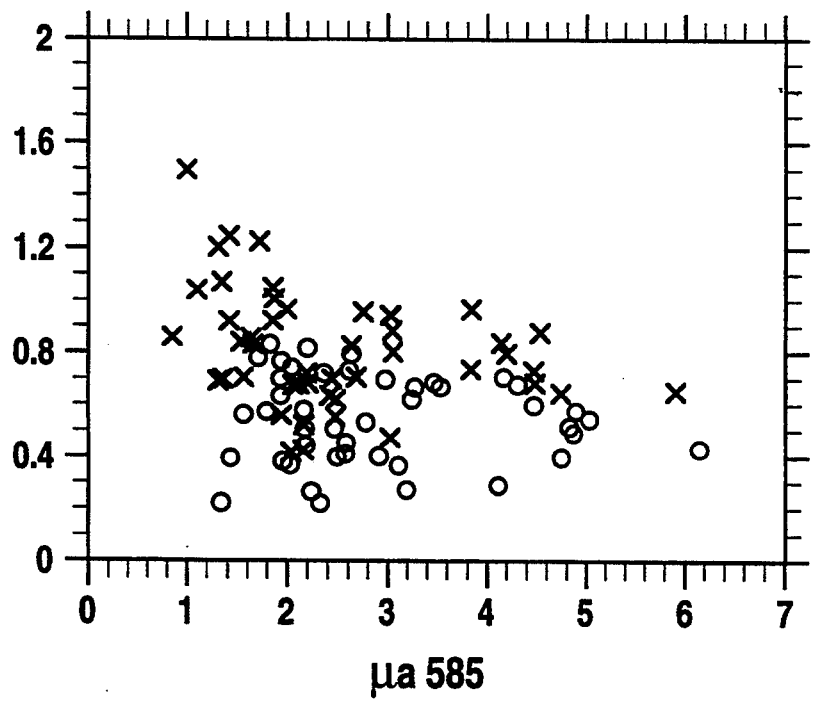

The cumulative uncertainty by which the cutaneous and serum bilirubin concentrations are reported was calculated by the vector sum of the individual sources of errors, and is shown in Table 5.3. This assumes linearity of relationships around the region of clinical interest. The error of ±0.516 cm$^{-1}$ (or 1.88 mg/dl) is small relative to the range of cutaneous and serum bilirubin concentrations encountered clinically (see FIGS. 38A and 38B).

5.7 Conclusions

Based on the Monte Carlo model of cutaneous bilirubin developed in this section, the measurements presented on neonates, and the considerations developed in the previous sections, an algorithm was developed that took the following into account.

Melanin in the epidermis behaves as a thin attenuation filter, decreasing the reflected signal in a linear fashion. This is very different from the effect that bulk tissue absorbers have on the reflectance of a tissue.

The scattering properties of the skin influence the interpretations of measured reflectance spectra. Therefore, the variable scattering has to be taken into account when determining the bilirubin concentration in skin. The maturity of the skin, from which the scattering properties are derived, can be determined by extrapolating the measured optical density spectra to 837 nm.

The effects of bulk tissue absorption in the dermis due to skin, bilirubin, and blood on the measured optical density do not accumulate linearly. For correct determination of the cutaneous bilirubin concentration, the total absorption in the skin at chosen wavelengths has to be determined correctly from radiative transport theory. Only then can the absorption due to skin, blood and bilirubin be analyzed linearly.

An algorithm was developed to determine the cutaneous bilirubin concentration with all these light transport considerations in mind. The different scattering properties of skin of neonates of different gestational ages, and the different melanin and blood content of the skin are all considered. The operation of the algorithm was demonstrated on reflectance measurements conducted on a clinical population. This is the first algorithm, aimed at determining the cutaneous bilirubin concentrations by determining the optical absorption coefficient of bilirubin in the skin.

Appendix A

Optical Interaction Parameters

A.1 Optical Coefficients

The rate at which energy is absorbed and scattered by a particle is the energy extinction rate, $W_{ext}$, of the particle, expressed in watts. The extinction rate $W_{ext}$ is comprised of $W_a$ and $W_s$, which are the energy absorption and the energy scattering rates of the particle.

The extinction cross section, $C_{ext}$ (cm$^2$), is defined as the ratio of $W_{ext}$ (W) to the incident fluence rate, $I_i$ (W/cm$^2$), and similarly the absorption cross section and scattering cross section are defined:

$$C_a = \frac{W_a}{I_i} \text{ and } C_s = \frac{W_s}{I_i} \quad \text{(A-1)}$$

The extinction, absorption, and scattering cross sections have dimensions of square area, and are related by:

$$C_{ext} = C_a + C_s \quad \text{(A-2)}$$

In a medium containing a concentration $\rho$ of such particles per unit volume, the extinction, absorption, and scattering coefficients of the medium are defined as:

$$\mu_{ext} = \mu_t = \rho C_{ext} \quad \text{(A-3)}$$

$$\mu_a = \rho C_a \quad \text{(A-4)}$$

$$\mu_s = \rho C_s \quad \text{(A-5)}$$

The extinction coefficient of the medium, $\mu_{ext}$, is sometimes referred to as the total attenuation coefficient, $\mu_t$, and is equal to the sum of $\mu_a$ and $\mu_s$. These interaction coefficients have units of inverse distance, such as cm$^{-1}$.

The light distribution in a tissue is determined by the optical characteristics of the tissue which include its optical properties, thickness, and geometry. For a slab of arbitrary thickness, the problem is 1-dimensional, and optical characteristics are described either in dimensional or non-dimensional units, as shown in table A-1 below:

TABLE A-1

| Dimensional | | Non - Dimensional | |
|---|---|---|---|
| Absorption | $\mu_a$ (cm$^{-1}$) | Albedo | $a = \dfrac{\mu_s}{\mu_a + \mu_s}$ |
| Scattering | $\mu_s$ (cm$^{-1}$) | Optical depth | $b = (\mu_a + \mu_s)d$ |

TABLE A-1-continued

| Dimensional | Non - Dimensional |
|---|---|
| Thickness d (cm) | |

A.2 Anisotropy

The anisotropy factor, sometimes referred to as the asymmetry parameter, g, is equal to the average cosine of the angle of scattering $\theta$.

$$g = <\cos\theta> \cong \int_0^\pi p(\theta) \cos(\theta)\, 2\pi \sin\theta\, d\theta \quad \text{(A-6)}$$

where $p(\theta)$ is the scattering phase function in a fixed plane, and is subject to the following constraint to conserve photon energy:

$$\int_0^\pi p(\theta)\, 2\pi \sin\theta\, d\theta = 1 \quad \text{(A-7)}$$

The anisotropy factor, g, is a measure of the directionality of the scattered light, and varies from 0 for isotropically scattered light to 1 for forwardly scattered light.

A.3 Light Transport

Combining $\mu_s$ and $(1-g)$ as the product, $\mu_s(1-g)$, gives the reduced scattering coefficient, also referred to as $\mu_s'$. The reduced scattering coefficient, is used in diffusion theory to specify the effective light scattering that determines light penetration into a medium [Ishimaru 1978]. The reduced scattering coefficient is a useful parameter which can be used to describe the effective scattering in a tissue without uniquely solving for both $\mu_s$ and g individually in a tissue.

In a one dimensional situation, for light, $I_0$, traveling a distance x in the tissue with optical interaction parameters $\mu_a$ and $\mu_s$, the amount of light that is neither absorbed nor scattered as a function of x is given by:

$$I(x) = I_0 e^{-(\mu_a + \mu_s)x} \quad \text{(A-8)}$$

In three dimensional space, the diffusion equation can be solved far from a light emitting point source. The fluence rate, $\phi(r)$, specified in Watts/cm², is given by [Patterson 1990]:

$$\phi(r) = \frac{1}{4\pi D} \frac{\exp(-\mu_{eff} r)}{r} \quad \text{(A-9)}$$

where r is the distance from the delta function point source, D is the diffusion constant and is given in Equation A-10, and $\mu_{eff}$ is the effective coefficient and is given in Equation A-11.

$$D = \frac{1}{3(\mu_a + \mu_s(1-g))} \quad \text{(A-10)}$$

$$\mu_{eff} = \sqrt{3\mu_a(\mu_a + \mu(1-g))} \quad \text{(A-11)}$$

Appendix B

Calculation of Optical Patch Collection Efficiency from Monte Carlo Results

B.1 Introduction

The collection efficiency of the optical patch, or other optical delivery and collection device with specified geometry, can be determined by convolution of the Monte Carlo radial reflectance profile. The calculations involved to determine the collection efficiency are presented here for the optical patch described in section 3. The convolution procedure presented can be applied to any optical devices in which the collection and delivery areas are concentric.

B.2 Convolution Procedure

The light delivered through the optical patch is delivered through the delivery area. The Monte Carlo point source reflectance response of the tissue has to be convolved over the whole delivery area to determine the light collection efficiency of the optical patch.

Figure 42:
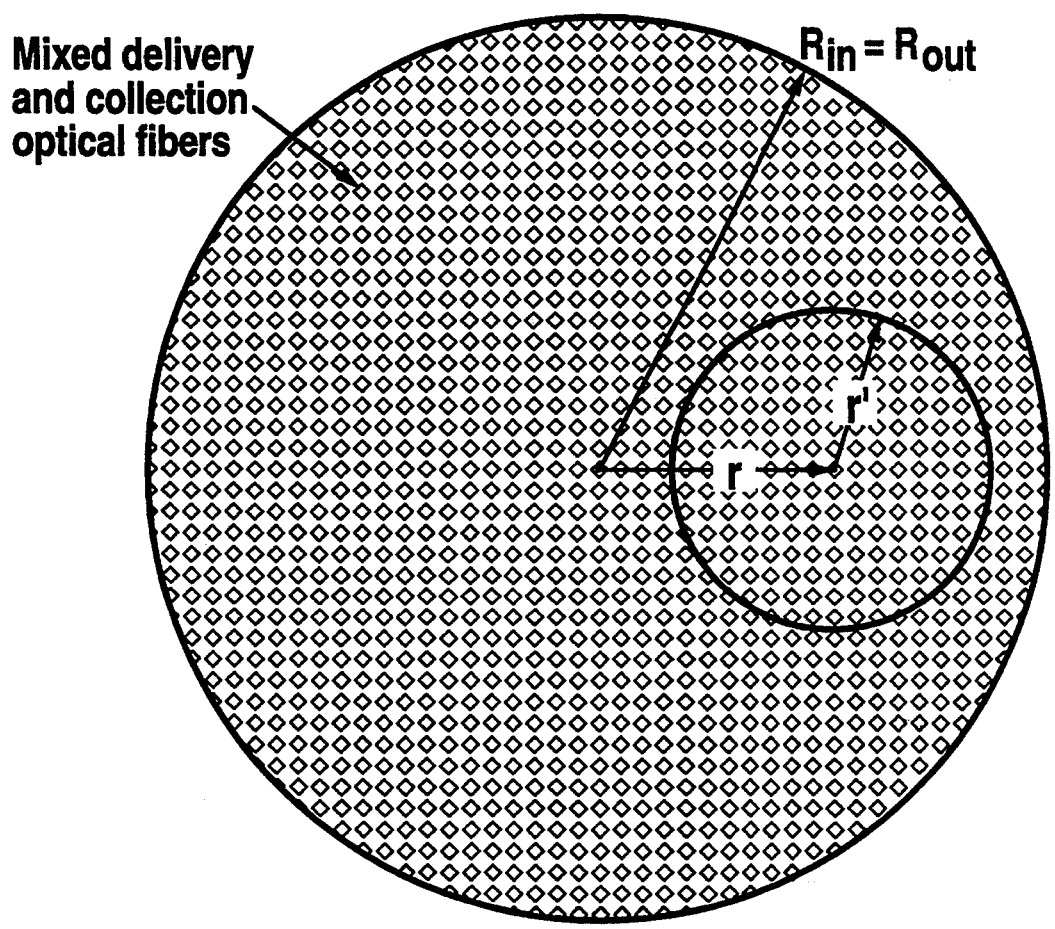
FIG. 42 illustrates the parameters used to describe the collection of light by the optical patch of FIG. 8A.

FIG. 42 defines the geometry of the collection and delivery areas used in the general convolution procedure described. The delivery area is the circular area with radius $R_{in}$. Similarly, the collection area is defined as the circular area with radius $R_{out}$ as illustrated. This procedure is designed to calculate the collection efficiency in an optical patch in which the delivery and collection areas are two full concentric circles. The radiuses of the delivery and collection areas, $R_{in}$ and $R_{out}$, can be different.

The light delivered through the optical patch equals the integral of irradiance, $E_o$ (W/cm²), over the entire delivery area of the optical patch. Therefore the light delivered by the optical patch can be expressed as:

$$\text{Total light deliverd} = \int_0^{2\pi} \int_0^{R_{in}} E_0\, r\, dr\, d\theta \quad \text{(B-1)}$$

$$= E_0 \int_0^{R_{in}} 2\pi\, r\, dr\, d\theta \quad \text{(B-2)}$$

The total collection efficiency of the optical patch, f, is calculated as:

$$f = \frac{\text{Total light collected}}{\text{Total light delivered} + \text{Total light lost}} \quad \text{(B-3)}$$

To calculate the collection efficiency, f, the total light collected, C(r), and lost, L(r), from each input radial point, r, is determined. The quantities C(r) and L(r) are expressed in watts. To calculate C(r) and L(r), for each value of the input radius, r, the output radius, r', is incremented from 0 to ∞, as to sum all the reflected light. The fraction of reflected light that is collected depends on r, and r', as seen in the three cases described below.

The integration parameters are illustrated in FIG. 42. The input irradiance is can be normalized to 1 (W/cm²). The light collected is then expressed as fractions of the delivered light energy. In the following calculations, the reflection profile, R(r'), gives the amount of light that is reflected in the whole annulus with radius r', and so is specified in units of W/cm. The total power delivered in the annulus with radius r' and thickness $\Delta t'$ is equal to the product $R(r')\Delta r'$.

Figure 43A:
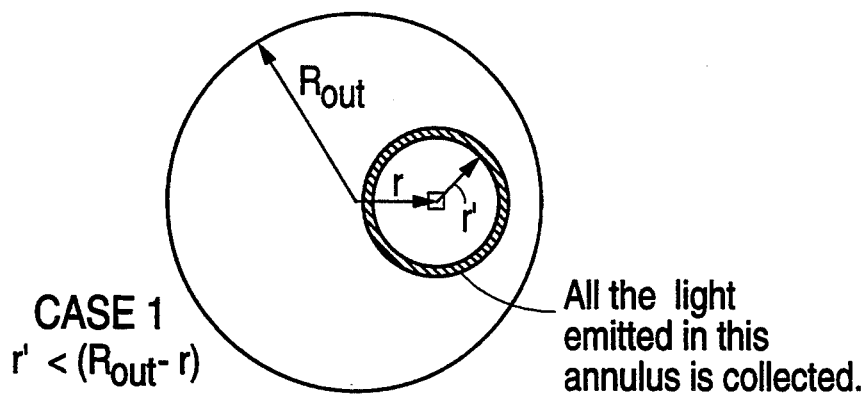
FIGS. 43A, B and C illustrate the three cases of the geometry of collection of light by optical patch of FIG. 8A.

Case 1 (FIG. 43A): If $r' < (R_{out} - r)$ then, as diagramed in FIG. 43A, all the light reflected at radius r' is collected by the optical patch. Therefore, $$\text{collected}_1 = \int_0^{R_{out} - r} R(r')\, dr' \quad \text{(B-4)}$$

$$\text{lost}_1 = 0 \quad \text{(B-5)}$$

Figure 43B:
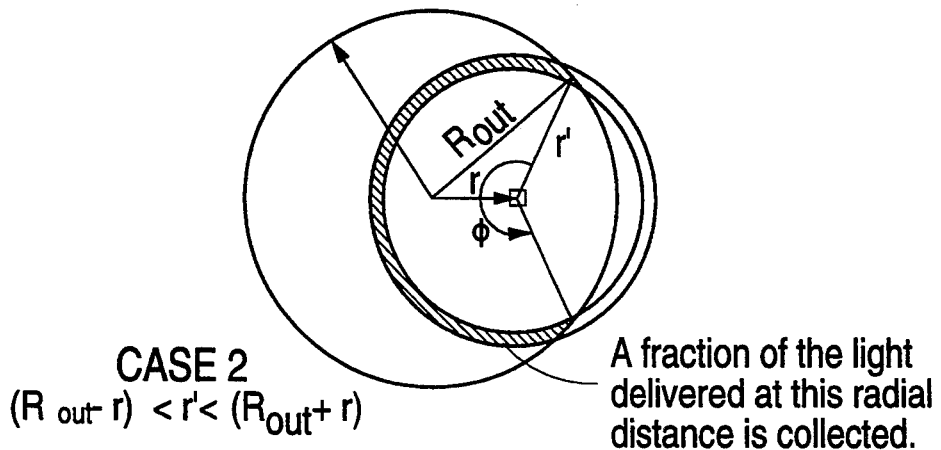

Case 2 (FIG. 43B): If $(R_{out}-r) < r' < (R_{out}+r)$ then, as diagramed in FIG. 43B, a fraction of the light reflected at radius r' is collected by the optical patch. Therefore, $$\text{collected}_2 = \int_{(R_{out} - r)}^{(R_{out} + r)} R(r') \frac{\phi(r',r)}{2\pi} dr' \quad \text{(B-6)}$$

where $\phi(r',r)$ is the angle shown in FIG. 43b, and is equal to:

$$\phi(r',r) = 2 \cos^{-1}\left( \frac{r'^2 + r^2 - R_2^2}{2 r r'} \right) \quad \text{(B-7)}$$

The angle $\phi$, in equation B-7 was derived by application of the cosine law which states that in a triangle with sides a, b, and c, the following relationship holds:

$$c^2 = a^2 + b^2 - 2ab\cos\gamma \quad \text{(B-8)}$$

where $\gamma$ is the internal angle in the triangle that projects side c. For derivation of Equation B-7 from B-8, $\phi/2$ was set as $\gamma$, r was set to a, r' was set to b, and $R_{out}$ was equal to c (See FIG. 43B).

The remaining light remitted in the radial range, r', that is not collected by the optical patch is lost. Therefore:

$$\text{lost}_2 = \int_{(R_{out} - r)}^{(R_{out} + r)} R(r')\left(1 - \frac{\phi(r',r)}{2\pi}\right)dr' \quad \text{(B-9)}$$

Figure 43C:
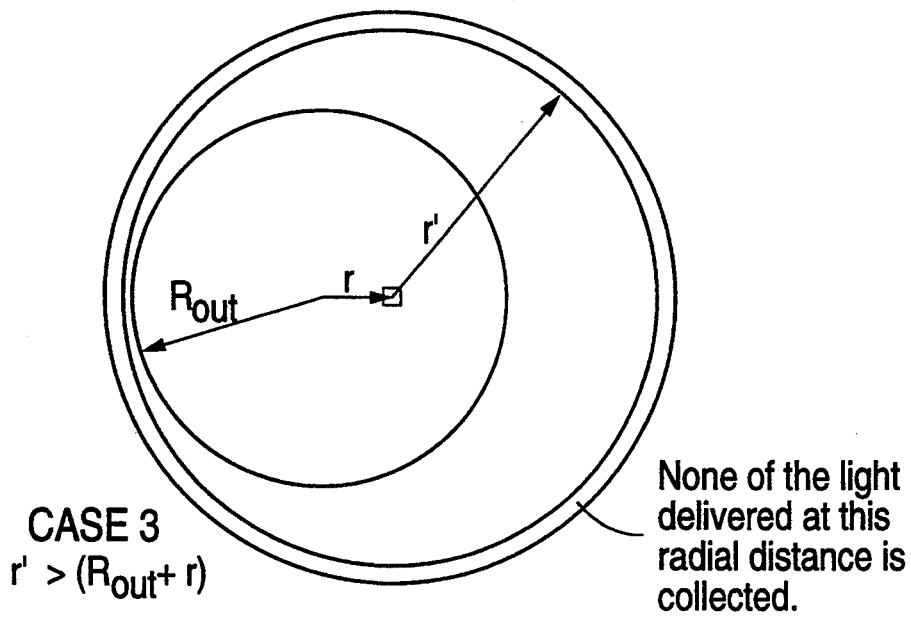

Case 3 (FIG. 43C): If $r' > (R_{out}+r)$ then, as diagramed in FIG. 43C, none of the light reflected at radius r' is collected by the optical patch. Therefore:

$$\text{collected}_3 = 0 \quad \text{(B-10)}$$

$$\text{lost}_3 = \int_{(R_{out} + r)}^{\infty} R(r') dr' \quad \text{(B-11)}$$

The total light, C(r), delivered at radius r, that is collected by the optical patch is therefore equal to:

$$C(r) = \text{Collected}_1 + \text{Collected}_2 \quad \text{(B-12)}$$

The total light, L(r), delivered at radius r, that is reflected outside the optical patch and so is not collected is equal to:

$$L(r) = \text{lost}_2 + \text{lost}_3 \quad \text{(B-13)}$$

The total collection efficiency, f, of the optical patch can then be given as:

$$f = \frac{\text{total collected light}}{\text{total collected light + total lost light}} \quad \text{(B-14)}$$

$$= \frac{\int_0^{R_{in}} C(r) 2\pi r \, dr \, d\theta}{\int_0^{R_{in}} C(r) 2\pi r \, dr \, d\theta + \int_0^{R_{in}} L(r) 2\pi r \, dr \, d\theta} \quad \text{(B-15)}$$

The Monte Carlo data described in subsection 3.4, is used with the geometry described above to determine the optical patch collection efficiency, f. The next two sections describe the use of the Monte Carlo data in implementation of a computer program to determine f.

B.3 Monte Carlo Method and Approximations

The basis of the Monte Carlo data used in this convolution procedure is described in subsection 3.4. The program simulates the launching of photons with unit weight, W=1, into an absorptionless medium. Each time a fraction of the photon weight is remitted, the Monte Carlo program stores in a file ("photon history file") the radial distance from the source at which the photon was remitted (m), the fraction of the photon weight that was remitted (fraction of 1), the pathlength travelled by the photon in the absorptionless medium (m), the maximum depth in the medium reached by the photon (m, not used in the convolution procedure), and the average depth reached in the medium by the photon (m, not used in the convolution procedure). The Monte Carlo simulation also stored the total number of photons launched into the medium, and the scattering coefficient used during the simulation. The distances stored in the photon history file can subsequently be converted to centimeters (see subsection 3.4.2 for details), or effective scattering lengths (as is described in the convolution program in this appendix).

The photon histories stored during the Monte Carlo computer simulations are intended to predict the reflection response of an infinitely thick medium (See subsection 3.4 for introduction). Monte Carlo simulates each scattering event that a photon experiences. To get an accurate assessment of the total tissue response to photons, many photons need to be simulated, and the process is time consuming. This is especially true in the case of a thick absorptionless medium, where the photon record is dropped only by reflection or transmission of the photon, but not by absorption. To prevent excessively long Monte Carlo simulations, the thickness was made finite, and equal to approximately sixty effective scattering lengths (or 300 mean scattering path lengths (g=0.8)). With this thickness assigned to the absorptionless medium simulated by Monte Carlo, approximately 4.5% of the photons were transmitted through the medium, 2.5% were laterally transmitted, and the remaining 93% were reflected. The transmission through this medium will result in a small approximation error in the calculation of the optical patch collection efficiency, since it assumes an infinitely thick medium through which there is no transmission. This error is estimated below.

Figure 44:
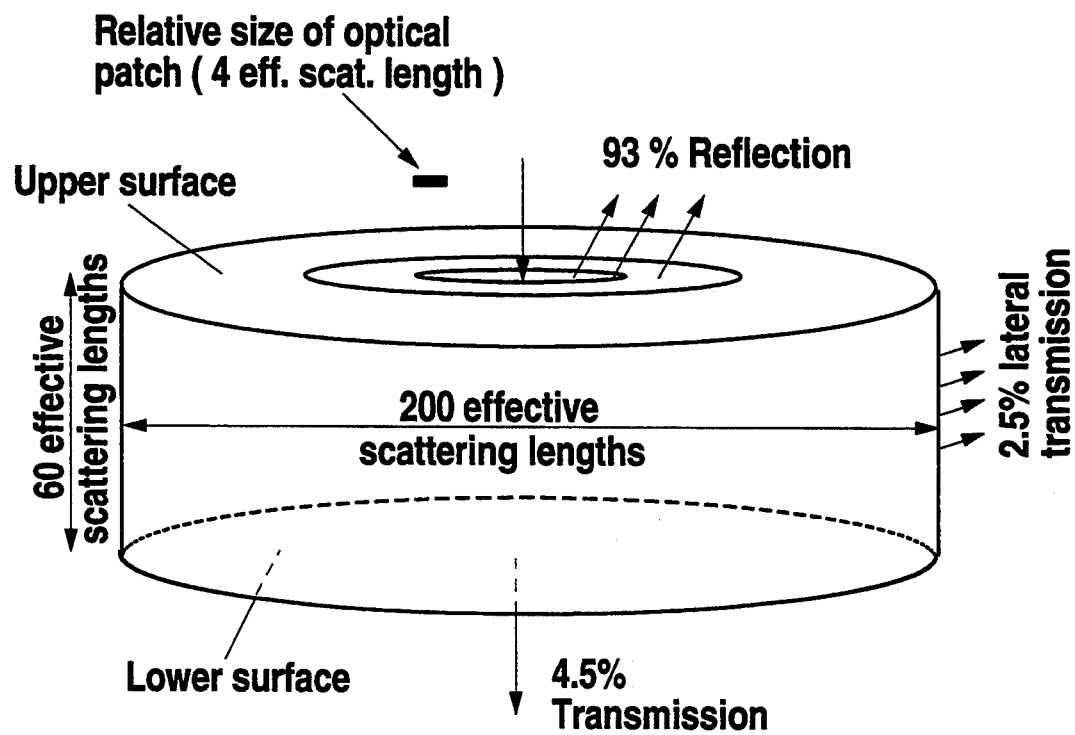
FIG. 44 illustrates the relative dimensions of the absorptionless medium modeled by the Monte Carlo simulation of the present invention.

FIG. 44 shows the geometry of the Monte Carlo model used. As discussed in Section 3, the distances in the Monte Carlo model can be converted to dimensionless units, and so a wide range of dimensions can then be modelled from the same Monte Carlo results. The dimensions in FIG. 44 correspond to typical optical properties of $_a$ of 1 cm$^{-1}$ and $_s'$ of 20 cm$^{-1}$.

In a medium in which $_s' = 20$ cm$^{-1}$ then an absorption coefficient, $_a = 1$ cm$^{-1}$, corresponds to: $1/20 = 0.05$ effective scattering lengths. In a worst case scenario, if the 7% transmitted light in the Monte Carlo model had an unscattered path in the medium, then after absorption the amount of light that was transmitted corresponds to:

$(0.07) * e^{(-0.05*60)} = 0.0035$ fraction of the light that was input into the medium. This calculation assumes 60 effective scattering lengths for the depth and radius of the medium modelled by Monte Carlo, which is worse than the real case.

If this light was actually reflected from the lower surface of the medium, rather than being transmitted, then after absorption on the return trip before remission from the upper surface, the fraction of the input light that is remitted can be estimated as:

$0.0035 * e^{(-0.05*60)} = 1.73 \times 10^{-4}$ fraction of the light input into the medium.

The optical patch collection efficiency, f, is calculated as (from equation B-3):

$$f = \frac{\text{collected}}{\text{collected} + \text{lost}} \quad \text{(B-3)}$$

With the optical properties defined above, the approximate reflection of the tissue is approximately 40% (from equation 3-28). Therefore, the term (collected+lost) in the denominator of equation B-3 is equal to 0.4. The collection efficiency, f, is approximately equal to 0.6 (from Equation 3-21). From equation B-3, the fraction of the light input by the patch that is lost can be solved to equal 0.24, and the fraction that is lost equals 0.16.

In a worst case scenario, the light that was transmitted in the absorptionless case actually rebounded from the lower surface (see FIG. 44), and remitted from the upper surface after absorption, as discussed. Also, as a worst case, if this light was remitted from the upper surface such that it was not collected by the optical patch, then the f would be:

$$f = \frac{0.24}{0.24 + 0.16 + (1.73 \times 10^{-4})}$$

This implies a 0.04% error in the calculation of f due to the approximation of an infinite medium. This error will vary with optical properties, but 0.04% is a conservative estimate since it assumes worst cases.

B.4 Computer Implementation of Convolution Procedure

The collection fraction, f, is determined as the fraction of light that is collected divided by the sum of collected and lost light (see Equation B-3). The lost light refers to light that was remitted beyond the collection area of the optical patch. To determine the collected and the lost light, the profile of reflected light has to be determined. This profile of reflected light is then used in the convolution procedure (R(r') in equations B-4 through B-11). In the computer program application of the convolution procedure, the reflection profile is made discrete, and placed in an array called Refwtotalab, as explained below.

The photon histories file contains the location of remission of each photon, r_em, the fractional weight of the photon remitted, w, and the pathlength of the photon travel in the absorptionless medium (see subsection 3.4 for more complete discussion). The distances expressed in the, in m, are converted to average effective scattering lengths, by multiplication by the effective scattering coefficient, $s'_0$ used in the Monte Carlo simulation during generation of the photon histories file. For example:

r_em(eff. scat.
  lengths)=r_em($\mu$m)*0.0001(cm/$\mu$m)*$\mu_s'_0$(cm$^{-1}$) (B-16)

The photon weight remitted for each photon is then calculated, as in equation 3-18. Each photon weight remitted is added to the appropriate element of the array Refwtotalab[index], where index is assigned to the radius of photon remission, r_em, by the programming statement:

$$index = round((r\_em - (delta\_r/2))/delta\_r) \quad \text{(B-17)}$$

where delta_r is the resolution with which the reflection profile is made discrete. Delta_r is expressed in the same units as r_em, either m or effective scattering lengths.

All index values greater than a set number, indexmax, are assigned as indexmax+1. This allows for the limiting of the number of discrete elements in the array Refwtotalab, without the loss of resolution at the radii of interest.

When all the remitted photons are added to the appropriate Refwtotalab array elements, the the total light reflected is accounted for in the sum of the Refwtotalab elements, as shown below:

$$\sum_{0} Refwtotalab[\text{index}] = \text{total light reflected} = \text{collected} + \text{lost} \quad \text{(B-18)}$$

The light that is reflected and collected by the optical patch, and the light that is reflected but not collected (lost), are counted individually in convolution procedure. They are used to determine the collection efficiency, f, as in Equation B-3. An example of a Pascal program implementation of the convolution procedure using Monte Carlo data is presented below.

B.3 Computer Implementation of Monte Carlo Convolution program MctrackscalRr

```
{Program to calculate optical patch collection efficiency from
absorptionless Monte Carlo photon histories}
{Iyad Saidi,
Laser Biology Research Laboratory, UT-M.D. Anderson Cancer
Center}
{subprograms used sane contains arithmetic functions}
  uses
    sane
  var                                              {variables used}
    r_em: real                      {radial distance from source at which
                                                    photons remitted}
    refwnoabs: real                    {weight of photon remitted with no
                                              absorption taken in to account}
    refwabs: real                         {weight of photon remitted after
                                              absorption taken into account}
    L: real                   {Pathlength of photon in absorptionless medium}
    delta_r: real                  {radial interval in which r_em is discretized}
    refwabstotal: real               {sum of photon weights after absorption}
```

-continued

| | |
|---|---|
| musg: real | {$s'$ specified} |
| mua: real | {$a$ specified} |
| photosin: real | {number of photons input to absorptionless Monte Carlo simulation} |
| musgfile: real | {s' specified when absorptionless Monte Carlo run to generate photohistory file, ($s'_0$ in text} |
| Rin: real | {Radius of delivery circular area of optical patch} |
| Rout: real | {Radius of collection circular area of optical patch} |
| fraction: real | {fraction of delivered light that is collected in case 2 situation} |
| collected: real | {Variable to sum collected light input at radius r, (equivelant to C(r)} |
| lost: real | {Variable to sum lost light input at radius r, (equivelant to L(r)} |
| totalcollected: real | {Sum of collected light (equivelant to integral of C(r)} |
| totallost: real | {Sum of lost light (equivelant to integral of L(r)} |
| dummy: real | {read from photon history file but not used} |
| i: integer | {index to keep track of photon histories read} |
| indexmax: integer | {max. number of radial descretizations} |
| i__r: integer | {discrete radius of delivery annulus (r)} |
| i__rprime: integer | {discrete radius of collection annulus (r')} |
| i__Rin: integer | {discrete radius of delivery area of patch (Rin)} |
| i__Rout: integer | {discrete radius of collection area of patch (Rout)} |
| index: integer | {index used to discretize reflection profile R(r)} |
| filename: string | {name of file which contains photon histories} |
| junk: string | {string read but not used} |
| source: text | {source file alias} |
| refwtotalab: array[0 . . . 51]of real | {Array containing photon remission profile after absorption} |

{Subroutine to find inverse cosine}
function Arccos (x: extended): extended
    begin
        Arccos := 2 * Arctan(sqrt((1 − x) / (1 + x)))
        {spurious divide-by-zero may arise}
    end
{begining of procedure}
begin
{read in reduced scattering coefficient desired}
    writeln('what is s(1−g) in inverse cm')
    readln(musg)
{read in absorption coefficient desired}
    writeln('what is a in inverse cm')
    readln(mua)
mua: = mua / (musg)                           {mua in units of mean
                                               effective scattering lengths}
{Specify dimension of optical patch}
    Rin := 1.05 {Radius in which there are input fibers (mm)}
    Rin := Rin / 10 {cm}
    Rout := 1.05 {Radius in which there are output fibers (mm)}
    Rout := Rout / 10 {cm}
(open file which contains Monte Carlo photon histories at
reflection}
    filename := oldfilename ('which file has the tracks data from
Monte Carlo')
reset(source, filename)
{read in the number of photons run, and the reduced scattering
coefficient with which it was run}
    readln(source, photosin, musgfile)
    readln(source, junk)
{set number of photons read = 0}
    i := 0
    indexmas := 25
{set arrays = }
    for index := 0 to (indexmax + 1) do
        begin
            Refwtotalab[index] := 0
        end
    {chose rbucket size =Max radius encountered in patch of
interest so that resolution is not wasted, (Rin + Rout) is the
maximum possible encountered distance in patch to be collected
in dimensionless units of effective scattering lengths}
    delta__r := (Rin + Rout) * musg / (indexmax − 2)
I__Rout := Num2integer(Rout * musg / delta__r) {discrete form of
        distance of patch collection radius, Rout}
I__Rin := num2integer(Rin * musg / delta__r) {discrete form of
        distance of patch delivery radius, Rin}

-continued

```
{set photon counts to zero, for absorptionless and absorbed
cases}
      refwabstotal := 0
{input photon reflections from photon files}
      while not eof(source) do
         begin
            {count number of photon histories recorded}
            i := i + 1
            {read: radius of reflection, weight reflected, pathlength
of    travel maximum depth reached, and average depth in
            phantom using m for distances}
               readln(source, r_em, Refwnoabs, L, dummy, dummy)
            {convert m → cm → effective scattering lengths}
               r_em := r_em * musgfile * 0.0001
               L := L * musgfile * 0.0001
            {sum reflected light, in absorptionless and absorbed
case}
               refwabs := (refwnoabs * exp(-mua * L))
               refwabstotal := refwabstotal + refwabs
            {categorize r_em at which photons reflected in discrete
boxes, (indices), then sum reflection within each radius
index}
               index := round((r_em - (delta_r / 2)) / delta_r)
               if index < indexmax then
                  index := indexmax + 1
               Refwtotalab[index] := Refwtotalab[index] + Refwabs
         end
      close(source)
{Convolution to find optical path collection efficiencies}
      totalcollected := 0
      totallost := 0
{integrate total over all input radiuses}
      for i_r := 0 to i_Rin do
         begin
            collected := 0                              {the light collected
from this radial}
            lost := 0
{case 1, full circles collected}
            for i_rprime := 0 to (i_Rout - i_r) do
               begin
                  index := i_rprime
                  if index < indexmax + 1 then
                     index := indexmax + 1
                  collected := collected + Refwtotalab[index]
               end
{case 2, fraction of circles collected}
            for i_rprime := 0 to (i_Rout - i_r + 1) to
            (i_Rout + i_r) do
               begin
                  index := i_rprime
                  if index < indexmax + 1 then
                     index := indexmax + 1
                  fraction := Arccos((sqr(i_rprime) + sqr(i_r) -
sqr(i_Rin)) / (2              * i_r * i_rprime)) /
(pi)
                  if (i_r = 0) or (i_rprime = 0) then
                     fraction := 0
                  collected := collected + (Refwtotalab[index] *
fraction)
                  lost := lost + (1 - fraction) * (Refwtotalab[index])
               end
{case 3, All light is lost}
            for i_rprime := (i_Rout + i_r + 1) to indexmax + 1 to
{add remaining escaping fraction}
               begin
                  index := i_rprime
                  if index < indexmax + 1 then
                     index := indexmax + 1
                  lost := lost + (Refwtotalab[index])
               end
            {input area is * 2pi R}
            collected := collected * 2 * pi * i_r
            lost := lost * 2 * pi * i_r
            totalcollected := totalcollected + collected
            totallost := totallost + lost
         end {end the adding of i_r}
{write out results}
      writeln('fraction collected = ', totalcollected /
(totalcollected + totallost))
end.
```

Appendix C

Effect of Skin Thickness on Reflectance Measurements

C.1 Introduction

The neonates' skin thickness may vary between individuals and sites, as discussed in Section 4. FIG. 31 shows the thickness of the skin measured on the 20 in vitro neonatal skin samples discussed in Section 2. The algorithms presented in accordance with this invention were developed for infinite media, since the skin is optically thick. The effect of the skin thickness variation on the measured light reflection is studied in this appendix, and the potential errors in bilirubin estimation are analyzed.

Model of Skin Thickness Effect

C.2.1 Monte Carlo Model

As discussed in Section 4, the hypodermis, a fatty collagenous layer, lies below the dermis. Absorptionless Monte Carlo computer simulations were run, similar to the Monte Carlo simulations discussed in Section 3. The pathlength in each one of ten layers in the skin was stored for the remitted photons. The photon reflection profiles were analyzed varying optical properties in the skin. The optical properties of the individual layers were set at those of dermis, or hypodermis. The optical properties of dermis were estimated from optical measurements, and from the literature [Cheong 1991]. The scattering coefficient in the hypodermis is about half that of the dermis. The number of layers with dermal optical properties was varied depending on the desired thickness of the skin simulated. The true reflection and collection efficiency of the optical patch was calculated for each of the simulated skin thicknesses.

The thickness of the dermis above the hypodermis was varied between 600 and 1200 nm, which are the expected range of skin thicknesses of viable neonates (>24 weeks gestational age).

C.2.2 Results

Figure 45:
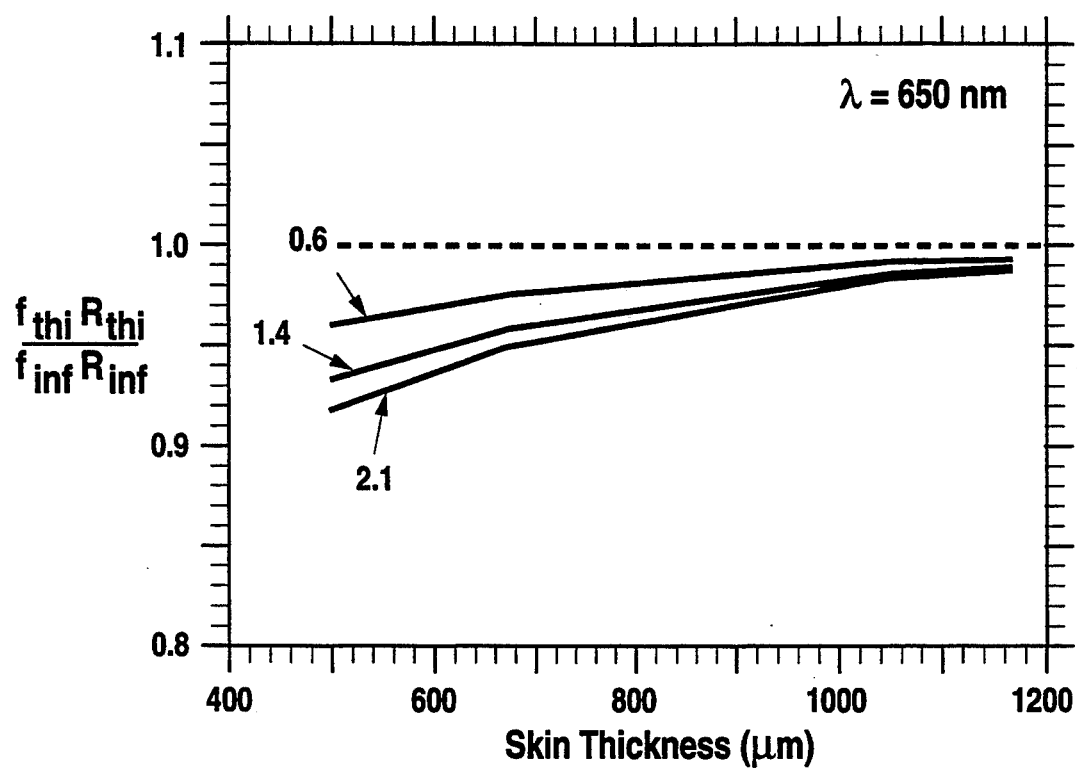
FIG. 45 is a graph of the measured reflection of skin of finite thickness as a fraction of the measured reflection of infinitely thick skin, displayed as a function of skin thickness.
Figure 46:
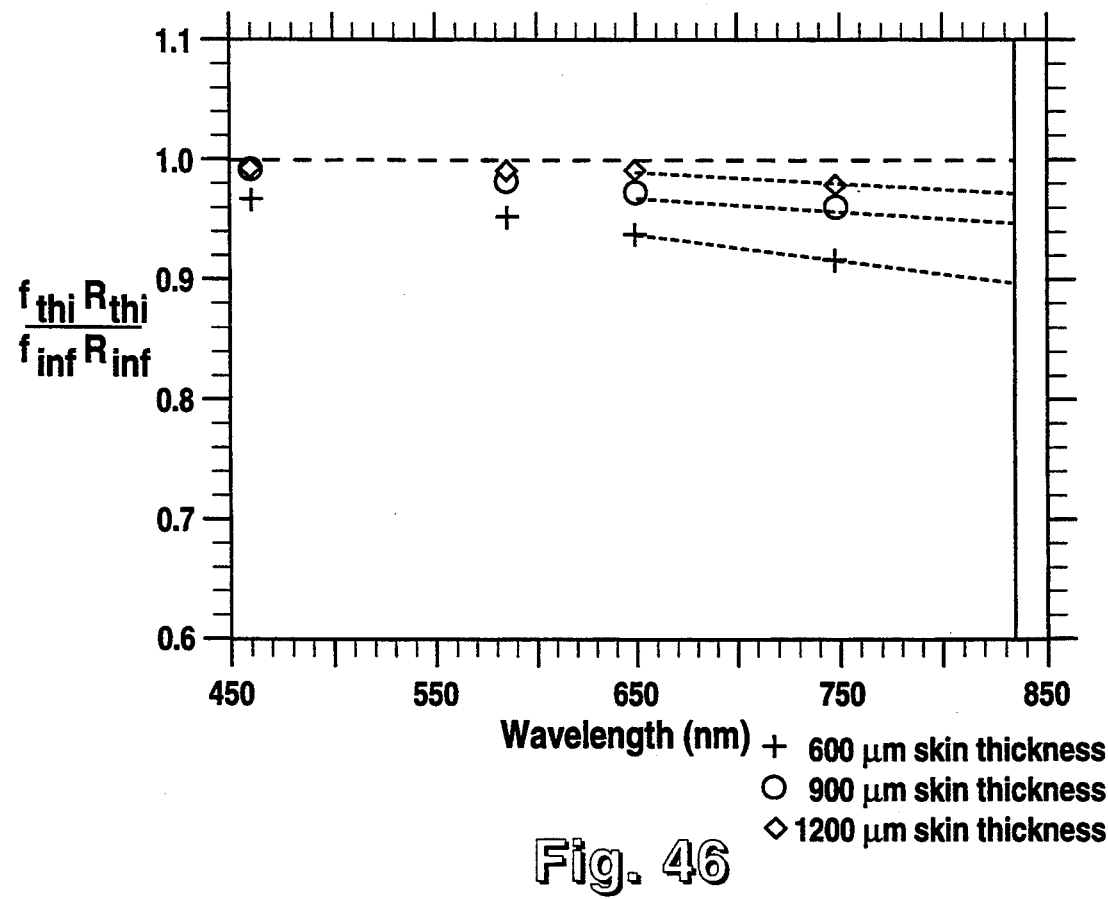
FIG. 46 is a graph of the measured reflection of skin of finite thickness as a fraction of measured reflection of infinitely thick skin, displayed as a function of wavelength.

As the thickness of the skin was decreased, the true reflectance of the tissue decreased while the fraction of reflected light collected by the optical patch increased. Consequently the measured reflectance was found to drop by less than the drop in the true reflection of the tissue. The effect of skin thickness and optical patch diameter on the measured reflection is illustrated in FIG. 45, for thirty week gestational age dermal optical properties at 650 nm. In this figure the measured reflectance of skin of finite thickness overlying hypodermis divided by measured reflectance for skin of infinite thickness is shown as a function of skin thickness. The decrease in skin reflectance measured with the 2.1 mm optical patch is less than 10% for the thinnest skin expected ($\approx 600$ μm). The effect skin thickness has on the reflectance measured with the optical patch increases with wavelength, since at the longer wavelengths, the tissue is optically thinner. FIG. 46 shows the fraction of measured reflectance of finite thickness skin relative to infinite thickness skin for the wavelengths 460, 585, 650, and 750 nm. At 460 and 585 nm, the variation in reflectance of very thin skin ($\approx 600$ μm) and very thick skin ($\approx 1200$ μm) is less than 3%.

The fraction of measured reflectance of finite thickness skin relative to infinite thickness skin for the 460-nm light is:

$$\frac{f_{thi}R_{thi}}{f_{inf}R_{inf}} = 1 - 0.28 \exp(-0.0035 t) \tag{C-1}$$

and for 585-nm light is:

$$\frac{f_{thi}R_{thi}}{f_{inf}R_{inf}} = 1 - 0.29 \exp(-0.0030 t) \tag{C-2}$$

where t is the thickness in μm.

C.2.3 Discussion

The measured reflectance does not drop as fast as the true total reflectance, because the addition of an absorbing layer beneath the skin would affect the photons that have penetrated deeply. These deep photons, on average, have a higher probability of remittance outside the collection area of the optical patch than do the more shallow penetrating photons. Therefore, the absorbing layer beneath the skin will not affect the photons that are remitted into the optical patch as much as it would affect, on average, all the remitted photons. This phenomenon will be of increased relevance with optical patches with smaller delivery and collection areas. As shown in this figure, the reflectance measurements performed between 650 and 750 nm, which are used to determine the skin maturity by extrapolation to 837 nm, are affected by skin thickness. However, an extreme variation in thickness between 600-nm thick and 1200-nm thick, still has a less then 10% variation in extrapolated reflectance at 837 nm. This compares to variation of 150% in the measured reflectance at 837 nm due to changes with gestational age, as seen from FIG. 20.

C.2.4 Conclusion

In conclusion, the thickness of the skin presents a potential source of error in the reflectance spectra measurements at the skin surface. Variation in the skin thickness may alter the reflectance measurements in the 650–750 nm range by up to 10%, which in turn will affect the interpretation of the skin maturity. Variation in the skin thickness will play a small role in readings in the 400–600 nm range (<3% variation) where blood and bilirubin absorbances are read. Finally, the existence of a hypodermis consisting of collagen fibers and fat beneath the dermis, and measurement of the reflectance with an optical patch rather than measurement of total reflectance, will both decrease the effect skin thickness has on the measured reflectance.

C.3 Partial Correction of Skin Thickness Error

Figure 47:
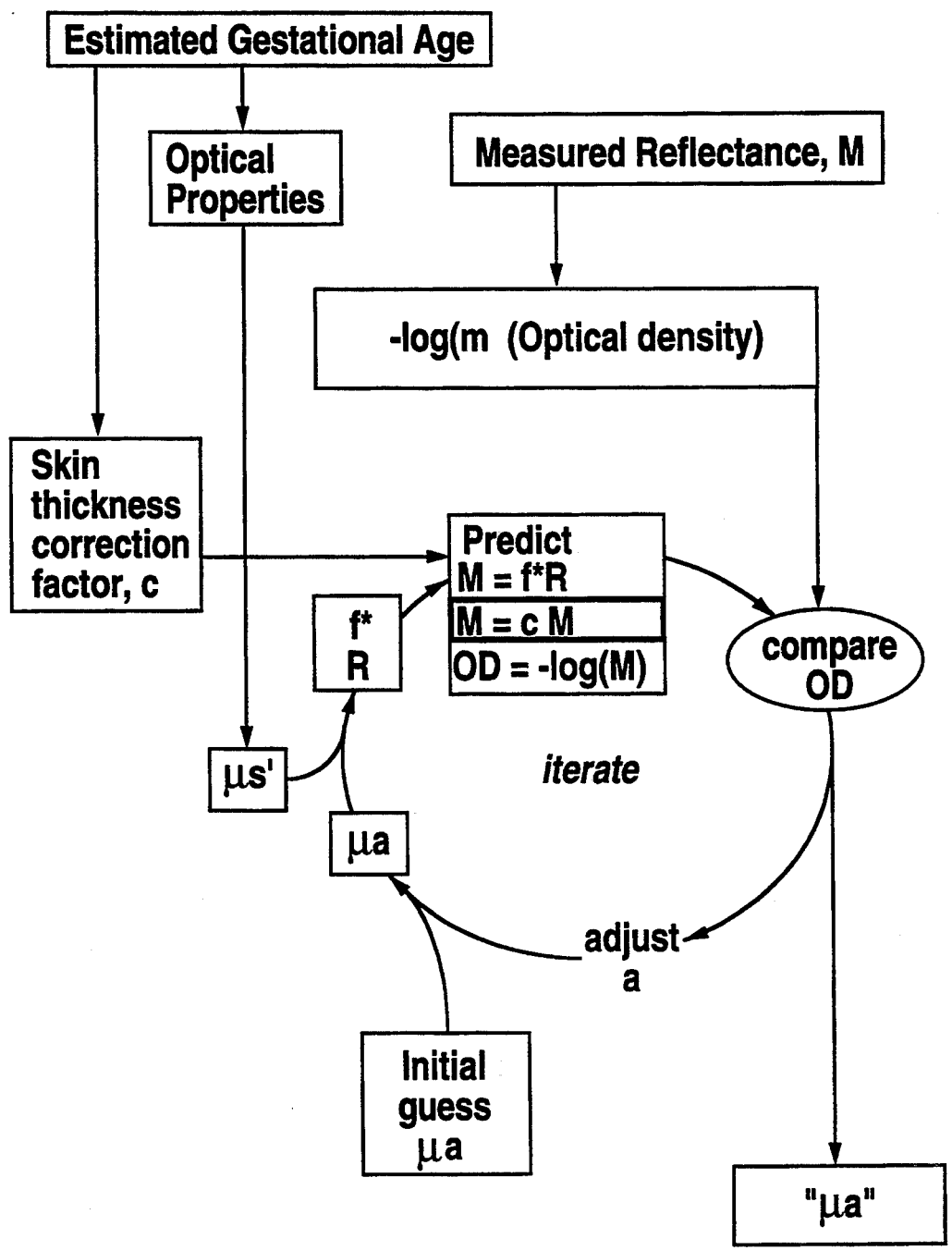
FIG. 47 is a more detailed flow chart of the skin thickness correction procedure of the method illustrated in the flow chart of FIG. 37.

The optical absorption at 460 and 585 nm are determined from the reflectance measurements, as explained in Section 3. At these two wavelengths, the reflectance measured from skin of finite thickness is less than that predicted for an infinitely thick medium, as explained above. The effect that finite skin thickness has on the measured reflectance can be corrected for approximately in the iteration procedure used to determine the absorbance. This correction is performed by lowering the predicted reflectance calculated during the iteration procedure, as to account for the finite skin thickness. This is illustrated in FIG. 47. The predicted reflectance, M, is multiplied by a constant, c, before it is compared to the actual measured reflectance. The constant, c is selected based on the estimated maturity of the skin, and is equal to the fraction of measured reflectance of finite thickness skin relative to infinite thickness skin, as presented in section C.2.2. Equation 4-18 in Section 4 relates skin thickness (in m) to gestational maturity (in weeks). It is rewritten here:

$$\text{Skin thickness } (m) = 22.5 + 25(\text{maturity}) \quad \text{(C-3)}$$

To determine the relationship between gestational maturity and the correction factor, c, Equation C-3 can be combined with Equations C-1 and C-2 to yield:

$$c = 1 - 0.26\exp(-0.088 \text{ maturity}) \quad \text{(C-4)}$$

for 460-nm light, and:

$$c = 1 - 0.27\exp(-0.057 \text{ maturity}) \quad \text{(C-5)}$$

for 585-nm light.

The adjustment in the iteration procedure described above will correct for the fact that skin is of finite thickness, but will not account for the variation of skin thicknesses for a given estimated gestational maturity. Reflectance measurements between 650 and 750 nm are not corrected in the manner above, since the correlation of 837-nm reflectance to gestational age is performed with uncorrected measurements. Therefore, this correlation also accounts for any increase in skin thickness associated with gestational age in addition to changes in scattering profiles.

APPENDIX D

References

Alexander, et al. (1979) "Skin Thickness with Pulsed Ultrasound," *Journal of Investigative dermatology*, 72: 17-19.

Anderson, et al. (1981) "The Optics of Human Skin," *J. Investigative Dermatology*, 77 (1): 13-19.

Anderson, et al. (1982) "Optical Properties of Human Skin," *The Science of Photomedicine*, eds. J. F. Regan and J. A. Parrish, Plenum Press, New York.

Andreozzi, G. M. (1987) "New Methods for the Diagnosis of Vasculopathies: Reflexion Light Rheography and Transcutaneous Oximetry," *Cardiologia*, 32(11):1431-1439.

Ballowitz, et al. (1970) "Spectral Reflectance of the Skin, Studies on Infant and Adult Humans, Wistar and Gunn Rats," *Biology of the Neonate*, 15:348-360.

Blois, M. S., (1966) "On the Spectroscopic Properties of Some Natural Melanins," *The Journal of Investigative Dermatology*, 47 (2): 162-166.

Bohren, et al. (1983) *Absorption and Scattering of Light by Small Particles*, J. Wiley & Sons, New York.

Boulnois, J. L. (1986) "Photophysical Processes in Recent Medical Laser Developments: a Review," *Lasers in Medical Science*, 1(1).

Burgeson, R. E. (1987) "The Collagens of the Skin," *Curr. Probl. Derm.*, 17:61-75.

Carr, K. (1988) "Sphere Flux Calculations," *Technical Notes, No. 1, Labsphere*, North Sutton, N.H.

Cheong, et al. (1990) "A Review of the Optical Properties of Biological Tissues," *IEEE Journal of Quantum Electronics*, 26 (12): 2166-2185.

Engel, et al. (1982) "Effect of race and other variables on transcutaneous bilirubinometry," *Pediatric Research*, 15:543.

Flock, et al. (1989) "Monte Carlo Modeling of Light Propagation in Highly Scattering Tissues- I: model predictions and comparison with diffusion theory," *IEEE Transactions on Biomedical Engineering*, 36(12):1162-1168.

Grandjean, P. (1990) *Skin Penetration: Hazardous Chemicals at Work*, Taylor and Francis, London.

Hannemann, et al. (1978) "Neonatal Serum Bilirubin from Skin Reflectance," *Pediatric Research*, 12:207-210.

Hannemann, R. E. (1982) "Evaluation of the Minolta Bilirubin Meter as a Screening Device in White and Black Infants," *Pediatrics*, 69(1).

Hegyi, et al. (1983) "Transcutaneous Bilirubinometry II, Dermal Bilirubin Kinetics during Phototherapy," *Pediatric Research*, 17(11):888-891.

Hegyi, T. (1986), "Transcutaneous Bilirubinometry in the Newborn Infant: State of the Art," *J. Clinical Monitoring*, 2:53.

Henyey, et al. (1941) "Diffuse Radiation in the Galaxy," *Astrophysical Journal*, 93:70-83.

Ishimuru, A. (1978) *Wave Propagation and Scattering in Random Media*, 2 Volumes, Academic Press, New York.

Jacques, et al. (1987a) "Modeling Optical and Thermal Distributions in Tissue During Laser Irradiation," *Lasers Surg. Med.*, 6:494-503.

Jacques, et al. (1987b) "Angular Dependence of HeNe Laser Light Scattering by Human Dermis," *Lasers in the Life Sciences*, 1(4):309-333.

Jacques, S. L. (1989a) "Simple Theory, Measurements, and Rules of Thumb for Dosimetry During Photodynamic Therapy," *SPIE*, 1065 (*Photodynamic Therapy: Mechanisms*).

Jacques, S. L. (1989b) "Time-Resolved Reflectance Spectroscopy in Turbid Tissues," *IEEE Transactions on Biomedical Engineering*, 36(12):1155-1161.

Jacques, S. L. (1990) "The Role of Skin Optics in Diagnostic and Therapeutic Uses of Lasers," *Lasers in Dermatology*, ed. R. Steiner, Springer-Verlag.

Jacques, et al. (1991) "The Melanosome: Threshold Temperature for Explosive Vaporization and Internal Absorption Coefficient during Pulsed Laser Irradiation," *Photochem. Photobiol.*, 51 (in press).

Johnson, et al. (1989) "Development of Human Embryonic and Fetal Dermal Vasculature," *J. of Invest. Dermatology*, 93(2 Supp):10S-17S.

Kapoor, et al. (1973) "Uptake and Release of bilirubin by the Skin," *Biochem. J.*, 136:35-43.

Kato, et al. (1985) "Early Detection of Lung Cancer by Means of Hematoporphyrin Derivative Fluorescence and Laser Photoradiation," *Clin. Chest Med.*, 6(2):237-253.

Katzir, A. (1989) "Optical Fibers in Medicine," *Scientific American*, 260 (5): 120-125.

Keijzer, et al. (1989) "Light Distributions in artery tissue: Monte Carlo Simulations for Finite-Diameter Laser Beams," *Lasers in Surgery and Medicine*, 9(2):148-154.

Kenny, et al. (1984) "Transcutaneous Bilirubin Monitoring of Newborns," *Annals of the New York Academy of Sciences*, 428: 251-262.

Kirkpatrick, et al. (1983) "The Newborn Infant," *Pediatrics*, ed. H. M. Maurer, New York, Chuchill Livingstone, pp. 51-97.

Knudsen, et al. (1989) "Skin Color and Bilirubin in Neonates," *Arch Dis Child*, 64:605.

Kollias, et al. (1985) "Spectroscopic Characteristics of Human Melanin in Vivo," *J Inves. Derm.*, 89(4):384-388.

Kollias, et al. (1987) "Absorption Mechanisms of Human Melanin in the Visible, 400-720 nm," *J Inves. Derm.*, 89(4):384-388.

Kopola, et al. (1990) "Skin Erythema Meter," *SPIE*, 1201 *Optical Fibers in Medicine* (V1990).

Kortum, G. F., (1969) *Reflectance Spectroscopy, Principals, Methods, Applications*, New York, Springer, pp. 25–37.

Krauss, et al. (1976) "Skin Reflectance in the Newborn Infant," *Pediatric Research*, 10:776–778.

Lewis, T. (1927) *The Blood Vessels of the Human Skin and Their Responses*, Shaw and Sons, Ltd., London.

Maisels, M. J., (1988) "Neonatal Jaundice," *Seminars in Liver Disease* (Vol. 8), pp. 148–162.

Marchesini, et al. (1989) "Extinction and Absorption Coefficients and Scattering Phase Functions of Human Tissue in vitro," *Applied Optics*, 28(12).

Millington, et al. (1983) *Skin*, Cambridge University Press, Cambridge.

Montagna, et al. (1974) *The Structure and Function of Skin*, Academic Press, New York.

Nahas, G. (1951) "Spectrophotometric Determination of Hemoglobin and Oxyhemoglobin in Whole Hemolysed Blood," *Science*, 113:723–724.

Patterson, et al. (1989) "Quantitative Reflectance Spectrophotometry for the Non-Invasive Measurement of Photosensitizer Concentration in Tissue During Photodynamic Therapy," *SPIE* (*Vol.* 1065) *Photodynamic Therapy: Mechanisms*, 115:122.

Pettit, et al. (1990) "Excimer Laser Induced Autofluorescence from Arteriosclerotic Human Arteries," *Lasers in Life Sciences*, 3:1–11.

Prahl, et al. (1989a) "A Monte Carlo Model of Light Propagation in Tissue," *Dosimetry of Laser Radiation in Medicine and Biology, SPIE Series* (*Vol. IS*), 5: 102–111.

Prahl, S. A. (1989b) "Light Transport in Tissue, Ph.D. dissertation, University of Texas, Austin.

Richards-Kortum, R. R. (1990) "The Laser as a Diagnostic Tool for Detecting Displasias and Cancers In Situ," Invited Talk, Laser Didactic Course, University of Texas MD Anderson Cancer Center.

Rosen, et al. (1990) "Immediate Pigment Darkening: Visual and Reflectance Spectrophotometric Analysis of Action Spectrum," *Photochemistry and Photobiology*, 51(5):583–588.

Rubaltelli, et al. (1971) "The Effect of Ligh on Cutaneous Bilirubin," *Biol. Neonate*, 18:457.

Saidi, I. S. (1990) "Light Transport in Neonatal Skin," *M. S. Dissertation*, Rice University.

Schumacher, R. E. (1990) "Noninvasive Measurements of Bilirubin in the Newborn," *Clinics in Perinatology*, 17(2):381.

Smith, et al. (1982) "Development of Dermal Connective Tissue in Human Embryonic and Fetal Skin," *Scanning Electron Microscopy, IV*:1745–1751.

Smith, et al. (1986) "Collagen Types I, III and V in Human Embryonic and Fetal Skin," *The American Journal of Anatomy*, 175: 507–521.

Turkel, S. B. (1990) "Autopsy Findings Associated with Neonatal Hyperbilirubinemia," *Clinics in Perinatology*, 17(2): 381–96.

van de Hulst, H. C. (1980) *Multiple Light Scattering: Tables, Formulas and Applications*, (2 Volumes), Academic Press, New York.

van Gemert, et al. (1989) "Skin Optics," *IEEE Transactions on Biomedical Engineering*, 36 (12).

Welch, et al. (1987) "Practical Models for Light Distribution in Laser-Irradiated Tissue," *Lasers in Surgery and Medicine* (6):488–493.

Wilson, et al. (1986) "The Effect of Photosentizer Concentration in Tissue on the Penetration Depth of Photoactivating Light," *Lasers Med Sci.*, 1:235.

Wilson, et al. (1990) "Optical Reflectance and Transmittance of Tissues: Principals and Applications," *IEEE Journal of Quantum Electronics*, 26(12):2186–2199.

Winkelman, et al. ( ) "Cutaneous Vascular Patterns in Studies with Injection Preparation and Alkaline Phophatase Reaction," *Advances in Biology of Skin, Blood Vessels and Circulation*, eds. Montagna W. and Ellis, R. A., Pergamon Press Oxford, Vol. 2, pp. 1–19.

Wukitsch, et al. (1988) "Pulse Oximetry: Analysis of Theory, Technology, and Practice," *J. Clin. Monit.*, 4(4):290–301.

Yamanuchi, et al. (1980) "Transcutaneous Bilirubinometry: Preliminary Studies of Noninvasive Transcutaneous Bilirubin Meter in the Okayama National Hospital," *Pediactrics*, 65:195–202.

Zrakit, D. (1986) Unpublished Masters Report, Dept. of Electrical Engineering, Massachusets Institute of Technology, Cambridge, Mass.

Appendix E

'Algorithm to determine the cutaneous bilirubin concentration
'Iyad Saidi
'Laser Biology Research Lab
'MD. Anderson Cancer Center
'Houston, TX 77030

```
open "c:\iyad\filelist.dat" for input as #1
'list of constants and variables used in the calculations
startwave=380      'the wavelength used to start graphing a line
lowscale=-0.5
fullscale=2      'the low and high limits of a graph
Dim  name$(100),havedone(300),x(300),y(300),y2(300)
logten=log(10)
```

```
gosub getnames:

input #1,junk$
input #1,numoffiles open "output.dat" for output as #2 muaskin460=27*exp(-0.006*460)
muaskin585=27*exp(-0.006*585)
muaskin650=27*exp(-0.006*650)

FOR n= 1 to numoffiles input #1,FILENAME$
  GOSUB COLLECTDATA:
      gosub calcratios:
      gosub findbili:
      gosub outputresults:

next n close #2
stop
end

'*********************************************************
*************** outputresults:
      print #2,muabili,chr$(9),totalbili,chr$(9),mua585,
chr$(9),melanin650
return '*********************************************************
****************
'*********************************************************
**************** collectdata:
dim wavelength(221),readings(221)
numvalues=221
' Routine to retrieve saved data and graph it
open FILENAME$ for input as #3
'will have 5 header lines
      input #3,comment$
      input #3,gestage,race,site,grams,pthstatus
```

```
    input  #3,totalbili,directbili,hematcrt
    print  filename$
    print  gestage,race,site,grams,pthstatus
    print  totalbili,directbili,hematcrt
    input  #3,junk$
    input  #3,junk$
    input  #3,firstnum
         if firstnum=380  then
    goto  inputwithwave:
    else
    goto  inputnowave:
    end if inputwithwave:
    wavelength(1)=firstnum
    input  #3,junk
    if junk<0  then
    readings(1)=junk
    else
    input  #3,readings(1)
    end if
    for i= 2 to 221
    input  #3,wavelength(i)
    input  #3,junk
    if junk<0  then
    readings(i)=junk
    else
    input  #3,readings(i)
    end if
    next i
    goto  finishedreading:

inputnowave:
    wavelength(1)=380
    readings(1)=firstnum
    for i= 2 to 221
    wavelength(i)=380   +((i-1)*2)
    input  #3,readings(i)
    next i
    goto  finishedreading:

finishedreading:
    close #3
```

```
m650=readings(((650-380)/2)+1)
m585=readings(((585-380)/2)+1)
m460=readings(((460-380)/2)+1)
return '********************************************************
'******************************************************** graphdata:
'scaling= 155 fullrange pixels on screen/range
    scaling=155/(fullscale-lowscale)
    for i=2 to numvalues
    wavelength=startwave+(2*(i-1))
'wavelength range shown graphed from 300 to 820
    x=wavelength-300+60
    y=170-((readings(i)-lowscale)*scaling)
    oldx= x-2
    oldy=170-((readings(i-1)-lowscale)*scaling)
    line(x,y)-(oldx,oldy)
    next i '       display pigment and blood level in box in corner
    line(430,0)-(639,32),,b
    locate 2,55
    print "              ";
    locate 2,55
    print "pigment = " pigment
    locate 3,55
    print "              ";
    locate 3,55
    print "ratio 420/585 = " ratio;

return
'********************************************************
*********
'********************************************************
********* setgraph:
screen 2
    cls
' print file specification and description
    locate 24,2
    print "                                              ";
    locate 24,2
```

```
    print filename$;
    locate 24,40
    print comment$;
'axis
    line(60,170)-(640,0),,b
'scaling= 155 fullrange pixels on screen/range
    scaling=155/(fullscale-lowscale)
'for fullscale label
    coll = cint(24/8)
    row=cint(15/8)
    locate row,coll
    print fullscale;
'ytics
    for i=cint(lowscale+0.5) to cint(fullscale-0.5)
    line(57,170-(i-lowscale)*scaling)-(63,170-(i-lowscale)*scaling)
    next i
'for lowscale label
    coll = cint(32/8)
    row=cint(170/8)
    locate row,coll
    print lowscale;
'xtics
    for i=1 to 6
    row=cint(184/8)
    coll=cint((60+(i-1)*100)/8)
    locate row,coll
    print 300+((i-1)*100)
    line ((60+(i-1)*100),167)-((60+(i-1)*100),173)
    next i return '*********************************************************
'*********************************************************
'************* graphline:
'scaling= 155 fullrange pixels on screen/range
    line(x1,point1)-(x2,point2)
return
'*********************************************************
'*********
```

```
findabs:
meas=10^(-1*meas)
tollerence=0.01    '+/- error with which the mua will converge
mua=1.0 'initial guess
'print lambda
for itterate=1 to 1000
gosub findfstarnR:
measguess=fstar*Reflect
'thickness correction
measguess=measguess*thickfactor
'end of thickness correction
if (((Measguess-meas)/meas)^2)^0.5 <tollerence then goto foundmua:
mua=mua*(1+((Measguess-meas)/meas))
'print itterate,meas,measguess,mua
next itterate
foundmua:
'print "itterations="itterate
'print "wavelength="lambda
'print "guessed m=";measguess,"mua ="mua
return findfstarnR:

'yint
if lambda=650 then
yint=-6
slope=0.68
end if if lambda=584 then
yint=-12
slope=1.10
end if if lambda=460 then
yint=-15.9
slope=1.5
end if musg=yint+(maturity*slope)
doverut=(1/((3*mua*(mua+musg))^0.5))/(mua+musg)

if doverut<0 then return
```

```
ldoverut=log(doverut)/logten
f=0.131+(0.070*ldoverut)+(0.210*ldoverut^2)+(0.036*ldoverut^3)
if lambda=650 then frteflon=0.31
if lambda=584 then frteflon=0.33
if lambda=460 then frteflon=0.37 fstar=f/frteflon                      'fstar=f/frteflon
logaprime=(log(musg/mua))/logten
Reflect=0.057+(0.1284*logaprime)+(0.138*logaprime^2)-
(0.027*logaprime^3)
return findbili:

maturity=10^((2.72+(10^-OD837))/2.43)   'from maturity vs OD837
function

'find 650 absorption
lambda=650
i=((lambda-380)/2)+1
mua=muaskin650
gosub findfstarnR:
meas=m650 melanin650=(meas)-(-log(fstar*reflect)/logten)
'print melanin650

'print "melanin650=   ";melanin650

'find absorption at 585
'print M585
lambda=584
i=((lambda-380)/2)+1
meas=m585
'adjust for melanin
meas=meas-(1.35*melanin650)
thickfactor=1-0.27*exp(-0.057*maturity)

gosub findabs:
mua585=mua
od585=-log(reflect)/logten
```

```
'find absorption at 460
lambda=460
i=((lambda-380)/2)+1
meas=m460

'adjust for melanin
meas=meas -(2.0*melanin650)
thickfactor=1-0.26*exp(-0.088*maturity)
gosub findabs:
mua460=mua muabili=(mua460)-(1.36*(mua585-muaskin585))
muabili=muabili-muaskin460 return
```

'************************************************************
'************************************************************

```
calcratios:
'this routine will calculate:
'           1. od837, By extrapolating OD 650 to 820
'first do linear regression from wavelinemin to wavelinemax
wavelinemin=650
wavelinemax=820
    sx=0
    sy=0
    sn=0
    sd=0
    for i=0 to (wavelinemax-wavelinemin)/2
    sx=sx+wavelinemin+(2*i)
    sy=sy+readings(i+(wavelinemin-380)/2+1)
    next i
    mx=sx/((wavelinemax-wavelinemin)/2+1)
    my=sy/((wavelinemax-wavelinemin)/2+1)
    for i= 0 to (wavelinemax-wavelinemin)/2
    xi=wavelinemin+(2*i)-mx
    sn=sn+(xi*readings(i+(wavelinemin-380)/2))
    sd=sd+(xi*xi)
```

```
next i
slope= sn/sd
yint=my-(slope*mx)
OD837=yint+(slope*837)
```
return

*******************************************************
****************

What is claimed is:

1. A method for the transcutaneous determination of bilirubin concentration in tissue, comprising:

illuminating said tissue with light;

detecting a frequency spectrum of light reflected from said tissue;

calculating, from a first portion of said spectrum, a first parameter indicative of a maturity of said tissue;

calculating, from a second portion of said spectrum, a second parameter indicative of an amount of melanin in said tissue;

calculating, form a third portion of said spectrum, a third parameter indicative of a blood content of said tissue;

calculating, from a fourth portion of said spectrum, a fourth parameter indicative of an uncorrected bilirubin concentration in said tissue; and calculating a connected bilirubin concentration in said tissue as a function of said first, second, third and fourth parameters.

2. The method of claim 1, wherein said first portion of said spectrum is red to infrared light.

3. The method of claim 2, said red to infrared light having wavelengths in the range of 650 nm to 800 nm.

4. The method of claim 1, wherein said second portion of said spectrum is red light.

5. The method of claim 4, said red light having a wavelength of approximately 650 nm.

6. The method of claim 1, wherein said third portion of said spectrum is yellow-orange light.

7. The method of claim of 6, said yellow-orange light having a wavelength of approximately 585 nm.

8. The method of claim 1, wherein said fourth portion of said spectrum is blue light.

9. The method of claim 8, wherein said blue light has a wavelength of approximately 460 nm.

10. The method of claim 1, further comprising:

calculating, from a fifth portion of said spectrum, a fifth parameter indicative of a depth of blood within said tissue; and calculating a concentration of bilirubin in said tissue as a function of said first, second, third, fourth and fifth parameters.

11. The method of claim 10, wherein said fifth portion of said spectrum is purple-blue light.

12. The method of claim 11, wherein said purple-blue light has a wavelength of approximately 420 nm.

13. An apparatus for detecting a concentration of bilirubin in tissue, comprising:

a light source adapted to direct light onto tissue under test;

a light detector, adapted to detect a spectrum of light reflected form said tissue; and a computer means, connected to said light source and light detector, for calculating a first parameter indicative of a maturity of said tissue form a magnitude of a first portion of said spectrum, for calculating a second parameter indicative of an amount of melanin in said tissue from a second portion of said spectrum, for calculating a third parameter indicative of a blood content of said tissue from a third portion of said spectrum, for calculating a fourth parameter indicative of a raw bilirubin concentration form a fourth portion of said spectrum, and for calculating bilirubin concentration in said tissue as a function of said first, second, third and fourth parameters.

* * * * *

UNITED STATES PATENT AND TRADEMARK OFFICE
CERTIFICATE OF CORRECTION

PATENT NO. : 5,353,790

DATED : October 11, 1994

INVENTOR(S) : Steven L. Jacques *et al.*

It is certified that error appears in the above-identified patent and that said Letters Patent is hereby corrected as shown below:

In claim 1, column 81, line 27, change "form" to --from--.

In claim 1, column 81, line 33, change "connected" to --corrected--.

In claim 13, column 82, line 36, change "form" to --from--.

In claim 13, column 82, line 45, change "form" to --from--.

Signed and Sealed this

Thirteenth Day of December, 1994

Attest:

BRUCE LEHMAN

*Attesting Officer*  *Commissioner of Patents and Trademarks*